(12) United States Patent
Dubois et al.

(10) Patent No.: US 10,973,840 B2
(45) Date of Patent: Apr. 13, 2021

(54) METHODS OF SENSITIZING TUMOR CELLS TO WEAK BASE CHEMOTHERAPEUTIC DRUGS

(71) Applicant: SOCPRA SCIENCES SANTÉ ET HUMAINES S.E.C., Sherbrooke (CA)

(72) Inventors: Claire Dubois, Sherbrooke (CA); Fabrice Lucien, Rochester, MN (US); Pierre-Paul Pelletier, Gatineau (CA)

(73) Assignee: SOCPRA SCIENCES SANTÉ ET HUMAINES S.E.C.

( * ) Notice: Subject to any disclaimer, the term of this patent is extended or adjusted under 35 U.S.C. 154(b) by 0 days.

(21) Appl. No.: 16/005,917

(22) Filed: Jun. 12, 2018

(65) Prior Publication Data

US 2018/0353525 A1 Dec. 13, 2018

Related U.S. Application Data

(60) Provisional application No. 62/518,775, filed on Jun. 13, 2017.

(51) Int. Cl.
| | | |
|---|---|---|
| *A61K 31/704* | (2006.01) | |
| *A61P 35/00* | (2006.01) | |
| *A61K 31/165* | (2006.01) | |
| *A61K 38/43* | (2006.01) | |
| *A61K 31/351* | (2006.01) | |
| *A61K 38/03* | (2006.01) | |

(52) U.S. Cl.
CPC .......... *A61K 31/704* (2013.01); *A61K 31/165* (2013.01); *A61K 31/351* (2013.01); *A61K 38/03* (2013.01); *A61K 38/43* (2013.01); *A61P 35/00* (2018.01)

(58) Field of Classification Search
None
See application file for complete search history.

(56) References Cited

PUBLICATIONS

Lucien et al. "Hypoxia-induced mobilization of NHE6 to the plasma membrane triggers endosome hyperacidification and chemoresistance," Nature Communications, vol. 8, Article No. 15884 (2017), pp. 1-15, published Jun. 21, 2017 (Year: 2017).*
Lucien et al. "Targeting endosomal pH for cancer chemotherapy," Molecular & Cellular Oncology, 2018, vol. 5, No. 3, e1435184, 3 pages. (Year: 2018).*
Ouyang et al. "Christianson syndrome protein NHE6 modulates TrkB endosomal signaling required for neuronal circuit development," Neuron. Oct. 2, 2013; 80(1): 97-112 (Year: 2013).*

* cited by examiner

*Primary Examiner* — Christina Bradley
(74) *Attorney, Agent, or Firm* — Lavery, De Billy, LLP; Julie Gauvreau

(57) ABSTRACT

The invention provides a method of sensitizing a tumor cells of a subject to a weak base chemotherapeutic drug comprising administering an effective amount of a NHE6-RACK1 blocker to the subject. It also provides a method of preventing or treating cancer or a symptom thereof in a subject, comprising (a) administering an effective amount of a NHE6-RACK1 blocker to the subject; and (2) administering an effective amount of a weak base chemotherapeutic drug to the subject. Also provided are compositions and kits comprising a NHE6-RACK1 blocker.

12 Claims, 55 Drawing Sheets
Specification includes a Sequence Listing.

HT-1080 scr

Vehicle

Dox 0.5μM 5 mm

HT-1080 NHE6$^{527-588}$

Vehicle

Dox 0.5μM 5 mm

Peptide C-4   534   LFRMWYNFDH   543

Peptide C-3   535   FRMWYNFDHN   544

Peptide C-2   536   RMWYNFDHNY   545

Peptide C-1   537   MWYNFDHNYL   546

Peptide C   538   WYNFDHNYLK   547

FIG. 13A

>NP_006350.1 sodium/hydrogen exchanger 6 isoform b precursor [Homo sapiens]
MARRGWRRAPLRRGVGSSPRARRLMRPLWLLLAVGVFDWAGASDGGGGEARAMDEEIVSEKQAEESHRQDSANLLIFILLLTL
TILTIWLFKHRRARFLHETGLAMIYGLLVGLVLRYGIHVPSDVNNVTLSCEVQSSPTTLLVTFDPEVFFNILLPPIIFYAGYS
LKRRHFFRNLGSILAYAFLGTAISCFVIGSIMYGCVTLMKVTGQLAGDFYFTDCLLFGAIVSATDPVTVLAIFHELQVDVELY
ALLFGESVLNDAVAIVLSSSIVAYQPAGDNSHTFDVTAMFKSIGIFLGIFSGSFAMGAATGVVTALVTKFTKLREFQLLETGL
FFLMSWSTFLLAEAWGFTGVVAVLFCGITQAHYTYNNLSTESQHRTKQLFELLNFLAENFIFSYMGLTLFTFQNHVFNPTFVV
GAFVAIFLGRAANIYPLSLLLNLGRRSKIGSNFQHMMMFAGLRGAMAFALAIRDTATYARQMMFSTTLLIVFFTVWVFGGGTT
AMLSCLHIRVGVDSDQEHLGVPENERRTTKAESAWLFRMWYNFDHNYLKPLLTHSGPPLTTTLPACCGPIARCLTSPQAYENQ
EQLKDDDSDLILNDGDISLTYGDSTVNTEPATSSAPRRFMGNSSEDALDRELAFGDHELVIRGTRLVLPMDDSEPPLNLLDNT
RHGPA

FIG. 13B

>NP_001317581.1 sodium/hydrogen exchanger 6 isoform d or X2 [Homo sapiens]
MDEEIVSEKQAEESHRQDSANLLIFILLLTLTILTIWLFKHRRARFLHETGLAMIYGLLVGLVLRYGIHVPSDVNNVTLSCEV
QSSPTTLLVTFDPEVFFNILLPPIIFYAGYSLKRRHFFRNLGSILAYAFLGTAISCFVIGSIMYGCVTLMKVTGQLAGDFYFT
DCLLFGAIVSATDPVTVLAIFHELQVDVELYALLFGESVLNDAVAIVLSSSIVAYQPAGDNSHTFDVTAMFKSIGIFLGIFSG
SFAMGAATGVVTALVTKFTKLREFQLLETGLFFLMSWSTFLLAEAWGFTGVVAVLFCGITQAHYTYNNLSTESQHRTKQLFEL
LNFLAENFIFSYMGLTLFTFQNHVFNPTFVVGAFVAIFLGRAANIYPLSLLLNLGRRSKIGSNFQHMMMFAGLRGAMAFALAI
RDTATYARQMMFSTTLLIVFFTVWVFGGGTTAMLSCLHIRVGVDSDQEHLGVPENERRTTKAESAWLFRMWYNFDHNYLKPLL
THSGPPLTTTLPACCGPIARCLTSPQAYENQEQLKDDDSDLILNDGDISLTYGDSTVNTEPATSSAPRRFMGNSSEDALDREL
AFGDHELVIRGTRLVLPMDDSEPPLNLLDNTRHGPA

FIG. 13C

>XP_016884713.1 PREDICTED: sodium/hydrogen exchanger 6 isoform X1 [Homo sapiens]
MDEEIVSEKQAEESHRQDSANLLIFILLLTLTILTIWLFKHRRARFLHETGLAMIYGLLVGLVLRYGIHVPSDVNNVTLSCEV
QSSPTTLLVNVSGKFYEYMLKGEISSHELNNVQDNEMLRKVTFDPEVFFNILLPPIIFYAGYSLKRRHFFRNLGSILAYAFLG
TAISCFVIGSIMYGCVTLMKVTGQLAGDFYFTDCLLFGAIVSATDPVTVLAIFHELQVDVELYALLFGESVLNDAVAIVLSSS
IVAYQPAGDNSHTFDVTAMFKSIGIFLGIFSGSFAMGAATGVVTALVTKFTKLREFQLLETGLFFLMSWSTFLLAEAWGFTGV
VAVLFCGITQAHYTYNNLSTESQHRTKQLFELLNFLAENFIFSYMGLTLFTFQNHVFNPTFVVGAFVAIFLGRAANIYPLSLL
LNLGRRSKIGSNFQHMMMFAGLRGAMAFALAIRDTATYARQMMFSTTLLIVFFTVWVFGGGTTAMLSCLHIRVGVDSDQEHLG
VPENERRTTKAESAWLFRMWYNFDHNYLKPLLTHSGPPLTTTLPACCGPIARCLTSPQAYENQEQLKDDDSDLILNDGDISLT
YGDSTVNTEPATSSAPRRFMGNSSEDALDRELAFGDHELVIRGTRLVLPMDDSEPPLNLLDNTRHGPA

FIG. 13D

>sp|P63244|RACK1_HUMAN Receptor of activated protein C kinase 1 OS=Homo sapiens
GN=RACK1 PE=1 SV=3
MTEQMTLRGTLKGHNGWVTQIATTPQFPDMILSASRDKTIIMWKLTRDETNYGIPQRALRGHSHFVSDVVISSDGQFALSGSW
DGTLRLWDLTTGTTTRRFVGHTKDVLSVAFSSDNRQIVSGSRDKTIKLWNTLGVCKYTVQDESHSEWVSCVRFSPNSSNPIIV
SCGWDKLVKVWNLANCKLKTNHIGHTGYLNTVTVSPDGSLCASGGKDGQAMLWDLNEGKHLYTLDGGDIINALCFSPNRYWLC
AATGPSIKIWDLEGKIIVDELKQEVISTSSKAEPPQCTSLAWSADGQTLFAGYTDNLVRVWQVTIGTR

FIG. 13E

>NP_004243.1 Na(+)/H(+) exchange regulatory cofactor NHE-RF1 [Homo sapiens]
MSADAAAGAPLPRLCCLEKGPNGYGFHLHGEKGKLGQYIRLVEPGSPAEKAGLLAGDRLVEVNGENVEKETHQQVVSRIRAAL
NAVRLLVVDPETDEQLQKLGVQVREELLRAQEAPGQAEPPAAAEVQGAGNENEPREADKSHPEQRELRPRLCTMKKGPSGYGF
NLHSDKSKPGQFIRSVDPDSPAEASGLRAQDRIVEVNGVCMEGKQHGDVVSAIRAGGDETKLLVVDRETDEFFKKCRVIPSQE
HLNGPLPVPFTNGEIQKENSREALAEAALESFRPALVRSASSDTSEELNSQDSPPKQDSTAPSSTSSSDPILDFNISLAMAKE
RAHQKRSSKRAPQMDWSKKNELFSNL

METHODS OF SENSITIZING TUMOR CELLS TO WEAK BASE CHEMOTHERAPEUTIC DRUGS

CROSS REFERENCE TO RELATED APPLICATIONS

This application claims benefit, under 35 U.S.C. § 119(e), of U.S. provisional application Ser. No. 62/518,775, filed on Jun. 13, 2017. The documents above is incorporated herein in its entirety by reference.

STATEMENT REGARDING FEDERALLY SPONSORED RESEARCH OR DEVELOPMENT

N.A.

FIELD OF THE INVENTION

The present invention relates to methods of sensitizing tumor cells to weak base chemotherapeutic drugs. More specifically, the present invention is concerned with methods of sensitizing tumor cells to weak base chemotherapeutic drugs by preventing NHE6 localization at the plasma membrane.

REFERENCE TO SEQUENCE LISTING

Pursuant to 37 C.F.R. 1.821(c), a sequence listing is submitted herewith as an ASCII compliant text file named Sequence Listing 14692-53_5 T25, that was created on Jun. 12, 2018 and having a size of 36 kilobytes. The content of the aforementioned file named Sequence Listing 14692-53_5 T25 is hereby incorporated by reference in its entirety.

BACKGROUND OF THE INVENTION

A major challenge in treating cancer is resistance to therapy[1]. A mainstay of therapy for the management of many cancers includes chemotherapy regimens based on anthracyclines or anthracycline analogs (Doxorubicin [Dox], daunorubicin [Dnr] or mitoxantrone [Mtx])[2-4]. Yet, the response rates are suboptimal and very few effective therapeutic options are currently available to treat patients who failed to respond to anthracycline treatments[3,5,6].

The success of chemotherapy depends on the ability of the drug to accumulate in the cellular compartment where its target is located (e.g., nucleus). Hence, tumors use various mechanisms to escape the deleterious effect of cytotoxic drugs. Among these, primary or acquired multidrug resistance (MDR) remains the primary hurdle to curative cancer therapy. Although drug resistance is most often attributed to genetic alterations, one major factor contributing to drug resistance is the physical tumor microenvironment ($pO_2$ and pH) that has consistently been shown to impede drug accumulation in cancer cells[7,8,9]. MDR is a complex and multifactorial process with up-regulation of cell-surface efflux pumps (such as ATP-binding cassette transporter family of p-glycoprotein and MDR-associated proteins) being the most studied and clinically tested aspect[10]. Cells adapted to a hypoxic and acidic microenvironment in vitro display up-regulated activity of p-glycoprotein which is thought to contribute to drug resistance[11,12]. However, results from clinical trials targeting these transporters have been so far rather disappointing and it is clear that more detailed knowledge about the causes and mechanisms of drug resistance are needed in order to find new ways to counter MDR[13].

Accumulating evidence indicates that sequestration of anticancer drugs in intracellular vesicles outside of their targeted compartments contributes significantly to the MDR phenotype[14,15]. One mechanism involved in this process is the pH-dependent drug partitioning within cells caused by a direct effect of pH gradients on drug distribution[16,17]. This model predicts that weakly basic chemotherapeutic drugs that include anthracyclines, will concentrate in acidic compartments such as intracellular vesicles where they will be trapped in their protonated, membrane-impermeant, form[8]. Given that most commonly used anticancer drugs have nuclear targets, such sequestration into vesicles will not only result in insufficient drug accumulation at the target site, but will also increase drug extrusion through exocytosis[18]. Therefore, pH-dependent alterations in intracellular drug distribution is an important fundamental mechanism associated with drug resistance, but surprisingly little is known about the molecular regulators of this process.

The present description refers to a number of documents, the content of which is herein incorporated by reference in their entirety.

SUMMARY OF THE INVENTION

The present invention shows that hypoxia not only leads to acidification of the tumor microenvironment, but also induces endosome hyperacidification. The acidity of the vesicular lumen, together with the alkaline pH of the cytoplasm, gives rise to a strong intracellular pH gradient that drives intravesicular drug trapping and chemoresistance.

More particularly, the present invention shows that hypoxia induces drug resistance in cancer cells by regulating pH-dependent drug partitioning within intracellular compartments. More particularly, it shows that the endosomal NHE6 $Na^+/H^+$ exchanger induces weak base chemotherapeutic drug resistance by being relocated from endosomes to the plasma membrane of hypoxic cancer cells and thereby inducing endosome hyperacidification that leads to exacerbation of the vesicular pH gradient. Mechanistically, hypoxia-induced acidification in endosomal pH is due to mislocalization of the $Na+/H+$ exchanger isoform 6 (NHE6) at the plasma membrane due to its enhanced binding to the receptor of activated protein C kinase 1 (RACK1) through a protein kinase C (PKC)-dependent mechanism. Such interaction explains the raise of NHE6 at the plasma membrane since RACK1 knockdown, modulation of PKC activity, or interference with RACK1-NHE6 binding greatly affected hypoxia-induced NHE6 plasma membrane mobilization. Modulation of either PKC activity or RACK1-NHE6 interaction also recovered normal endosomal pH, and restored weak base drug sensitivity in hypoxic cells. Using a RACK1-NHE6 competing peptide, the inventors were able to prevent the plasma membrane mobilization of NHE6, by reducing its binding to the scaffold PKC-RACK1 complex, leading to the reversal of endosome hyperacidification and in vitro and in vivo cancer cell sensitization to weak base chemotherapeutics (e.g., doxorubicin).

The present invention therefore provides a therapy specifically targeting this tumor microenvironment-driven mechanism leading to enhanced drug toxicity in hypoxic cells, while sparing normal tissues.

More specifically, in accordance with the present invention, there are provided the following items:

1. A method of sensitizing a tumor cells of a subject to a weak base chemotherapeutic drug comprising administering an effective amount of a NHE6-RACK1 blocker to the subject.

2. A method of preventing or treating cancer or a symptom thereof in a subject, comprising administering (a) an effective amount of a NHE6-RACK1 blocker; and (b) an effective amount of a weak base chemotherapeutic drug, to the subject.

3. The method of item 2, wherein (a) and (b) are simultaneous.

4. The method of item 2, wherein (a) and (b) are sequential.

5. The method of any one of items 1 to 4, wherein the weak base chemotherapeutic drug is an anthracycline.

6. The method of item 5, wherein the weak base chemotherapeutic drug is daunorubicin, doxorubicin, or mitoxantrone, or a pharmaceutically acceptable salt thereof.

7. The method of any one of items 1 to 6, wherein the NHE6-RACK1 blocker is a peptide of at least 4 (consecutive) amino acids of the cytoplasmic tail of human NHE6. More specifically at least 5, 6, 7, 8, 9 or 10 (consecutive) amino acids of the cytoplasmic tail of human NHE6.

8. The method of item 5, wherein the NHE6-RACK1 blocker is a peptide of at least 4 (consecutive) amino acids of the amino acid sequence at positions 527 to 591 of human NHE6. More specifically at least 5, 6, 7, 8, 9 or 10 (consecutive) amino acids of the amino acid sequence at positions 527 to 591 of human NHE6.

9. The method of item 8, wherein the peptide comprises at least 4 consecutive amino acids of the amino acid sequence at positions 527 to 591 of human NHE6, including tryptophan 538 and tyrosine 539. More specifically at least 5, 6, 7, 8, 9 or 10 (consecutive) amino acids of the amino acid sequence at positions 527 to 591 of human NHE6, including tryptophan 538 and tyrosine 539.

10. The method of item 8, wherein the peptide comprises at least 4 consecutive amino acids of the amino acid sequence at positions 530 to 547 of human NHE6, including tryptophan 538 and tyrosine 539. More specifically at least 5, 6, 7, 8, 9 or 10 (consecutive) amino acids of the amino acid sequence at positions 530 to 547 of human NHE6, including tryptophan 538 and tyrosine 539.

11. The method of item 8, wherein the peptide comprises at least 4 consecutive amino acids of the amino acid sequence at positions 536 to 545 of human NHE6, including tryptophan 538 and tyrosine 539. More specifically at least 5, 6, 7, 8, 9 or 10 (consecutive) amino acids of the amino acid sequence at positions 536 to 545 of human NHE6, including tryptophan 538 and tyrosine 539.

12. The method of item 8, wherein the peptide comprises RMWYNFDHNY (SEQ ID NO: 7).

13. A composition comprising (a) a NHE6-RACK1 blocker; and (b) (i) a weak base chemotherapeutic drug; (ii) at least one pharmaceutically acceptable carrier; or (iii) a combination or (i) and (ii).

14. The composition of item 13, wherein the weak base chemotherapeutic drug is an anthracycline.

15. The composition of item 14, wherein the weak base chemotherapeutic drug is daunorubicin, doxorubicin, or mitoxantrone, or a pharmaceutically acceptable salt thereof.

16. The composition of any one of items 13 to 15, wherein the NHE6-RACK1 blocker is a peptide of at least 4 (consecutive) amino acids of the cytoplasmic tail of human NHE6. More specifically at least 5, 6, 7, 8, 9 or 10 (consecutive) amino acids of the cytoplasmic tail of human NHE6.

17. The composition of item 16, wherein the NHE6-RACK1 blocker is a peptide of at least 4 (consecutive) amino acids of the amino acid sequence at positions 527 to 591 of human NHE6. More specifically at least 5, 6, 7, 8, 9 or 10 (consecutive) amino acids of the amino acid sequence at positions 527 to 591 of human NHE6.

18. The composition of item 17, wherein the peptide comprises at least 4 consecutive amino acids of the amino acid sequence at positions 527 to 591 of human NHE6, including tryptophan 538 and tyrosine 539. More specifically at least 5, 6, 7, 8, 9 or 10 (consecutive) amino acids of the amino acid sequence at positions 527 to 591 of human NHE6, including tryptophan 538 and tyrosine 539.

19. The composition of item 17, wherein the peptide comprises at least 4 consecutive amino acids of the amino acid sequence at positions 530 to 547 of human NHE6, including tryptophan 538 and tyrosine 539. More specifically at least 5, 6, 7, 8, 9 or 10 (consecutive) amino acids of the amino acid sequence at positions 530 to 547 of human NHE6, including tryptophan 538 and tyrosine 539.

20. The composition of item 17, wherein the peptide comprises at least 4 consecutive amino acids of the amino acid sequence at positions 536 to 545 of human NHE6, including tryptophan 538 and tyrosine 539. More specifically at least 5, 6, 7, 8, 9 or 10 (consecutive) amino acids of the amino acid sequence at positions 536 to 545 of human NHE6, including tryptophan 538 and tyrosine 539.

21. The composition of item 17, wherein the peptide comprises RMWYNFDHNY (SEQ ID NO: 7).

22. A kit comprising (a) a NHE6-RACK1 blocker; and (b) (i) a weak base chemotherapeutic drug; (ii) at least one pharmaceutically acceptable carrier; (iii) instructions to use same in the prevention or treatment of atherosclerosis or of a symptom thereof; or (iv) a combination of at least two of (i) to (iii). In a specific embodiment, instructions are to use same in the treatment of atherosclerosis or of a symptom thereof.

23. The kit of item 14, wherein the weak base chemotherapeutic drug is an anthracycline.

24. The kit of item 14, wherein the weak base chemotherapeutic drug is daunorubicin, doxorubicin, or mitoxantrone, or a pharmaceutically acceptable salt thereof.

25. The kit of any one of items 14 to 16, wherein the NHE6-RACK1 blocker is a peptide of at least 4 (consecutive) amino acids of the cytoplasmic tail of human NHE6.

26. The kit of any one of items 14 to 16, wherein the NHE6-RACK1 blocker is a peptide of at least 4 (consecutive) amino acids of the amino acid sequence at positions 527 to 591 of human NHE6. More specifically at least 5, 6, 7, 8, 9 or 10 (consecutive) amino acids of the amino acid sequence at positions 527 to 545 of human NHE6.

27. The kit of item 26, wherein the peptide comprises at least 4 consecutive amino acids of the amino acid sequence at positions 527 to 591 of human NHE6, including tryptophan 538 and tyrosine 539. More specifically at least 5, 6, 7, 8, 9 or 10 (consecutive) amino acids of the amino acid sequence at positions 527 to 545 of human NHE6, including tryptophan 538 and tyrosine 539.

28. The kit of item 26, wherein the peptide comprises at least 4 consecutive amino acids of the amino acid sequence at positions 530 to 547 of human NHE6, including tryptophan 538 and tyrosine 539. More specifically at least 5, 6, 7, 8, 9 or 10 (consecutive) amino acids of the amino acid sequence at positions 530 to 545 of human NHE6, including tryptophan 538 and tyrosine 539.

29. The kit of item 26, wherein the peptide comprises at least 4 consecutive amino acids of the amino acid sequence at positions 536 to 545 of human NHE6, including tryptophan 538 and tyrosine 539. More specifically at least 5, 6, 7, 8, 9 or 10 (consecutive) amino acids of the amino acid sequence at positions 536 to 545 of human NHE6, including tryptophan 538 and tyrosine 539.

30. The kit of item 26, wherein the peptide comprises RMWYNFDHNY (SEQ ID NO: 7).

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

(FIG. 1A) Mean fluorescence intensities of nuclear Dox were measured in HT-1080 cells incubated for 4 h in the presence of media of different pHs as indicated in this figure. (n=3 independent experiments with >20 cells/experimental condition). (FIGS. 1B-G) MTT assay dose-response curves for HT-1080 (FIGS. 1B-D) and MDA-MB-231 cells (FIGS. 1E-G) cultured in normoxia or hypoxia for 72 h and in presence or absence of increasing Dox concentrations (n=3-5 independent experiments) and in presence or absence of neutralizing agents: Chloroquine (Cq) (10 μM) or Bafilomycin A1 (Baf) (100 nM). (FIGS. 1H-K) Cell viability using the trypan blue exclusion method for HT-1080 (FIGS. 1H,J) and MDA-MB-231 cells (FIGS. 1I,K) cultured under normoxic or hypoxic conditions in presence or absence of neutralizing agents: Chloroquine (Cq) (10 μM) or Bafilomycin A1 (Baf) (100 nM). (n=3-4 independent experiments). Bars represent the mean±SEM (* P<0.05,  P<0.01, * P<0.001, One-way ANOVA (FIG. 1A), unpaired Student's t-test (FIGS. 1B-K).

(FIGS. 2A-B) Representative confocal microscopy images showing Dox fluorescence in MDA-MB-231 (FIG. 2A) and HT-1080 cells (FIG. 2B) cultured for 4 h in normoxia (21% $O_2$) or hypoxia (1% $O_2$). Endosomal compartments were stained with Alexa Fluor 633-conjugated transferrin (Tfn). Scale bar=5 μm, magnification is 60×. (FIGS. 2C-D) Percentage of Dox fluorescence within Tfn-labeled endosomes or DAPI-stained nucleus in MDA-MB-231 (FIG. 2C) and HT-1080 cells (FIG. 2D); (n=3 independent experiments with >75 cells/experimental condition). (FIGS. 2E-F) Quantitation of EEA1+- (FIG. 2E) and LAMP2+-vesicles (FIG. 2F) per cell in HT-1080 cells cultured for 4 h in normoxia or hypoxia (n=3 independent experiments with >25 cells/experimental condition). (FIGS. 2G-J) Percentage of Dox fluorescence within Tfn-labeled endosomes (FIGS. 2G and I) or DAPI-stained nucleus (FIGS. 2H and J) of MDA-MB-231 and HT-1080 cells cultured under normoxic or hypoxic conditions in presence or absence of neutralizing agents: Chloroquine (Cq) (10 μM) or Bafilomycin A1 (Baf) (100 nM). (n=3 independent experiments with >75 cells/experimental condition. Bars represent the mean±SEM (* P<0.05, ** P<0.01, unpaired Student's t-test).

(FIGS. 3A-B) Representative confocal images of pH-sensitive probe HPTS localization in MDA-MB-231 (FIG. 3A) or HT-1080 cells (FIG. 3B) labeled with Alexa$^{546}$-conjugated Tfn (endosomes) or Lysotracker™ (lysosomes). (FIGS. 3C-D) Percentage of colocalization of HPTS with Alexa$^{546}$-conjugated Tfn or Lysotracker™ showing predominant labeling within endosomes in MDA-MB-231 (FIG. 3C) or HT-1080 cells (FIG. 3D) (n=3 independent experiments with >150 cells/experimental condition). Scale bar=10 μm and magnification is 40×. (FIGS. 3E-F) Endosomal/lysosomal pH measured in MDA-MB-231 (FIG. 3E) or HT-1080 cells (FIG. 3F) cultured in normoxia or hypoxia (n=3 independent experiments with >75 cells/condition). (FIGS. 3G-H) Endosomal pH (Tfn-positive vesicles) in MDA-MB-231 (FIG. 3G) or HT1080 (FIG. 3H) cells cultured for 4 h under normoxic or hypoxic conditions (n=3 independent experiments with >75 cells/experimental condition). (FIGS. 3I-J) Cytosolic pH measured with SNARF-1 pH-sensing probe in MDA-MB-231 (FIG. 3I) or HT1080 (FIG. 3J) cells cultured for 4 h under normoxic or hypoxic conditions in presence or absence of EIPA, a selective NHE1 inhibitor (25 μM) (n=3 independent experiments with >75 cells/experimental condition). (FIGS. 3K-L) Endosomal/lysosomal pH in MDA-MB-231 (FIG. 3K) or HT-1080 cells (FIG. 3L) cultured in normoxia or hypoxia for 4 h in presence or absence of the neutralizing agents, Bafilomycin A1 (Baf, 100 nM) or Chloroquine (Cq, 10 μM) (n=3-5 independent experiments with >75 cells/experimental condition). Bars represent the mean±SEM (* P<0.05, P<0.01, *P<0.001, unpaired Student's t-test).

(FIGS. 4A-B) mRNA (FIG. 4A) and protein levels (FIG. 4B) of NHE6 in HT-1080 cells stably transfected with shRNA directed against NHE6 or scrambled shRNA. (FIGS. 4C-D) mRNA (FIG. 4C) and protein levels (FIG. 4D) of NHE9 in HT-1080 cells stably transfected with shRNA against NHE9 or scrambled shRNA. RPLPO and α-tubulin were used as controls for qPCR and Western-blots, respectively (n=4 independent experiments). (FIG. 4E) Endosomal/lysosomal pH in NHE6- or NHE9-knockdown HT-1080 cells cultured under normoxic or hypoxic conditions for 4 h (n=3 independent experiments with >75 cells/experimental condition). (FIG. 4F-G) mRNA levels of NHE6 in MDA-MB-231 cells stably transfected with shRNA directed against NHE6 (FIG. 4F), NHE9 (FIG. 4G) or scrambled shRNA. RPLPO was used as control for qPCR (n=3 independent experiments). (FIG. 4H) Endosomal/lysosomal pH in NHE6- or NHE9-knockdown MDA-MB-231 cells cultured under normoxic or hypoxic conditions for 4 h (n=3 independent experiments with >75 cells/experimental condition). (FIG. 4I) Percentage of Dox fluorescence within Tfn-positive endosomes of NHE6-knockdown MDA-MB-231 cells cultured under normoxic or hypoxic conditions (n=4 independent experiments with >30 cells/experimental condition). (FIGS. 4J-K) Representative confocal images in NHE6-knockdown HT-1080 cells (FIG. 4J) and quantification (FIG. 4K) of DOX within Tfn-positive endosomes of NHE6- or NHE9-knockdown cells cultured under normoxic or hypoxic conditions for 4 h (n=3 independent experiments with >75 cells/experimental condition). (FIG. 4L) Endosomal/lysosomal pH in NHE6-overexpressing cells cultured under normoxic or hypoxic conditions for 4 h (n=3 independent experiments with >75 cells/experimental condition). Scale bar is 5 μm and magnification 60×. Bars represent the mean±SEM ( P<0.01, *P<0.001, unpaired Student's t-test).

(FIG. 5A) Representative confocal microscopy images of NHE6 localization in HT-1080 cells transfected with NHE6-GFP and labeled with EEA1-directed antibodies (early endosomes), Alexa546-conjugated Tfn (early/recycling endosomes) or Rab7 antibodies (late endosomes) Arrows indicate colocalization of NHE6-GFP with the endosomal markers. Scale bar is 10 µm and magnification 60×. (FIG. 5B) Percentage of NHE6-GFP staining in early (EEA±), recycling (Tfn-F) and late endosomes (Rab7-F) in HT-1080 cells (n=3 independent experiments with 75 cells/experimental condition). ND, not detectable.

(FIGS. 6A-F) MDA-MB-231 or HT-1080 cells stably transfected with NHE6-GFP were incubated under normoxic or hypoxic conditions for 4 h. (FIG. 6A) Representative confocal images of NHE6 localization in MDA-MB-231 cells. Plasma membrane (PM) was stained by cell-surface biotinylation. Scale bar=10 µm and magnification is 60×. (FIGS. 6B-C) Percentage of NHE6 at the plasma membrane of MDA-MB-231 (FIG. 6B) or HT-1080 cells (FIG. 6C); (n=4 independent experiments with >100 cells/experimental condition). (FIGS. 6D-G) mRNA and protein levels of NHE6 in MDA-MB-231 (FIGS. 6D, F) and HT-1080 cells (FIGS. 6E, G) cultured in normoxia or hypoxia for the indicated time. CA9 mRNA expression was used as a positive control. RPLPO and β-actin were used as controls for qPCR and Western-blots, respectively (n=3 independent experiments). Plasma membrane relocalization of NHE6 in hypoxia is a reversible event. (FIG. 6H) HT-1080 cells stably transfected with NHE6-GFP were incubated under normoxic or hypoxic conditions for 4 h or 24 h. The 4 h time point was followed by reoxygenation for 1 h or 2 h or cells. Representative confocal images of NHE6 localization in HT-1080 cells. Plasma membrane (PM) was stained by cell-surface biotinylation. Scale bar is 5 µm and magnification 60×. (FIG. 6I) Percentage of NHE6 at the plasma membrane of HT-1080 cells (n=2-3 independent experiments with >25 cells/experimental condition). (FIG. 6J) Representative confocal images of colocalization of NHE6 with early endosome marker EEA1 in MDA-MB-231 cells. Scale bar=10 µm, magnification 60×. (FIGS. 6K-L) Percentages of NHE6 colocalization with EEA1 in MDA-MB-231 (FIG. 6K) or HT-1080 cells (FIG. 6L); (n=3 independent experiments with >75 cells/experimental condition). Bars represent the mean±SEM ( $P<0.01$, *$P<0.001$, unpaired Student's t-test).

(FIG. 7A) Co-immunoprecipitation of endogenous RACK1 with HA-tagged NHE6 from transiently transfected HT-1080 cells incubated under normoxia or hypoxia for the indicated times. Data represent 5% of the total cell extract used for each immunoprecipitation. (FIG. 7B) Immunoblot analysis of HT-1080 cell lysates 48 h after transfection with non-targeting siRNA or RACK1-specific siRNA. α-tubulin was used as a loading control. The blots shown in (FIG. 7A) and (FIG. 7B) are representative of four and three independent experiments, respectively. (FIGS. 7C-D) Quantification of NHE6-GFP at the plasma membrane (FIG. 7C) and at EEA1-positive endosomes (FIG. 7D) in HT-1080 cells transfected with scrambled siRNA or RACK1-specific siRNA (n=3-4 independent experiments and >75 cells/experimental condition). (FIG. 7E) Endosomal/lysosomal pH measured in HT-1080 cells in presence of nontargeting siRNA or RACK1-specific siRNA (n=3 independent experiments with >75 cells/experimental condition). (FIGS. 7F-G) Percentage of Dox fluorescence within DAPI-stained nucleus (FIG. 7F) and Tfn-labeled endosomes (FIG. 7G) of HT-1080 cells (n=3-4 independent experiments and >75 cells/experimental condition). Bars represent the mean±SEM (** $P<0.01$, unpaired Student's t-test).

(FIGS. 8A-B) MDA-MB-231 (FIG. 8A) and HT-1080 (FIG. 8B) cells were incubated in normoxia or hypoxia in the presence or absence of the PKC activator PDBu (100 nM). Cell lysates were analysed by western blotting using a phospho-(Ser) PKC substrate antibody. Alpha-tubulin was used as a loading control. The immunoblot shown is representative of three independent experiments. (FIGS. 8C-F) HT-1080 cells were cultured for 4 h under 21% $O_2$ or 1% 02 in the presence or absence of PDBu (100 nM), PKC inhibitor GF-109203x (200 nM) or vehicle (DMSO). Co-immunoprecipitation of endogenous RACK1/PKC (FIG. 8C) or NHE6-RACK1 (FIG. 8D) complex in HT-1080 cells. Data represent 5% of the total cell extract used for each immunoprecipitation. (FIGS. 8E, F) Quantification of NHE6 at the plasma membrane (FIG. 8E) and at endosomes (FIG. 8F); (n=3-5 independent experiments with >80 cells/experimental condition). (FIG. 8G) Endosomal/lysosomal pH measurements (n=4 independent experiments with >80 cells/experimental condition). (FIG. 8H) Quantification of DOX within the nucleus (n=5 independent experiments with >125 cells/experimental condition). Bars represent the mean±SEM (* $P<0.05$,  $P<0.01$, *$P<0.001$, unpaired Student's t-test).

(FIG. 9A) Co-immunoprecipitation of endogenous RACK1 with GFP-tagged NHE6. Data represent 5% of the total cell extract used for each immunoprecipitation. Data are representative of at least four independent experiments. (FIGS. 9B-C) Quantification of NHE6-GFP at the plasma membrane (FIG. 9B) and at EEA1-positive endosomes (FIG. 9C) (n=5 independent experiments with >125 cells/experimental condition). FIG. 9D. The NHE6527-588 peptide blocks NHE6 relocalization in hypoxic cells. Representative confocal microscopy images of NHE6 localization with EEA1 in HT-1080 cells stably transfected with NHE6-GFP and transiently transfected with a plasmid encoding the NHE6527-588 peptide or a scrambled peptide and incubated under 1% 02 or 21% 02 for 4 h. Scale bar is 10 µm with magnification 60×. (FIG. 9E) Endosomal/lysosomal pH (n=5 independent experiments with >100 cells/experimental condition). (FIGS. 9F-G) Percentage of Dox within DAPI-stained nucleus (FIG. 9F) and Tfn-labeled endosomes (FIG. 9G) (n=4 independent experiments with >100 cells/experimental condition). Bars represent the mean±SEM (* $P<0.05$, ** $P<0.01$, unpaired Student's t-test).

(FIG. 10A) Timeline of the human tumor cell xenograft assay in the chorioallantoic membrane (CAM) of chick embryos. (FIG. 10B) mRNA expression of hypoxic markers CA9, GLUT1 and MCT4 in HT-1080-derived tumors extracted from the chorioallantoic membrane 7 days post-implantation. RPLPO was used as loading control, (n=4 independent experiments with 5 tumors/experiment). (FIG. 10C) Representative staining of HT-1080 tumors extracted from CAM showing hypoxic regions (Pimo+) and hypoxic cells (CAIX+). Nuclei were stained with DAPI. Scale bar is 100 µm and magnification 10×. (FIGS. 10D-E)

Tumor volumes from HT-1080 (FIG. 10D) and MDA-MB-231 cells (FIG. 10E) grown onto CAM and treated with various concentrations of Dox (n=5-7 embryos/group). (FIG. 10F) Representative images of tumors grown on CAM from HT-1080 cells transfected with scrambled peptide (HT-1080 scr) or NHE6$^{527\text{-}588}$ peptide (HT-1080 NHE6$^{527\text{-}588}$) and treated with 0.5 µM Dox. (FIGS. 10G-H) Tumor volumes of HT-1080 (FIG. 10G) and MDA-MB-231 cells (FIG. 10H) grown on CAM in presence of scrambled sequence (scr) or NHE6$^{527\text{-}588}$ sequence and treated with 0.5 µM Dox (FIG. 10G) or 1 µM Dox (FIG. 10H) (n=5-9 embryos/group). Bars represent the mean±SEM (* P<0.05,  P<0.01, *P<0.001, unpaired Student's t-test).

(FIGS. 11A-B) mRNA levels od MDR1 in MDA-MB-231 (FIG. 11A) and HT-1080 cells (FIG. 11B) cultured in normoxia or hypoxia 1 for 4 h or 8 h. CA9 mRNA expression was used as a positive control. RPLPO was used as an internal control for qPCR (n=3 independent experiments). (FIG. 11C) Representative confocal microscopy images of P-gp localization in HT-1080 cells labeled with Ab directed against EEA1 (early endosomes) or LAMP2 (lysosomes). Scale bar=10 µm and magnification is 60×. (FIGS. 11D-E) Percentage of MDR1 staining in early endosomes (EEA-F) and lysosomes (LAMP2-F) in HT-1080 cells (n=2 independent experiments with >20 cells/experimental condition). ND, not detectable. Bars represent the mean±SEM (* P<0.05,  P<0.01, *P<0.001, unpaired Student's t-test).

(FIG. 12A) Arbitrary separation of the 62aa [527-588]-NHE6 segment into 11 overlapping 10aa peptides (SEQ ID NOs: 3 to 5 and 10 to 17) identified from 1 to 11 (identified respectively as A to K in FIG. 12B). (FIG. 12B) Interface energy score of the 11 peptides submitted to Flexpepdock™ molecular docking refinement protocol with the tentative NHE binding pocket at the surface of RACK1. Interface energy score is expressed in Rosetta energy units. (FIG. 12C) Generation of four intermediate peptides to peptides B and C (peptide C (SEQ ID NO: 5)). New peptides were identified from C-1 to C-4 (Peptide C-1 (SEQ ID NO: 6); Peptide C-2 (SEQ ID NO: 7); Peptide C-3 (SEQ ID NO: 8); and Peptide C-4 (SEQ ID NO: 9)). (FIG. 12D) I_sc of peptide C and four derivatives submitted to Flexpepdock™ molecular refinement protocol with the possible RACK1 binding site.

FIGS. 13A-E. Amino acid sequences of human NHE6 isoform B (SEQ ID NO: 62) (FIG. 13A); human NHE6 isoform D (SEQ ID NO: 63) (FIG. 13B); human NHE6 isoform X1 (SEQ ID NO: 64) (FIG. 13C); human RACK1 (SEQ ID NO: 65) (FIG. 13D); and human Na+/H+ Exchanger Regulatory Factor (NHERF1) (SEQ ID NO: 66) (FIG. 13E).

DESCRIPTION OF ILLUSTRATIVE EMBODIMENTS

Compounds

Figure 1A:
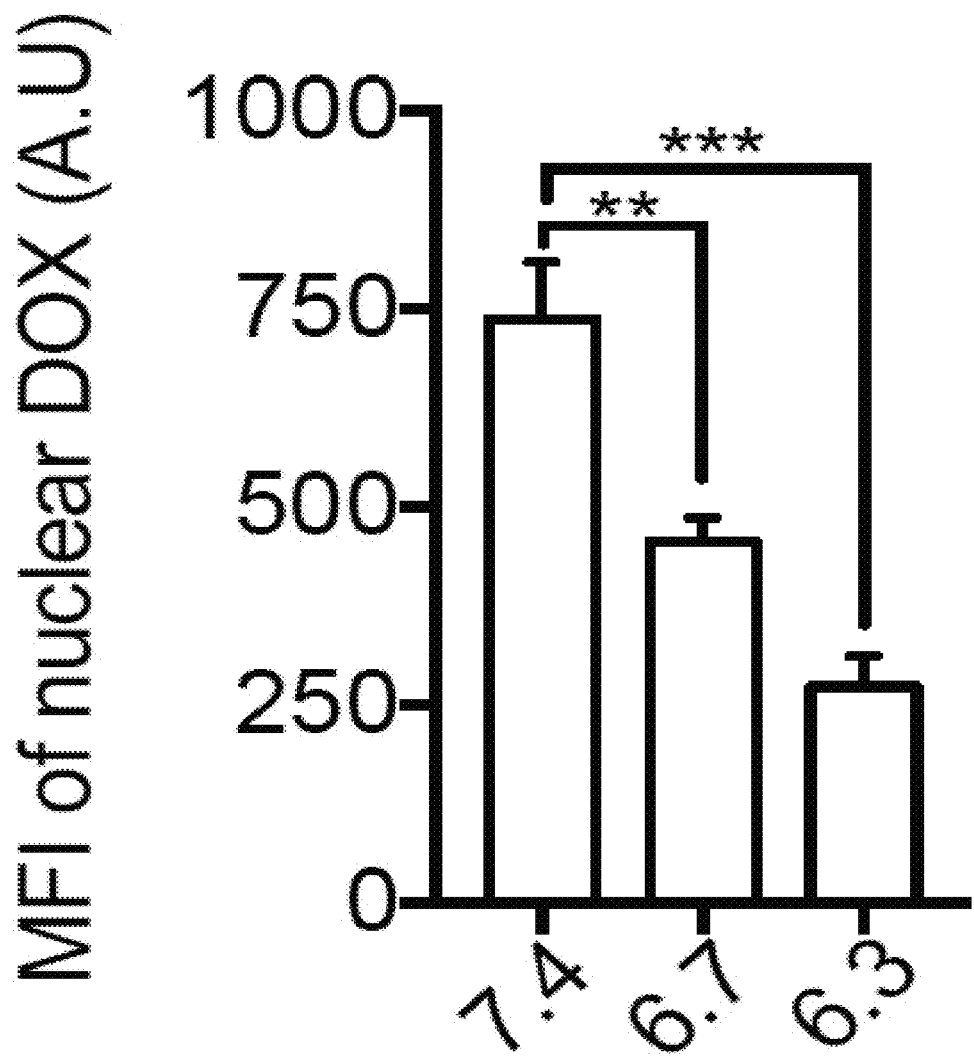
FIGS. 1A-K. Extracellular acidification reduces doxorubicin (Dox) localization in HT-1080 cells and neutralizing agents prevents hypoxia-induced Dox resistance in cancer cells.
Figure 1B:
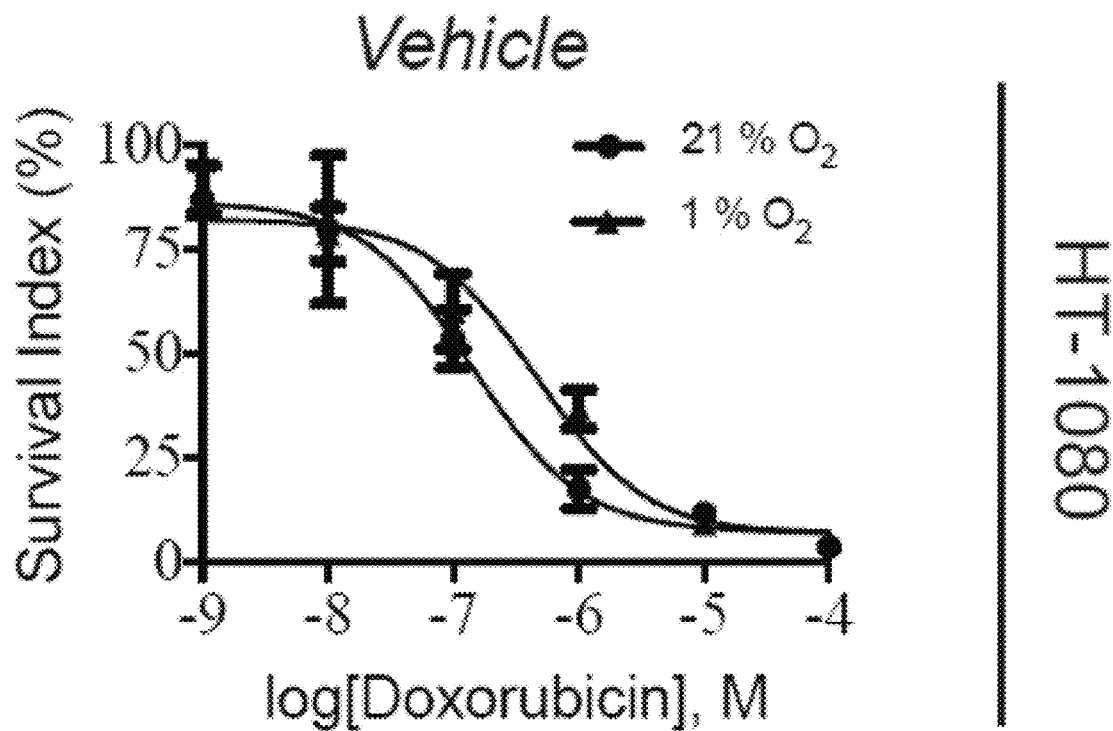
Figure 1C:
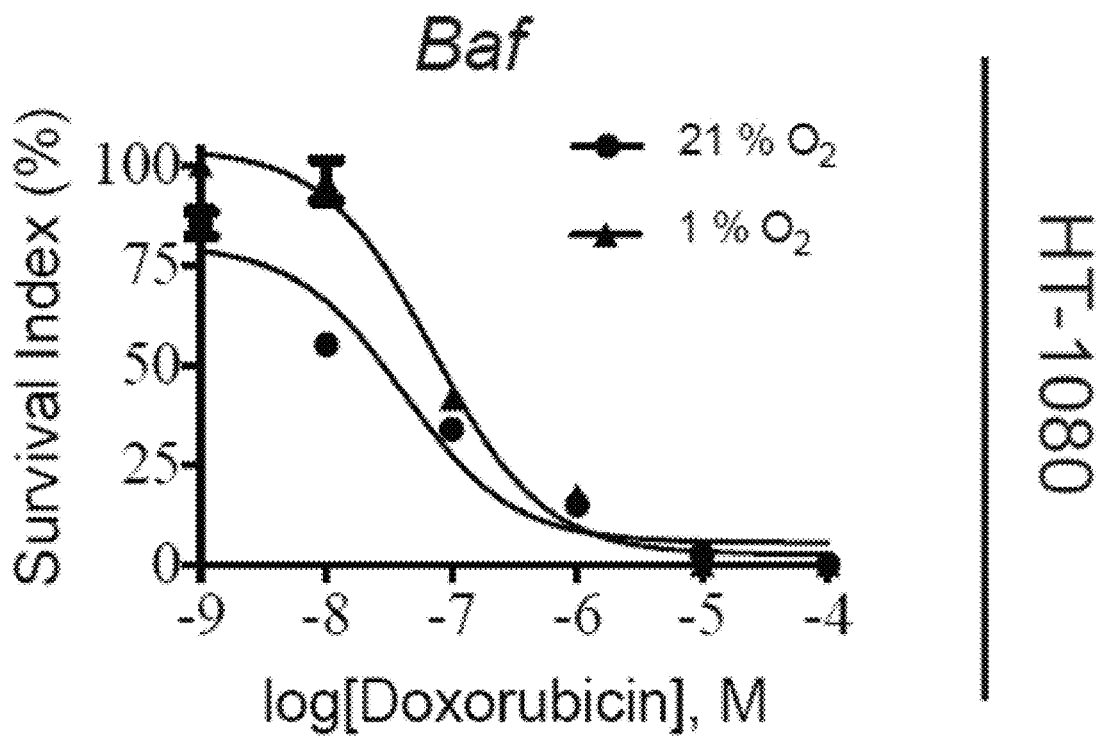
Figure 1D:
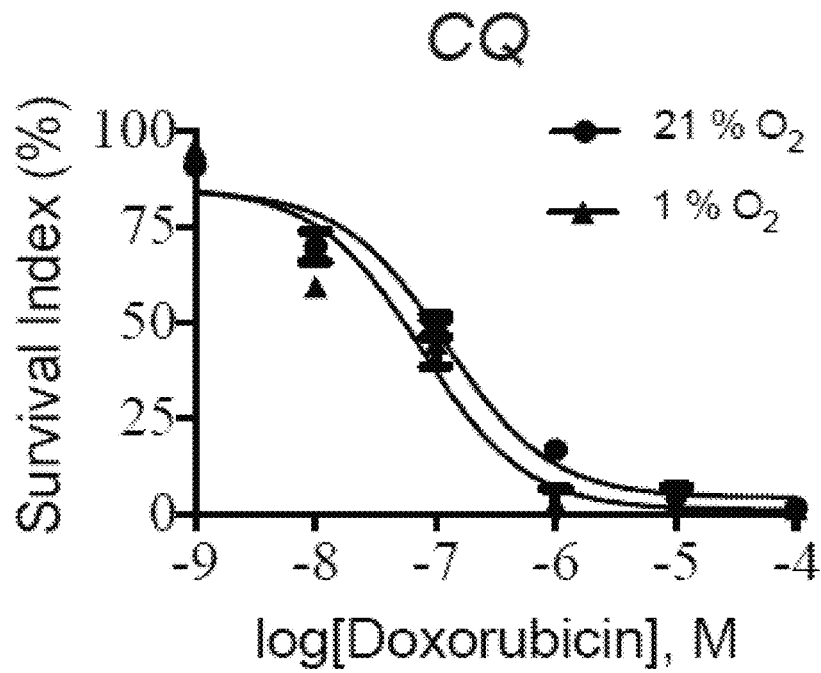
Figure 1E:
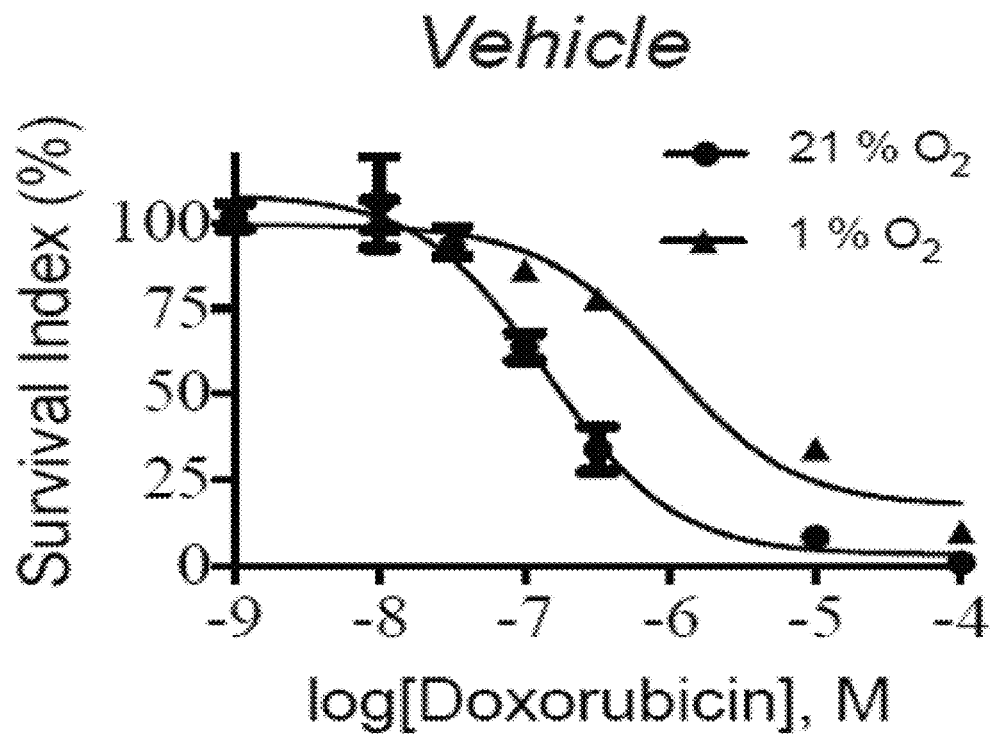
Figure 1F:
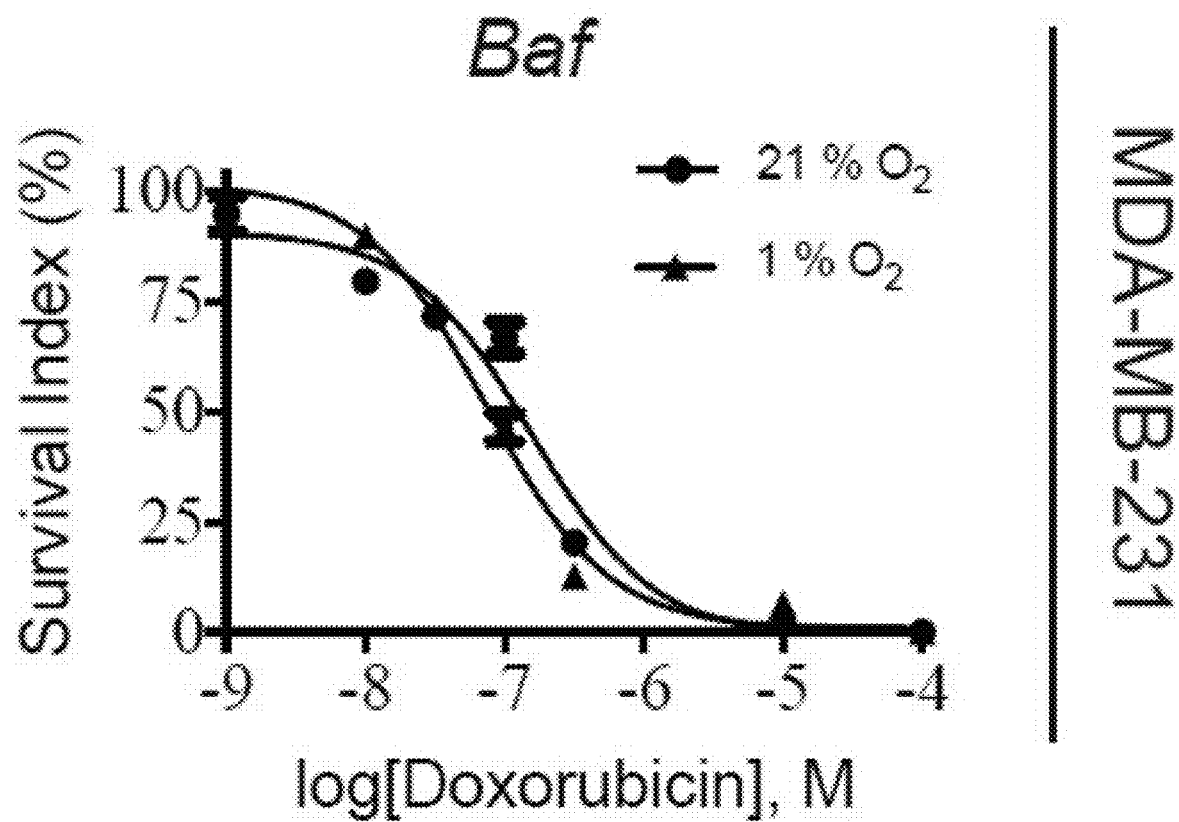
Figure 1G:
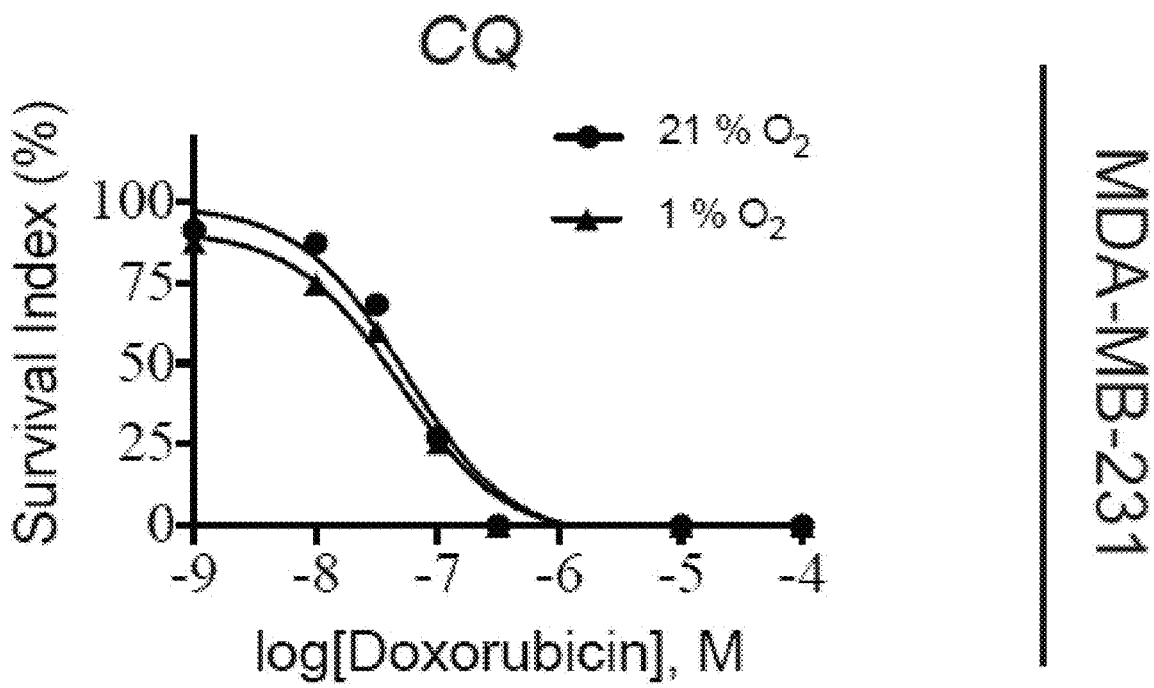
Figure 1H:
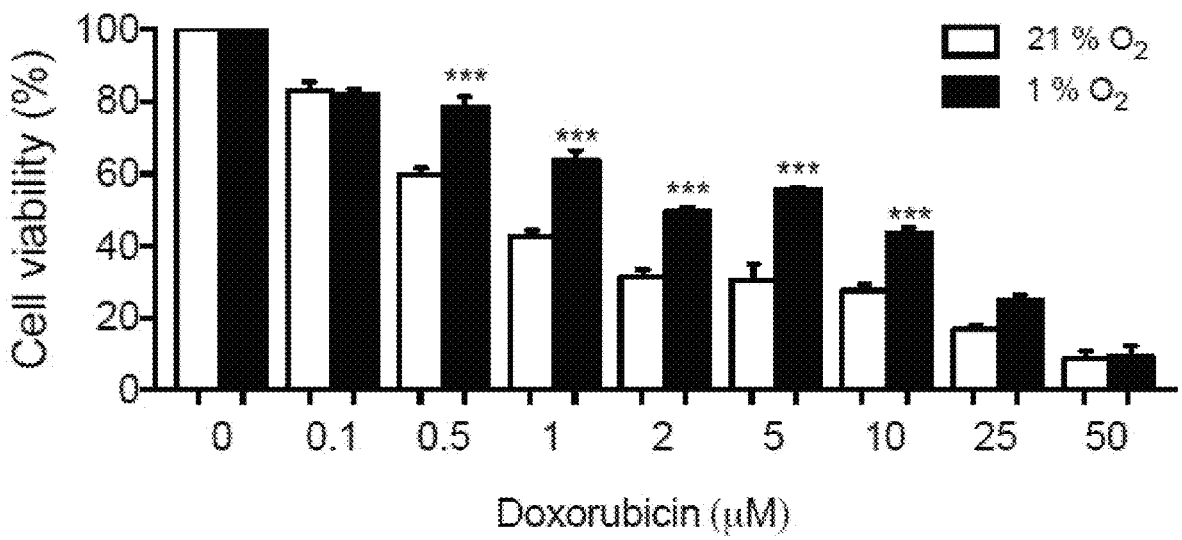
Figure 1I:
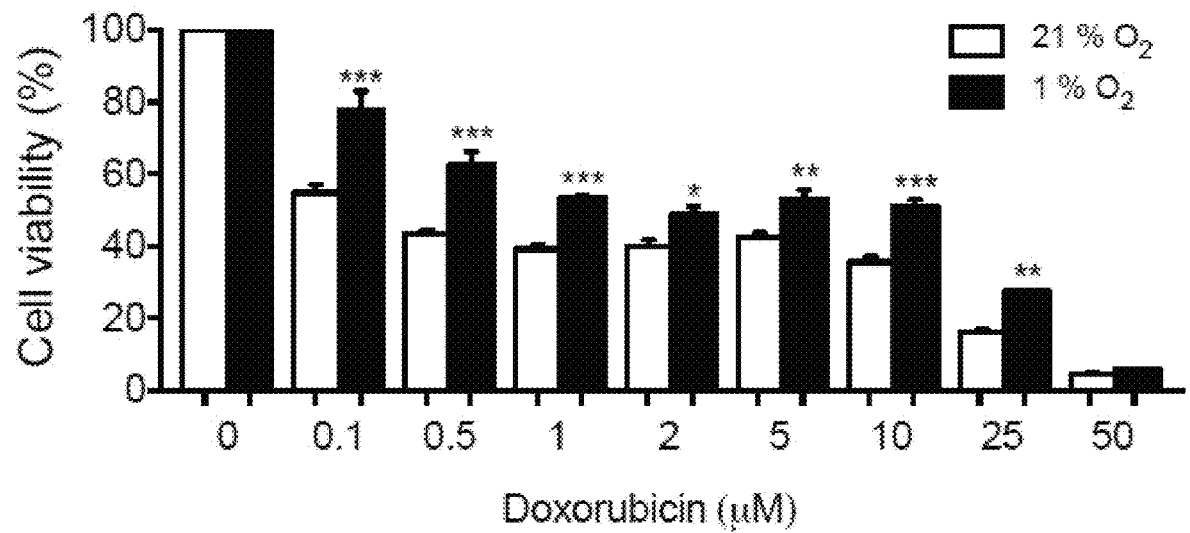
Figure 1J:
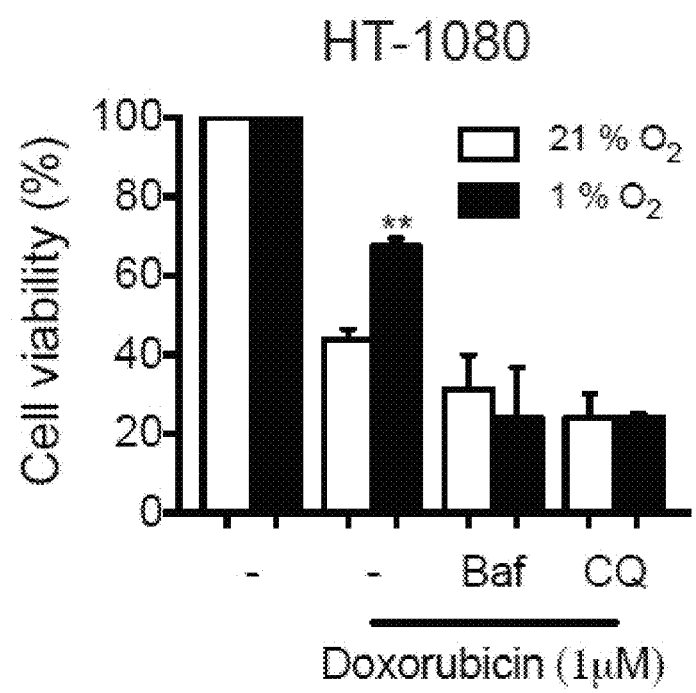
Figure 1K:
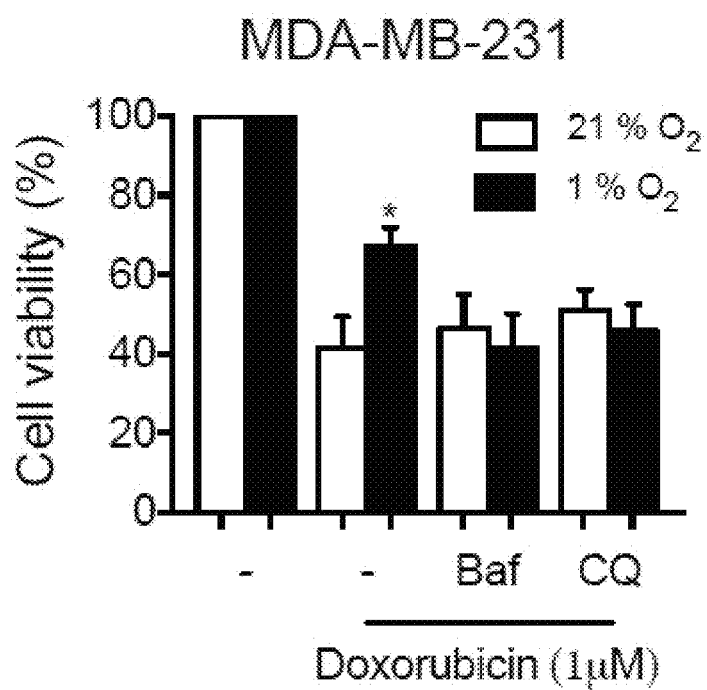

The present invention provides compounds that are able to directly or indirectly decrease NHE6-RACK1 binding in tumor cells (e.g., hypoxic tumor cells); directly or indirectly decrease NHE6 localization/mobilization on the plasma membrane of tumor cells (e.g., hypoxic tumor cells); directly or indirectly increase localization or NHE6 in the endosomes of tumor cells (e.g., hypoxic tumor cells); directly or indirectly decrease proportion of NHE6 localized at the plasma membrane of tumor cells vs. NHE6 localized at endosome membranes of tumor cells (e.g., hypoxic tumor cells); directly or indirectly increase the pH of endosome lumen/compartment of tumor cells (e.g., hypoxic tumor cells); directly or indirectly decrease the pH of cytosol of tumor cells (e.g., hypoxic tumor cells); directly or indirectly decrease the pH gradient between the endosome lumen/compartment and cytosol of tumor cells (e.g., hypoxic tumor cells); directly or indirectly decrease weak base chemotherapeutic drug concentration/capture/sequestration in tumor cells (e.g., hypoxic tumor cells) endosomes; directly or indirectly increase cytosol and/or nuclear concentration of weak base chemotherapeutic drugs in tumor cells (e.g., hypoxic tumor cells); directly or indirectly prevent, decrease or reverse resistance (increase sensitivity) of tumor cells (e.g., hypoxic tumor cells) against weak base chemotherapeutic drugs; and/or directly or indirectly increase antitumoral activity of weak base chemotherapeutic drugs against tumor cells (e.g., hypoxic tumor cells and methods of use thereof. In specific embodiment, it also refers to compounds that are able to decrease expression and/or activity (e.g., binding to NHE6) of RACK1 (RACK1 inhibitor) and to compounds that are able to decrease expression and/or activity of PKC (PKC inhibitor). Without being so limited, such compounds may be peptides, antibodies, antibody fragments, shRNAs, RNAi or small molecules.

Without being so limited, compounds that are able directly or indirectly decrease NHE6 localization/mobilization at the plasma membrane of tumor cells include compounds that modulate expression and/or activity (e.g., binding with NHE6) of NHE6 binding partners other than RACK1. Such other binding partner include NHERF1 (EBP50), a PDZ and EBD domain-containing scaffolding. NHE6 contains a D-S-D-L motif (SEQ ID NO: 61) adjacent to the RACK1-interacting region and susceptible to interact with the PDZ domain of NHERF1. According to preliminary data (not shown) NHERF1 binds to NHE6 and this event is regulated by hypoxia. Because PKC has been shown to phosphorylate NHERF1 to control the stoichiometry of NHERF to assemble protein complexes, it is possible that RACK1 functions as a hub between PKC and NHERF1 leading to cell-surface mobilization of NHE6. Without being so limited, compounds that may inhibit binding of NHERF1 to NHE6 are peptides comprising the 588-DSDL-591 (SEQ ID NO: 61) sequence or a peptide mimetic therefrom.

Without being so limited, PKC inhibitors include anti-PKC antibodies, LY333531, a PKC-beta-specific inhibitor, ISSI-3521, a PKC-alpha antisense inhibitor, UCN-01 and CGP41251, two partially isoform-specific PKC inhibitors, ruboxistaurin, chelerythrine, miyabenol C, myricitrin, gossypol, verbascoside, BIM-1, bryostatin 1, 1-O-Hexadecyl-2-O-acetyl-sn-glycerol, baicalein, K-252a, Go6983, broad spectrum PKC inhibitor 228514; melittin, inhibits Gs and stimulates Gi activity 11931; GF 109203X, protein kinase C inhibitor 4128; LY 333531 hydrochloride, protein kinase C inhibitor; selective for β isozymes47381; Go 6976, potent protein kinase C inhibitor; selective for α and β isozymes 22538; rottlerin, reported PKCδ inhibitor 16103; cherelythrine chloride, Cell-permeable protein kinase C inhibitor133010; PKC ζ pseudosubstrate, PKC ζ inhibitor peptide (attached to cell-permeable vector)17911; calphostin C, potent selective and photo-dependent PKC inhibitor16264; PKC 412, 29923; PKC δ pseudosubstrate, selective cell-permeable PKC inhibitor peptide (attached to vector) 1792; C-1, protein kinase C inhibitor 0543; ZIP (Scrambled), control peptide for ZIP (Cat. No. 2549) 32152; D-erythro-Sphingosine (synthetic), protein kinase C inhibitor 0633; (±)-palmitoylcarnitine chloride, Intermediate in fatty acid oxidation 0609; Ro 32-0432 hydrochloride, potent orally active PKC inhibitor 15872; dihydrosphingosine, protein kinase C inhibitor 0749; [Ala$^{107}$]-MBP (104-118); protein kinase C inhibitor 1900; K-252c, protein kinase C inhibitor22871; [Ala$^{113}$]-MBP (104-118); protein kinase C inhibitor 1901; ZIP biotinylated, biotinylated peptide for ZIP (Cat. No. 2549)3290; CGP 53353, selective inhibitor of PKCβII24422; [Glu$^{27}$]-PKC (19-36), inactive control peptide for PKC (19-36) (Cat. No. 4058) 40591; PKC (19-36), pseudosubstrate peptide; inhibitor of PKC40581; TCS 21311, potent JAK3 inhibitor. Also inhibits GSK-3β and PKC4221; bisindolylmaleimide II, potent PKC inhibitor and nicotinic receptor antagonist41281; ZIP, cell-permeable inhibitor of atypical PKC isozyme PKMζ25495; enzastaurin, potent PKCβ inhibitor 5994.

Without being so limited, compounds of the present invention include NHE6-RACK1 blockers. As used herein the terms "NHE6-RACK1 blocker" refer to a compound able to directly or indirectly limit or prevent the interaction of NHE6 with RACK1. In a specific embodiment, it refers to a peptide (i.e. "NHE6-RACK1 blocking peptide"), an antibody, an antibody fragment, an shRNA, an RNAi or a small molecule that is able to limit or prevent the interaction of NHE6 with RACK1.

Illustrative amino acid sequences of human NHE6 are shown in FIGS. 13A-C. Useful NHE6-RACK1 blocking peptides according to the present invention include a peptide comprising at least at least 4 (more specifically at least 5, 6, 7, 8, 9 or 10) contiguous (i.e. consecutive) amino acids of the cytoplasmic tail of NHE6. In a more specific embodiment, using the numbering of isoform b of human NHE6 (FIG. 13A), it refers to a peptide comprising at least 4 (more specifically at least 5, 6, 7, 8, 9 or 10)) contiguous amino acids of the NHE6 fragment 527-591 or a peptidomimetic derived therefrom: 527-TKAESAWLFRMWYNFDH-NYLKPLLTHSGPPLTTTLPACCGPIARCLTSPQAY-ENQEQLKDDDSDL-591 (SEQ ID NO: 1).

In a more specific embodiment, it refers to a peptide comprising at least 4 (more specifically at least 5, 6, 7, 8, 9 or 10)) contiguous amino acids of the NHE6 fragment 527-588 or a peptidomimetic derived therefrom: 527-TKAESAWLFRMWYNFDHNYLKPLLTHSGPPLTTTL-PACCGPIARCLTSPQAYENQEQLKDDD-588 (SEQ ID NO: 2).

In a more specific embodiment, it refers to a peptide comprising at least 4 (more specifically at least 5, 6, 7, 8, 9 or 10)) contiguous amino acids of any of the following NHE6 peptides or a peptidomimetic derived of any of them: 527-TKAESAWLFR-536 (SEQ ID NO: 3) (peptide A), 533-WLFRMWYNFD-542 (SEQ ID NO: 4) (peptide B), 538-WYNFDHNYLK-547 (SEQ ID NO: 5) (peptide C), 537-MWYNFDHNYL-546 (SEQ ID NO: 6) (peptide C-1), 536-RMWYNFDHNY-545 (SEQ ID NO: 7) (peptide C-2), 535-FRMWYNFDHN-544 (SEQ ID NO: 8) (peptide C-3), 534-LFRMWYNFDH-543 (SEQ ID NO: 9) (peptide C-4), 543-HNYLKPLLTH-552 (SEQ ID NO: 10) (peptide D), 548-PLLTHSGPPL-557 (SEQ ID NO: 11) (peptide E), 553-SGPPLTTTLP-662 (SEQ ID NO: 12) (peptide F), 558-TTTLPACCGP-567 (SEQ ID NO: 13) (peptide G), 563-ACCGPIARCL-572 (SEQ ID NO: 14) (peptide H), 569-ARCLTSPQAY-578 (SEQ ID NO: 15) (peptide I), 574-SPQAYENQEQ-583 (SEQ ID NO: 16) (peptide J), and 579-ENQEQLKDDD-588 (SEQ ID NO: 17) (peptide K). In a more specific embodiment, it refers to a peptide comprising at least 4 (more specifically at least 5, 6, 7, 8, 9 or 10)) contiguous amino acids of any one of 533-WL-FRMWYNFD-542 (SEQ ID NO: 4) (peptide B), 536-RMWYNFDHNY-545 (SEQ ID NO: 7) (peptide C-2), or a peptidomimetic derived therefrom.

In a more specific embodiment, it refers to a peptide comprising at least 4 (more specifically at least 5, 6, 7, 8, 9 or 10) contiguous amino acids of a NHE6 peptide comprising at least tryptophan 538 and tyrosine 539 or a peptidomimetic derived of any of them comprising at least tryptophan 538 and tyrosine 539. Without being so limited, such peptide includes any one of AWLFRMWYNF (SEQ ID NO: 18), SAWLFRMWYN (SEQ ID NO: 19) and ESAWL-FRMWY (SEQ ID NO: 20); WYNFDHNYL (SEQ ID NO: 21), MWYNFDHNY (SEQ ID NO: 22), RMWYNFDHN (SEQ ID NO: 23), FRMWYNFDH (SEQ ID NO: 24), LFRMWYNFD (SEQ ID NO: 25), WLFRMWYNF (SEQ ID NO: 26), AWLFRMWYN (SEQ ID NO: 27) and SAWL-FRMWY (SEQ ID NO: 28); WYNFDHNY (SEQ ID NO: 29), MWYNFDHN (SEQ ID NO: 30), RMWYNFDH (SEQ ID NO: 31), FRMWYNFD (SEQ ID NO: 32), LFRMWYNF (SEQ ID NO: 33), WLFRMWYN (SEQ ID NO: 34), and AWLFRMWY (SEQ ID NO: 35); WYNFDHN (SEQ ID NO: 36), MWYNFDH (SEQ ID NO: 37), RMWYNFD (SEQ ID NO: 38), FRMWYNF (SEQ ID NO: 39), LFRMWYN (SEQ ID NO: 40), and WLFRMWY (SEQ ID NO: 41); WYNFDH (SEQ ID NO: 42), MWYNFD (SEQ ID NO: 43), RMWYNF (SEQ ID NO: 44), FRMWYN (SEQ ID NO: 45), and LFRMWY (SEQ ID NO: 46); WYNFD (SEQ ID NO: 47), MWYNF (SEQ ID NO: 48), RMWYN (SEQ ID NO: 49), and FRMWY (SEQ ID NO: 50); WYNF (SEQ ID NO: 51), MWYN (SEQ ID NO: 52), and RMWY (SEQ ID NO: 53). It also includes the foregoing peptides wherein W$^{538}$Y$^{539}$ are unchanged, but where at least one (or at least two, at least three, at least four, at least five, at least six, at least seven or eight) of the other amino acids are replaced by conservative amino acids substitutions. In a specific embodiment, the peptide is 530-XXXXXXXXWYXXXXXXXX-547 (SEQ ID NO: 54), or a fragment of at least 4 (more specifically at least 5, 6, 7, 8, 9 or 10) consecutive amino acid thereof comprising including W$^{538}$Y$^{539}$, wherein each X corresponds to the amino acid at this position in native NHE6$^{530-547}$ peptide or any other amino acid that constitutes a conservative amino acid substitution as compared to the native amino acid at that position in NHE6$^{536-545}$ peptide. In a specific embodiment, the peptide is 536-XXWYXXXXXX-545 (SEQ ID NO: 55), or a fragment of at least 4 (more specifically at least 5, 6, 7, 8, 9 or 10) consecutive amino acid thereof comprising including W$^{538}$Y$^{539}$, wherein each X is as defined above.

A conservative amino acid substitution is defined herein as the substitution of an amino acid residue for another amino acid residue with similar chemical properties (e.g., size, charge, or polarity). Such a conservative amino acid substitution may be a basic, neutral, hydrophobic, or acidic amino acid for another of the same group (See e.g., Table I below). By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (He or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D). Certain amino acid residues are more likely to form a hydrogen bond such as Glutamine, Asparagine, Histidine, Serine Threonine, Tyrosine Cysteine, Methionine, Tryptophan, Aspartate, Glutamate, and Glycine.

TABLE I amino acid classification.

| Class | Name of the amino acids |
| --- | --- |
| Aliphatic | Glycine, Alanine, Valine, Leucine, Isoleucine |
| Hydroxyl or Sulfur/Selenium-containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their Amide | Aspartate, Glutamate, Asparagine, Glutamine |

Peptides of the present invention such as those listed above can be modified by known methods in the art including amidation of the terminal carboxyl group, substitution of one or more amino acids with synthetic amino acids, modification of one or more amino acids with saturated or unsaturated acyl chains ranging from 10 to 20 carbons ($C_{10}$-$C_{20}$), cyclization and rigidification of the secondary structure via lactam bridges, or PEGylation using PEG groups ranging from 2-20 kDa. These modifications result in peptides having higher potency, higher solubility, enhanced plasma half-life due to their resistance to proteases including DPPIV, increased peptide stability owing to resistance to oxidation, deamidation and other chemical changes that occur upon storage.

An illustrative amino acid sequence of human RACK1 is shown in FIG. 13D. Without being so limited NHE6-RACK1 blocking peptides include a peptide comprising at least 4 contiguous amino acids (more specifically at least 5, 6, 7, 8, 9 or 10) of the following RACK1 domain 186-TNHIGHTGYLNTVTVSPDGSLCASGGKDGQAMLW-DLNEG-224 (SEQ ID NO: 56) or at least 4 contiguous amino acids (specifically at least 5, 6, 7, 8, 9 or 10) of the following RACK1 domain 225-KHLYTLDGGDIINALCF SPNRYWLCAATGPSIKIWDLEGKIIVDEL-270 (SEQ ID NO: 57). RACK1 inhibitors further include Dequalinium-14; 1,1'-decamethylenebis-4-aminoquinaldinium diiodine (DECA), an inhibitor of RACK1 binding to protein kinase C (PMID: 16469071).

An illustrative amino acid sequence of human NHERF1 is shown in FIG. 13E. Useful NHE6-RACK1 blocking peptides according to the present invention include a peptide comprising at least at least 4 (specifically at least 5, 6, 7, 8, 9 or 10) comprising the 588-DSDL-591 (SEQ ID NO: 61) NHERF1 sequence or a peptide mimetic therefrom.

Useful antibodies according to the present invention include NHE6-RACK1 blocking antibodies and antibody fragments. Without being so limited, it includes antibodies that specifically bind to the cytoplasmic tail of NHE6 (e.g., the 527-588 fragment) and antibodies that specifically bind to RACK1 on its RACK1-NHE6 interaction domain.

Antibodies that specifically bind to either of the NHE6 cytoplasmic tail or to the RACK1-NHE6 interaction domain on RACK1 can be prepared by using epitopes present specifically in either of these proteins.

An epitope of a protein/polypeptide is defined as a fragment of said protein/polypeptide of at least about 4 or 5 amino acids in length, capable of eliciting a specific antibody and/or an immune cell (e.g., a T cell or B cell) bearing a receptor capable of specifically binding said epitope. Two different kinds of epitopes exist: linear epitopes and conformational epitopes. A linear epitope comprises a stretch of consecutive amino acids. A conformational epitope is typically formed by several stretches of consecutive amino acids that are folded in position and together form an epitope in a properly folded protein. An immunogenic fragment as used herein refers to either one, or both, of said types of epitopes. Without being so limited, epitopes in a sequence may be predicted with softwares such as BCPred™ AAP™ FBCPred™ and ABCPred™.

Methods for making antibodies are well known in the art. Polyclonal antibodies can be prepared by immunizing a suitable subject (e.g., rabbit, goat, mouse, or other mammal) with the polypeptide/protein of interest or a fragment thereof as an immunogen. A polypeptide/protein "fragment" "portion" or "segment" is a stretch of amino acid residues of at least about 5, 7, 10, 12, 14, 15, 20, 21 or more amino acids of the polypeptide noted above. The antibody titer in the immunized subject can be monitored over time by standard techniques, such as with an enzyme linked immunosorbent assay (ELISA) using immobilized exosomal marker polypeptide or a fragment thereof. At an appropriate time after immunization, e.g., when the antibody titers are highest, antibody-producing cells can be obtained from the animal, usually a mouse, and can be used to prepare monoclonal antibodies by standard techniques, such as the hybridoma technique originally described by Kohler and Milstein (1975) Nature 256: 495-497, the human B cell hybridoma technique (Kozbor et al. (1983) Immunol. Today 4: 72), the EBV-hybridoma technique (Cole et al. (1985) in Monoclonal Antibodies and Cancer Therapy, ed. Reisfeld and Sell (Alan R. Liss, Inc., New York, N.Y.), pp. 77-96) or trioma techniques. The technology for producing hybridomas is well known (see generally Coligan et al., eds. (1994) Current Protocols in Immunology, John Wiley & Sons, Inc., New York, N.Y.).

Alternatively, to preparing monoclonal antibody-secreting hybridomas, a monoclonal antibody can be identified and isolated by screening a recombinant combinatorial immunoglobulin library (e.g., an antibody phage display library) with a polypeptide or a fragment thereof to thereby isolate immunoglobulin library members that bind the polypeptide. Kits for generating and screening phage display libraries are commercially available (e.g., the Pharmacia Recombinant Phage Antibody System™, Catalog No. 27-9400-01; and the Stratagene SurfZAP™ Phage Display Kit, Catalog No. 240612).

Weak Base Chemotherapeutic Drugs

As used herein, the term "weak base chemotherapeutic drug" refers to a drug useful to treat cancer and that has a pKa between 7 and 10. Without being so limited, it includes free bases and salts of anthracyclines such as daunorubicin, doxorubicin, mitoxanthrone, epirubicin, idarubicin, and of vinca alkaloids such as vinblastine, vincristine, vindesine, vinorelbine, vincaminol, vineridine, vinburnine, vinpocetine, minovincine, methoxyminovincine, minovincinine, vincadifformine, desoxyvincaminol, vincamajine, and of tyrosine kinase inhibitor such as sunitinib and imatinib.

Compositions, Combination and Kits

Compositions

The present invention also relates to pharmaceutical compositions comprising the above-mentioned compounds of the invention, and in certain embodiments, weak base chemotherapeutic compounds.

Without being so limited, the medicaments/pharmaceutical compositions of the invention may be administered orally, for example in the form of tablets, coated tablets, dragees, hard or soft gelatin capsules, solutions, emulsions or suspensions. Administration can also be carried out rectally, for example using suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as ophthalmological preparations or an aerosol, for example in the form of a spray, such as a nasal spray.

For the preparation of tablets, coated tablets, dragees or hard gelatin capsules, the compounds of the present invention may be admixed with any known pharmaceutically inert, inorganic or organic excipient and/or carrier. Examples of suitable excipients/carriers include lactose, maize starch or derivatives thereof, talc or stearic acid or salts thereof.

Suitable excipients for use with soft gelatin capsules include for example vegetable oils, waxes, fats, semi-solid or liquid polyols etc. According to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, saline, alcohols, polyols, glycerin, vegetable oils and other appropriate excipients.

For suppositories, and local or percutaneous application, excipients which may be used include for example natural or hardened oils, waxes, fats and semi-solid or liquid polyols.

The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically active agents.

Intravenous, or oral administrations are preferred forms of use. The dosages in which the compounds of the invention are administered in effective amounts depend on the nature of the specific active ingredient, the age and the requirements of the patient and the mode of application.

As mentioned above, the pharmaceutical compositions of the invention can contain a pharmaceutically acceptable carrier including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

The compounds of the invention may be incorporated into dosage forms in conjunction with any of the vehicles which are commonly employed in pharmaceutical preparations, e.g., talc, gum arabic, lactose, starch, magnesium stearate, cocoa butter, aqueous or non-aqueous solvents, oils, paraffin derivatives or glycols. Emulsions such as those described in U.S. Pat. No. 5,434,183, incorporated herein by reference, may also be used in which vegetable oil (e.g., soybean oil or safflower oil), emulsifying agent (e.g., egg yolk phospholipid) and water are combined with glycerol. Methods for preparing appropriate formulations are well known in the art (see e.g., Remington's Pharmaceutical Sciences, 16th Ed., 1980, A. Oslo Ed., Easton, Pa. incorporated herein by reference).

In cases where parenteral administration is elected as the route of administration, preparations containing the compounds of the invention may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

It is a prerequisite that all adjuvants used in the manufacture of the preparations, such as carriers, are non-toxic and more generally pharmaceutically acceptable.

As used herein, "pharmaceutically acceptable" such as pharmaceutically acceptable carrier, excipient, etc., means pharmacologically acceptable and substantially non-toxic to the subject to which the particular compound is administered.

Any amount of a pharmaceutical composition can be administered to a subject. The dosages will depend on many factors including the mode of administration. Typically, the amount of the compound of the invention contained within a single dose will be an amount that effectively prevent, delay or treat the disease or condition to be treated, delayed or prevented without inducing significant toxicity.

The effective amount of the compounds of the invention may also be measured directly. The effective amount may be given daily or weekly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount may range from about 1 mg to about 25 grams of the composition per day, about 50 mg to about 10 grams of the composition per day, from about 100 mg to about 5 grams of the composition per day, about 1 gram of the composition per day, about 1 mg to about 25 grams of the composition per week, about 50 mg to about 10 grams of the composition per week, about 100 mg to about 5 grams of the composition every other day, and about 1 gram of the composition once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the pharmaceutical composition of the invention is given to the patient, but it is particularly advisable in such cases to begin with low doses to determine if adverse side effects are experienced.

Combinations and Kits

In another specific embodiment, the present invention provides a combination or a composition or a kit comprising (a) at least one of the compounds described herein (e.g., a NHE6-RACK1 blocker); and (b) (i) a weak base chemotherapeutic drug; (ii) at least one pharmaceutically acceptable carrier; or (iii) a combination or (i) and (ii).

In a specific embodiment of the kit, the kit comprises: (a) at least one of the compounds described herein (e.g., a NHE6-RACK1 blocker); and (b) (i) a weak base chemotherapeutic drug; (ii) at least one pharmaceutically acceptable carrier; (iii) instructions to use same in the prevention or treatment of cancer or of a symptom thereof; or (iv) a combination of at least two of (i) to (iii).

Methods

The present invention also provides methods for sensitizing tumor cells (e.g., hypoxic tumor cells) to weak base chemotherapeutic drugs and for potentiating the antitumoral activity of weak base chemotherapeutic drugs against tumors (e.g., hypoxic tumors). More particularly, the present invention relates to methods to decrease NHE6-Rack1 binding in tumor cells (e.g., hypoxic tumor cells); decrease NHE6 localization/mobilization on the plasma membrane of tumor cells (e.g., hypoxic tumor cells); increase localization or NHE6 in the endosomes of tumor cells (e.g., hypoxic tumor cells); decrease proportion of NHE6 localized on plasma membrane of tumor cells vs. NHE6 localized on endosome membranes of tumor cells (e.g., hypoxic tumor cells); increase the pH of endosome lumen/compartment of tumor cells (e.g., hypoxic tumor cells); decrease the pH of cytosol of tumor cells (e.g., hypoxic tumor cells); decrease the pH gradient between the endosome lumen/compartment and cytosol of tumor cells (e.g., hypoxic tumor cells); decrease weak base chemotherapeutic drug concentration/capture/sequestration in tumor cells (e.g., hypoxic tumor cells) endosomes; increase cytosol and/or nuclear concentration of weak base chemotherapeutic drugs in tumor cells (e.g., hypoxic tumor cells); prevent, decrease or reverse resistance (increase sensitivity) of tumor cells (e.g., hypoxic tumor cells) against weak base chemotherapeutic drugs; and/or increase antitumoral activity of weak base chemotherapeutic against tumor cells (e.g., hypoxic tumor cells), comprising the administration of at least one of the compounds described herein (e.g., a NHE6-RACK1 blocker) to a tumor cell/subject in need thereof (a subject having cancer).

In a specific embodiment, the present invention provides a method for sensitizing a subject's tumor cells (e.g., hypoxic tumor cells) to the antitumoral activity of a weak base chemotherapeutic drug comprising the administration of a NHE6-RACK1 blocker compound to the subject. As used herein the term "sensitizing" a subject's tumor cells to the antitumoral activity of a weak base chemotherapeutic drug refers to an increase in antitumoral activity of a fixed amount of the drug prior vs. after sensitization and/or a decrease in the amount of the drug prior vs. after sensitization to achieve a fixed antitumoral activity (see e.g., Examples 7 and 11).

In another specific embodiment, the present invention provides a method for preventing or treating a cancer or a symptom thereof in a subject comprising the administration of a NHE6-RACK1 blocker compound in combination (simultaneously to sequentially) with a weak base chemotherapeutic drug to the subject.

Hypoxic cells are cells related to metastasis and cancer recurrence[9,65].

Treatment and Prevention

The terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/reduction in the severity of a human disease (e.g., a reduction or inhibition of cancer progression and/or metastasis development), a decrease/reduction in at least one symptom or disease-related effect (e.g., decrease in number or size of tumor, decrease in metastasis), an amelioration of at least one symptom or disease-related effect, a decrease/reduction of the development of the cancer resistance to a drug treatment, and an increased survival time of the affected host animal, following administration of the at least one compound of the present invention, or of a composition comprising the compound, in combination with a weak base chemotherapeutic drug. In accordance with the invention, a prophylactic effect may comprise a complete or partial avoidance/inhibition of cancer or a delay of cancer (e.g., a complete or partial avoidance/inhibition of metastasis development or a delay of metastasis development), of drug resistance, and an increased survival time of the affected host animal, following administration of the at least one compound of the present invention, or of a composition comprising the compound, in combination with a weak base chemotherapeutic drug.

A "therapeutically effective amount" or "effective amount" or "therapeutically effective dosage" of a compound of the present invention, or of a composition comprising the compound, in combination with a weak base chemotherapeutic drug thereof can result in the treatment or prevention of cancer or a symptom thereof.

As used herein the term "cancer or a symptom thereof" in the context of the present invention refers to any cancer treatable by a weak base chemotherapeutic drug.

As used herein the term "subject" is meant to refer to any animal, such as a mammal including human, mice, rat, dog, cat, pig, cow, monkey, horse, etc. In a particular embodiment, it refers to a human.

A "subject in need thereof" or a "patient" in the context of the present invention is intended to include any subject that will benefit or that is likely to benefit from the compounds of the present invention. In an embodiment, the subject in need thereof is a subject diagnosed as having cancer (e.g., comprising weak base chemotherapeutic drug resistant tumors).

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

Although the present invention has been described hereinabove by way of specific embodiments thereof, it can be modified, without departing from the spirit and nature of the subject invention as defined in the appended claims.

The present invention is illustrated in further details by the following non-limiting examples.

Example 1: Material and Methods

Antibodies and Reagents

Antibodies used for IF microscopy or Western-blotting were obtained from commercial sources. The following antibodies were used: rabbit anti-NHE6 (Abcam 137185), rabbit anti-NHE9 (Abcam 167157), mouse anti-RACK1 (BD Biosciences 610177), rabbit anti-RACK1 (Cell Signaling Technology 5432), mouse anti-tubulin (Sigma-Aldrich T6199), rabbit anti-actin (Sigma-Aldrich A5060), mouse monoclonal anti-HA (BioLegend MMS-101P), mouse anti-EEA1 (Santa Cruz Biotechnology 6415), mouse anti-Rab7 (Santa Cruz Biotechnology 10767), rabbit phospho-(Ser) PKC substrate (Cell Signaling Technology 2261), mouse monoclonal PKC (Santa Cruz Biotechnology 80), mouse monoclonal anti-LAMP2 (Abcam 25631), rabbit anti-P-glycoprotein (Abcam 129450). All Alexa Fluor secondary antibodies were acquired from Thermo Fisher Scientific. 4',6-diamidino-2-phenylindol dilactate (DAPI), Alexa Fluor-conjugated transferrin and Lysotracker® were purchased from Thermo Fisher Scientific. Chemotherapeutic drugs (Doxorubicin, Mitoxantrone, Daunorubicin) were obtained from the local drug dispensary of the Centre Hospitalier Universitaire de Sherbrooke (CHUS). Chloroquine and bafilomycin A1 were obtained from Sigma Aldrich. Chloroquine was dissolved in water and bafilomycin A1 in DMSO. Control shRNA and shRNA directed against human NHE6 or NHE9 were purchased from Sigma-Aldrich. RNAi directed against RACK1 was purchased from Ambion.

Cell Culture Under Hypoxic Conditions

HT1080 fibrosarcoma cells (ATCC) were cultured in Eagle's minimum essential medium and MDA-MB-231 breast cancer cells (ATCC) were cultured in Dulbecco's modified essential medium. Culture media were supplemented with 10% heat-inactivated FBS and 40 µg/ml gentamycin. Cells were cultured in a humidified atmosphere at 37° C. with 5% $CO_2$ and 21% $O_2$. For incubation under hypoxic conditions, cells were placed in an In Vivo$_2$ 400 hypoxia Workstation™ (Ruskinn) under a humidified atmosphere of 1% $O_2$ and 5% $CO_2$. All cell lines were routinely tested for *mycoplasma* using the MycoSEQ™ *mycoplasma* detection kit (Thermo Fisher Scientific).

Plasmid Construction and Transfection in Human Cell Lines peGFP-N3-NHE6 was generously provided by Hiroshi Kanazawa (Osaka University, Japan). pcDNA3-HA/NHE6 was constructed from peGFP-N3-NHE6. For this, the entire NHE6 coding sequence was excised with BamHI and EcoRI restriction enzymes and cloned in pcDNA3-HA vector. pcDNA3-HA/NHE6$^{527-588}$ was designed from pcDNA3-HA/NHE6 using the following primers:

```
forward
                                         (SEQ ID NO: 58)
5'-ATGCGGATCCACCAAAGCAGAGAGTGCTTG-3'.

reverse
                                         (SEQ ID NO: 59)
5' GCATGAATTCTTAATCATCATCTTTCAACTGTT-3'.
```

HT-1080 cells were stably transfected with Polyethylenimine (PEI, MirusBio) and positive cells were selected with Geneticin™ (G418) at 400 µg/mL. In the case of MDA-MB-231 cells, plasmids were transfected using Lipofectamine™ 2000 (Sigma-Aldrich) and G418 was added to cell cultures at a concentration of 2 mg/mL.

Lentiviruses and cell transduction pLKO.1-NHE6 and pLKO.1-NHE9 shRNA (Sigma-Aldrich) were co-transfected with ViraPower™ Lentiviral Packaging Mix (Invitrogen) into HEK293T cells according to manufacturer's instructions. Viruses were collected and concentrated by ultracentrifugation 72 h after transfection. HT-1080 and MDA-MB-231 cells were infected overnight with viruses and selected with puromycin (2 µg/ml) on the third day following transduction.

Cell Viability Assay

Cells ($5 \times 10^3$) were cultured in 96-well plates and pre-incubated under 21% $O_2$ or 1% $O_2$ for 4 h following the addition of drugs for 72 h. Cell viability was measured using the 3-(4,5-dimethylthiazol-2-yl)-2,5-diphenyltetrazolium bromide (MTT) dye (Life Technologies) according to manufacturer's instructions. Because hypoxic conditions may affect the reduction of MTT to formazan, incubation of all cell cultures with MTT were performed under normoxic conditions. Each experiment was performed in triplicate and at least three independent experiments were performed. Log-scale dose-response data were plotted on a graph and a three-parameter non-linear regression was applied to determine $IC_{50}$ values. For calculation of the $IC_{50s}$, both normoxic and hypoxic drug-treated samples were normalized with their untreated counterpart.

Cell viability was also assessed by the trypan blue exclusion method. Briefly, cells were grown to 80% confluency, trypsinized, and plated in triplicate into 6-well plates. Cells were incubated for 24 h following drug treatment. Cells were harvested and equal amount of freshly prepared trypan blue solution was added to the cell suspension. Viable cells were counted with a haemocytometer and the experiment was repeated at least three times. The percentage of viable cells was determined relative to the number of control cells.

Intracellular Localization of Dox and Live-Cell Imaging

Cells were cultured in 25 mm-diameter glass coverslips (Thermo Fisher Scientific) and incubated under various conditions (as indicated in the FIG. legends). Cells were then incubated for 2 h in a medium containing Dox (2 µM). After the incubation period, cells were washed to remove excess Dox and left in drug-free media for 10 min. In selected samples, Alexa Fluor 633-conjugated transferrin (25 µg/ml) was added to the cells and incubated for 20 min in order to label endosomes. Coverslips were mounted on glass slides and placed on a 37° C. warmed stage of an Olympus Fluoview™ FV1000 (Olympus, Tokyo, Japan) confocal laser scanning microscope. Dox was excited with a green helium neon laser (543 nm) and emitted fluorescence intensity was measured. Images were acquired on the same day, typically from 10-20 cells of similar size from each experimental condition, using identical instrument settings.

Intracellular pH Measurement by Confocal Microscopy

The pH sensing ratiometric dyes SNARF-1 and HPTS (Life Technologies) were used simultaneously for pH measurement of both cytoplasmic (C-SNARF-1) and endosomal/lysosomal (HPTS) compartments as previously described[30]. Briefly, cells were cultured in 35 mm petri dishes (BD Biosciences) and used at 50% confluence. For endocytic labeling, cells were incubated overnight with HPTS (1 mM), washed, followed by a 20-min incubation with SNARF-1 (5 µM) to label the cytoplasmic compartment. Living cells were analyzed using an Olympus Fluoview™ FV1000 confocal microscope. Fluorescence emissions of both pH-sensing probes were recorded and subsequently analyzed as described[30].

Cell-Surface Biotinylation

Biotinylation steps were performed at 37° C. Cells were grown on circular 15-mm diameter glass coverslips (Thermo Fisher Scientific) and incubated at 21% or 1% $O_2$. Cells were then washed with PBS containing 1 mM $CaCl_2$ and 0.5 mM $MgCl_2$ (PBSCM) and incubated for 5 min with 0.3 mg/ml of EZ-Link Sulfo-NHS-SS-Biotin (Pierce) in PBSCM. Unreacted biotin was quenched using 100 mM glycine. Cells were fixed for 10 min at room temperature using 1% PFA in PBS. Prior to staining, cells were blocked with 5% of BSA for 1 h at room temperature. Biotinylated cells were stained with 5 µg/ml Streptavidin Texas Red (Invitrogen) for 1 h at 4° C. Coverslips were washed and mounted on a microscope slide using Vectashield mounting media (Vector labs).

Immunofluorescence

Cultured cells were fixed with 1% PFA for 10 min at room temperature, permeabilized with saponin (0.05% in PBS) for 20 min, and blocked with 2% BSA in PBS for 30 min. Cells were then incubated with the appropriate primary and secondary antibodies as follows: anti-EEA1 (1/500), anti-Rab7 (1/500) and fluorophore-conjugated secondary antibodies (1/1000). Images were recorded using an Olympus Fluoview™ FV1000 confocal microscope using a 63× oil immersion objective.

Immunoprecipitation and Western-Blotting

Cells were lysed on ice in NP-40-containing buffer (50 mM Tris-HCl pH 8.0, 150 mM NaCl, 1% NP-40, 5 mM EDTA, phosphatase and protease inhibitors). Cell lysates were centrifuged at 13,000 rpm at 4° C. and protein concentration determined using the BCA protein assay (Thermo Fisher Scientific). After a pre-clearing step with protein A/G-agarose beads (GE Healthcare), protein complexes were immunoprecipitated overnight at 4° C. Samples were incubated in SDS-loading buffer for 30 minutes at room temperature to avoid transmembrane protein aggregates upon heating in a boiling water bath. Proteins were separated by SDS-PAGE electrophoresis, transferred to a PVDF membrane and immunoblotting was performed as described, using anti-NHE6 (1:1000), anti-NHE9 (1:1000) anti-RACK1 (1:2000), anti-tubulin (1:5000), anti-actin (1:5000) anti-HA (1:1000), anti-PKC (1:200), anti-phospho PKC substrate (1:1000), anti-LAMP2 (1:200), anti-P-glycoprotein (1:200) and HRP-conjugated secondary antibodies (1/10 000)[66].

RNA Isolation and Quantitative PCR Analysis

Total cellular RNA was isolated using the TRI-Reagent protocol (Invitrogen) according to the supplier's protocol. Quantitative real time PCR was performed using the SYBR Green qPCR Mastermix™ (Biotool) and a Rotor-Gene™ 3000 instrument (Corbett Research). Each reaction was run in duplicates and values were normalized against the RPLPO housekeeping gene. Double delta Ct method was used to determine relative gene expression: $\Delta\Delta Ct = (Ct_{treated} - Ct_{untreated})_{gene\ of\ interest} - (Ct_{treated} - Ct_{untreated})_{housekeeping\ gene}$. Fold changes were calculated using the equation: expression fold change=$2^{-\Delta\Delta Ct}$.

Chorioallantoic Membrane Assay

Fertilized eggs from white leghorn chicken were obtained from Public Health Agency of Canada (Nepean, ON). Ethics approval was obtained from the Ethics Committee on Animal Research of the University of Sherbrooke and all experimental procedures involving embryos were conducted in accordance with the regulations of the Canadian Council on Animal Care. Eggs were incubated in an Ova-Easy egg incubator (Brinsea) at 37° C. with 60% humidity. At Day 3, eggs were cracked as described[67]. At Day 9, HT-1080 and MDA-MB-231 cell suspensions ($1 \times 10^6$ and $2 \times 10^6$ cells, respectively) were mixed (1:1) with growth factor reduced Matrigel (BD Biosciences) in a total volume of 20 µl. Cell grafts were placed on top of the CAM and eggs were returned to the incubator for 96 h until Day 13 (n>6 chick embryos per cell line). When mentioned, 50 µl of Dox were added topically to the formed tumors (Day 13 after tumor cell grafting). At Day 16, chick embryos were euthanatized by decapitation. Tumors were removed and tumor volumes were calculated using the formula: ($Dd^2/3$). For RNA quantification, tumors were immediately snap-frozen in liquid nitrogen and kept at −80° C. until RNA extraction using the Trizol reagent.

Immunohistochemistry

Tumor hypoxia was determined by i.v. injection of 4 mg pimonidazole hydrochloride (Hydroxyprobe, Hypoxyprobe™-1 Kit) in 50 µL solution 30 minutes before tumor harvest. Tumors removed from CAM were placed directly in the cryopreservative embedding media OCT compound (Tissue Tek) and immediately frozen in a mixture of isopentane and carbonic ice. Sections of 5 µm thickness were fixed with PFA 4% 10 minutes at 4° C. Blocking and staining were performed in BSA 2%, 0.2% Triton X-100 and supplemented with 10% of goat serum. Tumors sections were double-stained for pimonidazole in combination with CAIX (1/50). Pimonidazole was detected with mouse antibody (Hypoxyprobe, 1:200) and goat anti-mouse IgGγ1-Alexa 488 (Invitrogen).

Statistical Analysis

GraphPad™ software was used for statistical analysis. Paired or unpaired Student's t-test were used to assess statistical significance, which was set at p-value<0.05.

Data Availability

All data generated or analyzed during this study are included in this published article (and its supplementary information files).

Example 2: Hypoxia Induces PH-Dependent Dox Resistance

To assess the role of pH in hypoxia-induced resistance to anthracyclines, the human breast cancer MDA-MB-231 and fibrosarcoma HT-1080 cell lines were incubated in the presence or absence of the commonly used anthracycline drugs, doxorubicin (Dox), daunorubicin (Dau) and the anthracycline analog drug, mitoxantrone (Mtx), under hypoxic (1% $O_2$) or normoxic (21% $O_2$) conditions for 72 hours. Cell viability was then assessed using the MTT assay. The impact of extracellular pH on Dox uptake by HT-1080 was also assessed.

Incubation of HT-1080 cells in media of different pHs indicates that extracellular acidification reduces the uptake of Dox as observed by the decrease in doxorubicin fluorescence intensity in the nucleus (FIG. 1A).

In HT-1080 cells cells, hypoxia increased resistance toward the chemotherapeutic drugs by 5.5-, 5.0- and 4.7-fold for Dox, Mtx and Dau, respectively (Table II). Similar changes in cell viability were observed in MDA-MB-231 (Table II). By their biochemical properties, anthracyclines and their analogs are sensitive to pH and are preferentially localized in acidic environments[28][17]. To assess whether pH alterations would affect hypoxia-induced resistance, the vacuolar pH alkalizing drug chloroquine (Cq) and the vacuolar (V)-ATPase inhibitor, bafilomycin A1 (Baf) were used in the presence of the model anthracycline drug, Dox, in viability assays. Treatment of MDA-MB-231 and HT-1080 cells with vacuolar pH neutralizing agents prevented drug resistance induced by hypoxia with effective concentration values similar to those observed under normoxic conditions (Table III and FIGS. 1 B-G). These results were confirmed using direct cell counting of viable cells using the trypan blue exclusion method (FIGS. 1H-K). Therefore, hypoxia promotes cell resistance to anthracycline drugs that can be prevented by pH neutralization.

Data are presented at the mean (nM)+/− standard deviation. Fold change was calculated as the drug $IC_{50}$ of cells exposed to 1% $O_2$ to the $IC_{50}$ of cells exposed to 21% $O_2$. $IC_{50}$, half maximal inhibitory concentration; Dox: doxorubicin, Baf, bafilomycin; Cq, chloroquine (n=3-5 independent experiments with 3 replicates in each experiment). P-values were determined with unpaired t-test with Welch's correction.

Example 3: Hypoxia Promotes Dox Sequestration within Endosomes

Figure 2A:
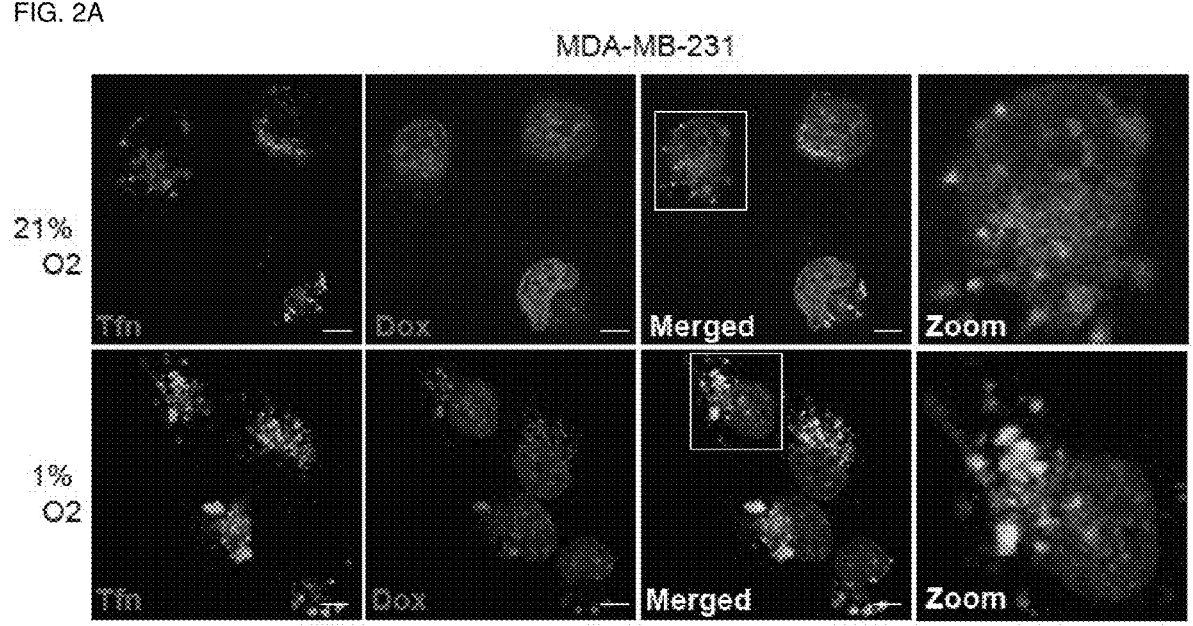
FIGS. 2A-J. Hypoxia triggers Dox sequestration within endosomal compartments.
Figure 2B:
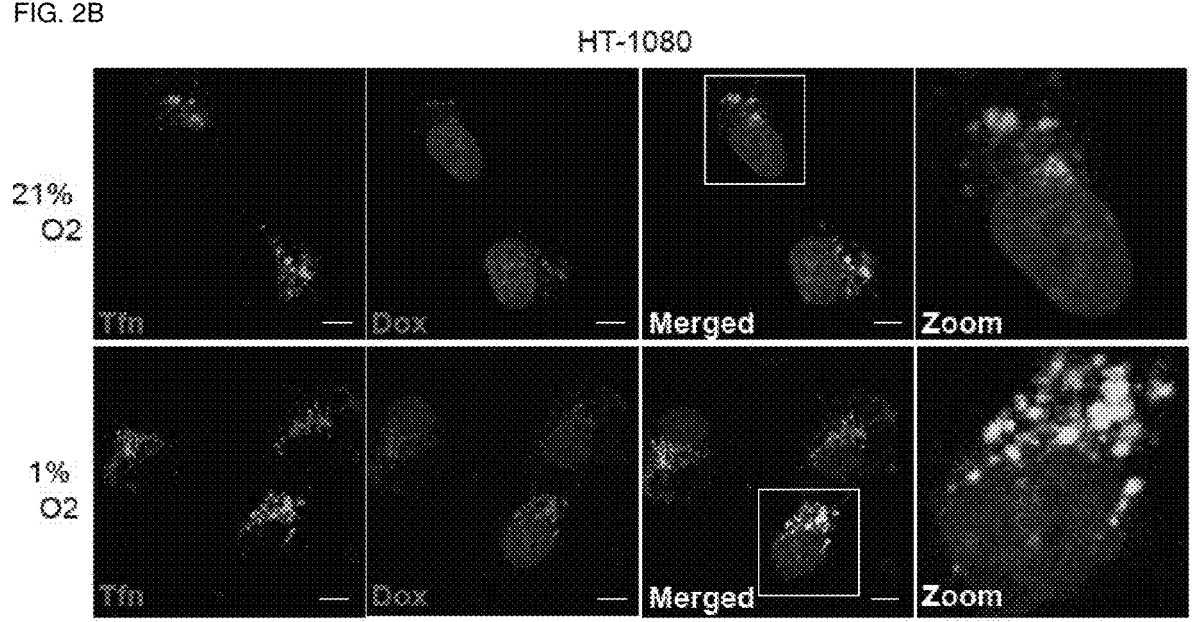
Figure 2C:
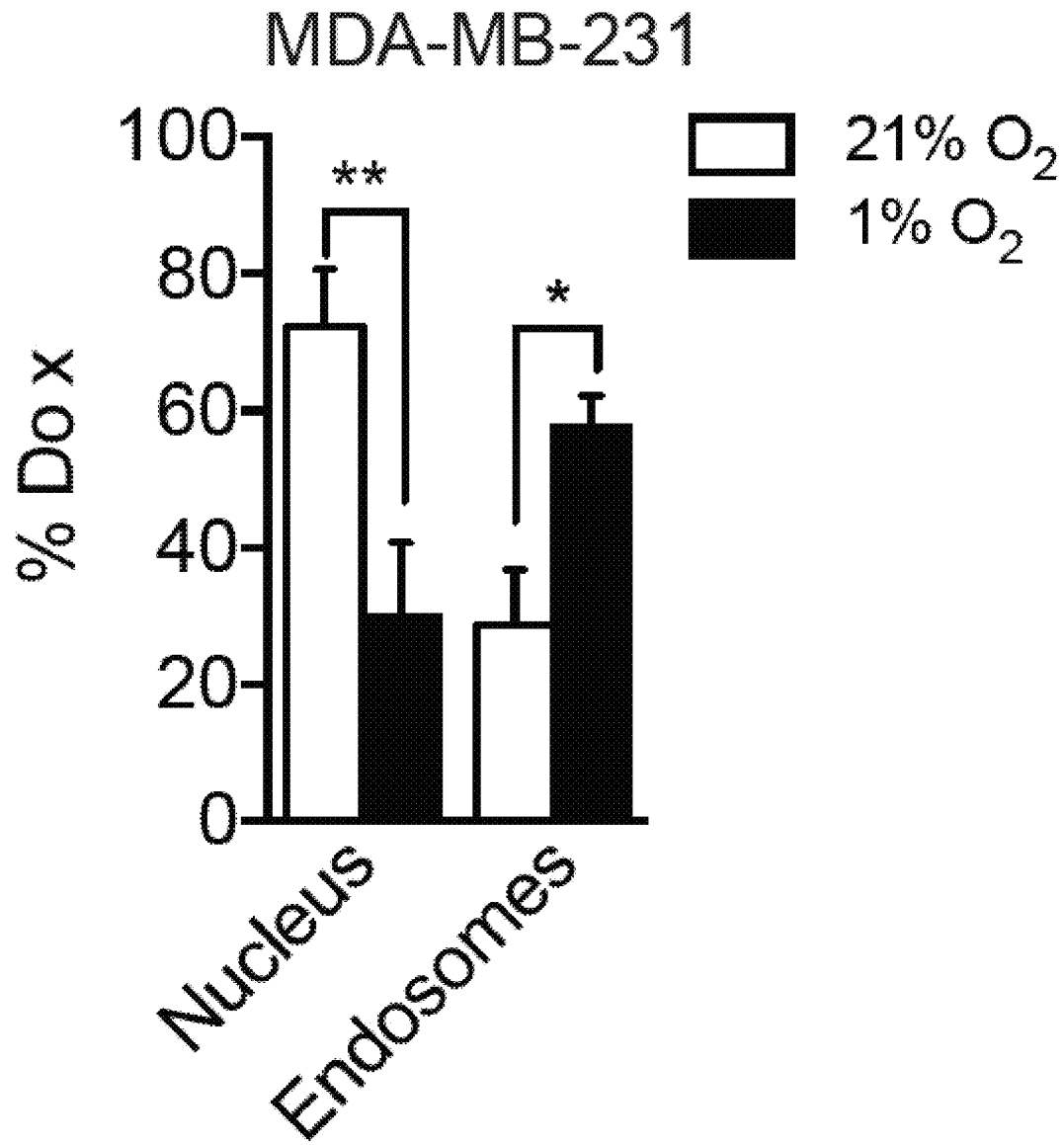
Figure 2D:
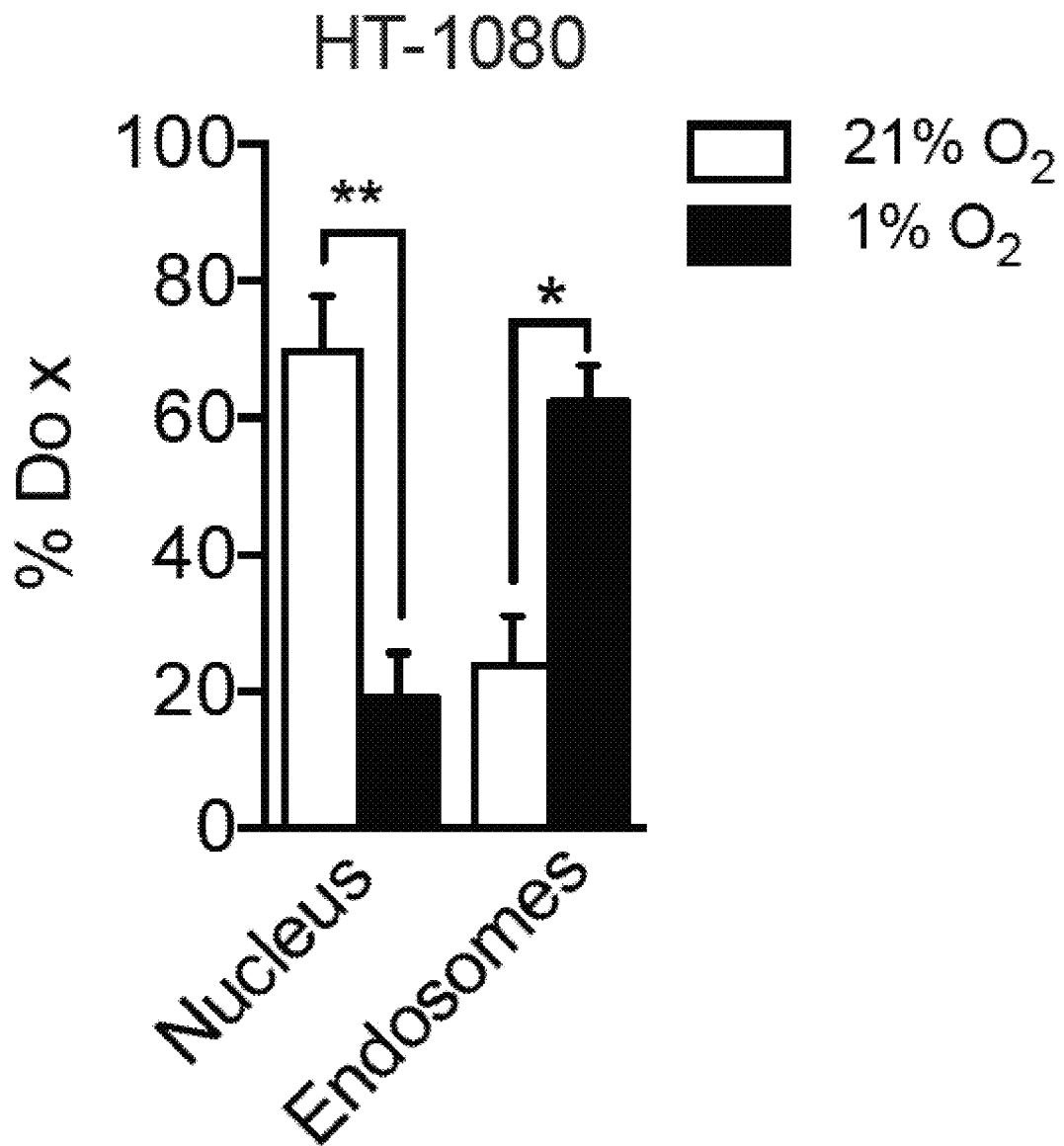

Given the resensitizing impact of pH neutralizers on hypoxia-induced Dox resistance and the fact that intracellular anthracyclines distribution was shown to depend on pH gradients[29], the influence of hypoxia on cellular distribution of Dox was assessed. The inventors took advantage of the native red fluorescence property of Dox that allows monitoring of drug partitioning by fluorescence confocal microscopy in living cells. Consistent with the fact that anthracyclines target topoisomerase II, they observed a predominant accumulation of Dox in the nucleus of normoxic MDA-MB-231 or HT-1080 cells (FIGS. 2A-B). When cells were incubated under hypoxic conditions, Dox localization in the nucleus was significantly decreased whereas fluorescence was increased within perinuclear vesicles. Co-staining with Alexa[488]-conjugated transferrin indicated that a large proportion of these vesicles corresponded to early and recycling endosomes (FIGS. 2A-D). The increase in intravesicular

TABLE II $IC_{50}$ values of anthracyclines for cancer cell lines in normoxia or hypoxia.

| | Cell line | | | | | | | |
|---|---|---|---|---|---|---|---|---|
| | MDA-MB-231 | | | | HT-1080 | | | |
| Treatment | 21% $O_2$ | 1% $O_2$ | Fold change | p-value | 21% $O_2$ | 1% $O_2$ | Fold change | p-value |
| Dox | 125.3 +/− 2.7 | 688.1 +/− 28.4 | 5.5 | <0.0001 | 73.4 +/− 3.9 | 301.2 +/− 30.9 | 4.1 | <0.0001 |
| Mtx | 151.7 +/− 9.4 | 752.2 +/− 37.5 | 5.0 | <0.0001 | 93.5 +/− 7.6 | 451.2 +/− 23.8 | 4.9 | <0.0001 |
| Dau | 198.8 +/− 4.8 | 921.3 +/− 69.3 | 4.7 | 0.029 | 101.9 +/− 30.5 | 813.8 +/− 29.3 | 8.1 | <0.0001 |

Data are presented as the mean (nM)+/− standard deviation. Fold change was calculated as the drug $IC_{50}$ of cells exposed to 1% $O_2$ to the $IC_{50}$ of cells exposed to 21% $O_2$. $IC_{50}$, half maximal inhibitory concentration; Dox, doxorubicin; Mtx, mitoxantrone; Dau, daunorubicin (n=3-5 independent experiments with 3 replicates in each experiment). P-values were determined using unpaired t-test with Welch correction.

Dox localisation was not associated with an increase in total number of endosomes or lysosomes per cell (FIGS. 2 E-F). Incubation of the cells in presence of the pH neutralizing agents (Cq and Baf) abolished hypoxia-induced Dox sequestration within endosomes and restored the preferential accumulation of the drug in the nucleus (FIGS. 2G-J). The inventors concluded that hypoxia-induced resistance to Dox

TABLE III $IC_{50}$ values of doxorubicin for cancer cell lines treated with neutralizing agents in normoxia or hypoxia.

| | Cell line | | | | | | | |
|---|---|---|---|---|---|---|---|---|
| | MDA-MB-231 | | | | HT-1080 | | | |
| Treatment | 21% $O_2$ | 1% $O_2$ | Fold change | p-value | 21% $O_2$ | 1% $O_2$ | Fold change | p-value |
| Dox | 167.7 +/− 30.4 | 852.3 +/− 42.7 | 5.1 | <0.0001 | 113.4 +/− 11.9 | 447.7 +/− 22.1 | 4.0 | <0.0001 |
| Dox + Baf (100 nM) | 188.1 +/− 17.7 | 86.9 +/− 2.9 | −0.4 | 0.0012 | 40.8 +/− 3.1 | 73.5 +/− 12.9 | 1.8 | 0.042 |
| Dox + Cq (10 µM) | 46.7 +/− 7.2 | 51.4 +/− 4.4 | 1.1 | 0.317 | 102.4 +/− 8.7 | 97.3 +/− 9.2 | −0.9 | 0.52 | is related to drug sequestration within endosomal/recycling vesicles in a pH-dependent manner.

Example 4: Dox Sequestration is Linked to Endosome Hyperacidification

Figure 2E:
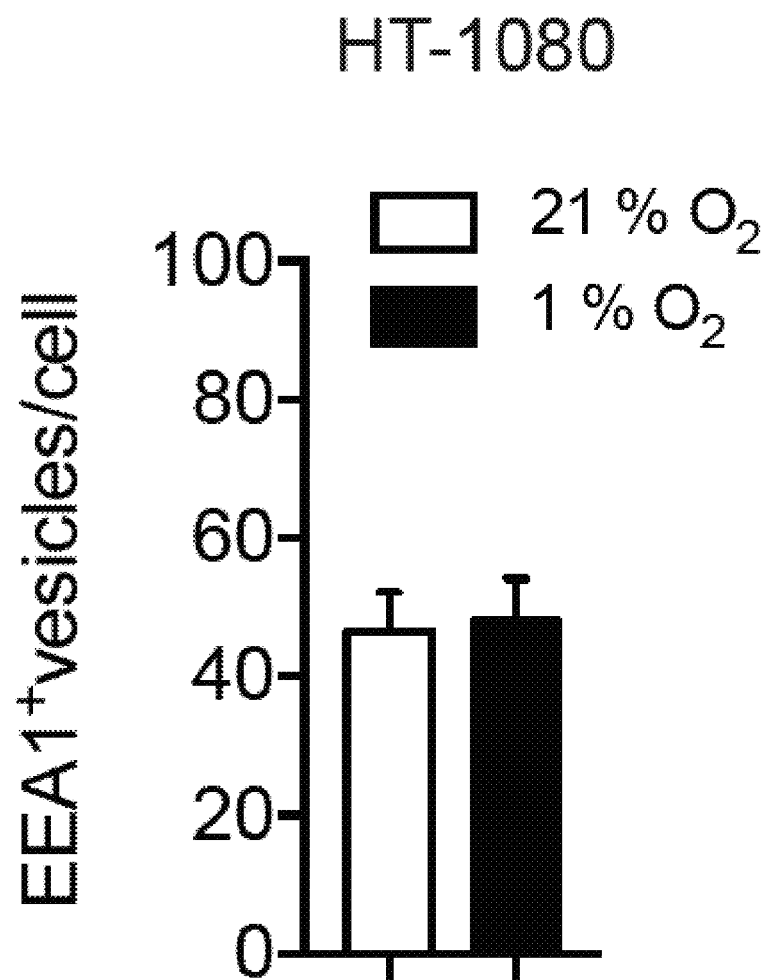
Figure 2F:
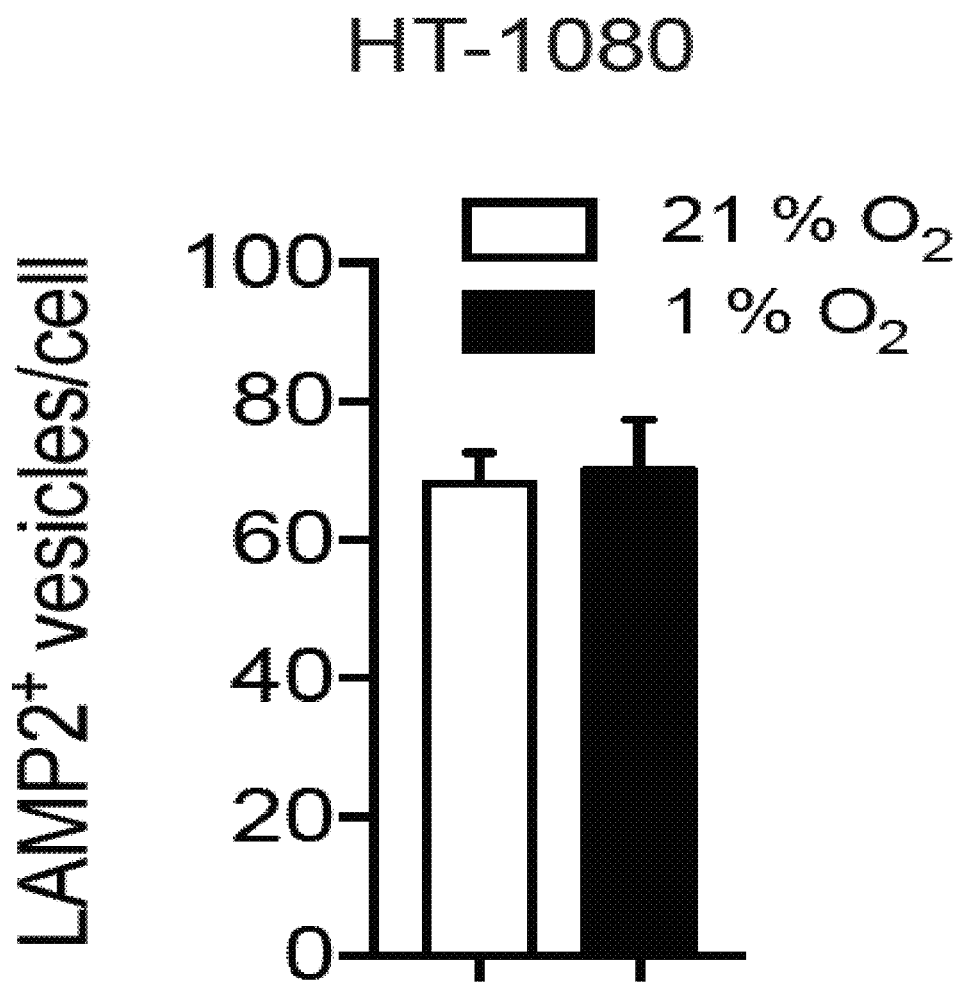
Figure 2G:
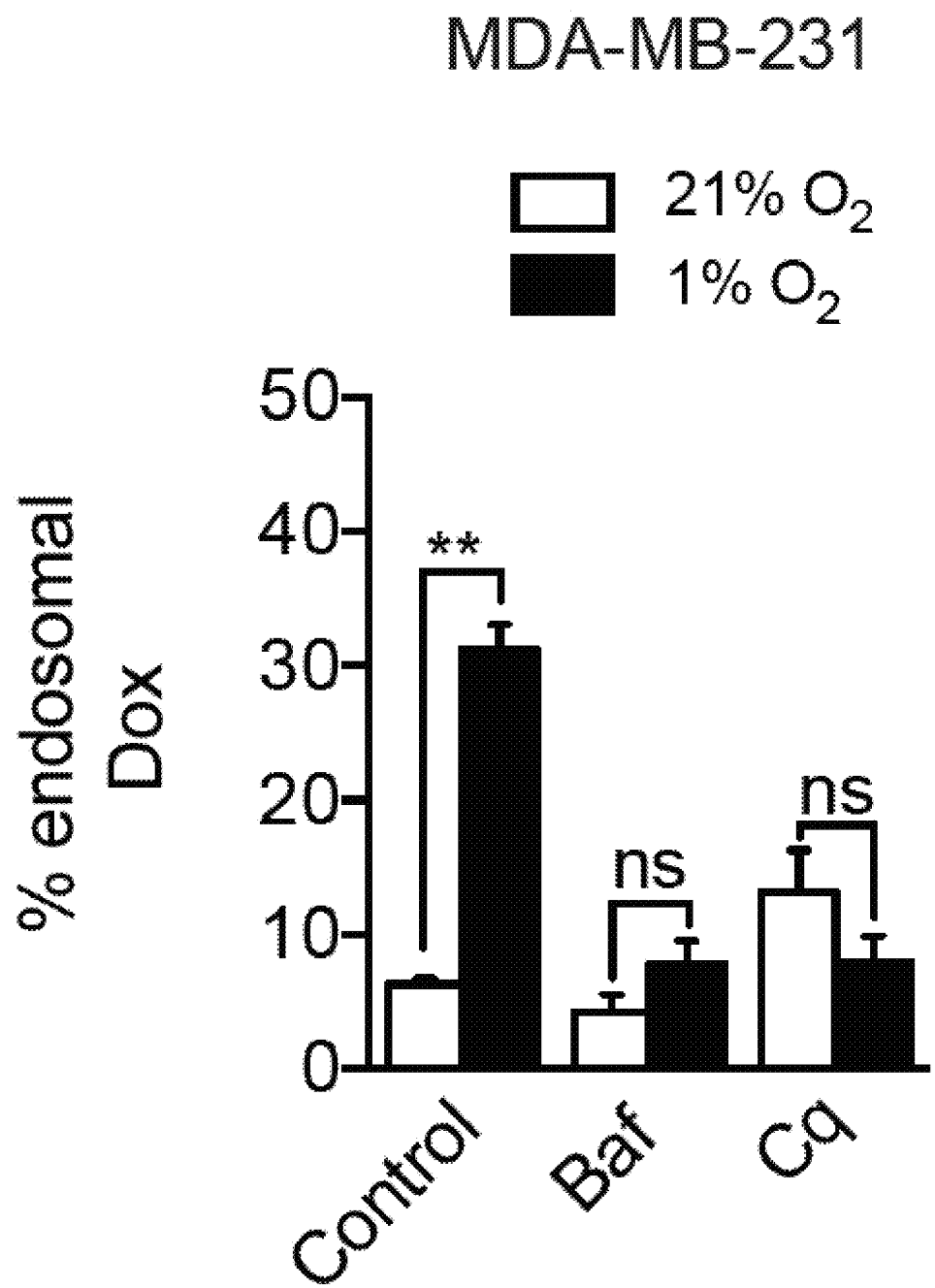
Figure 2H:
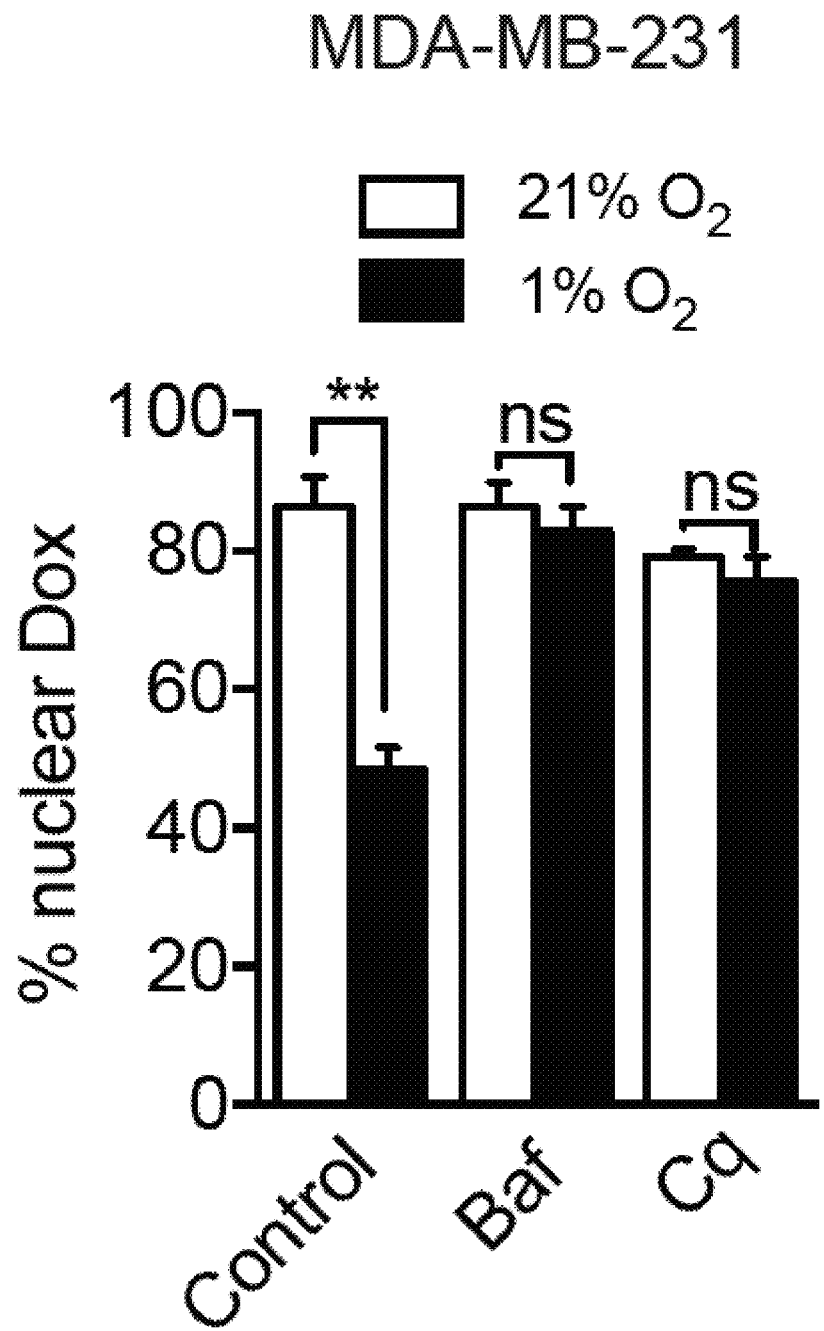
Figure 2I:
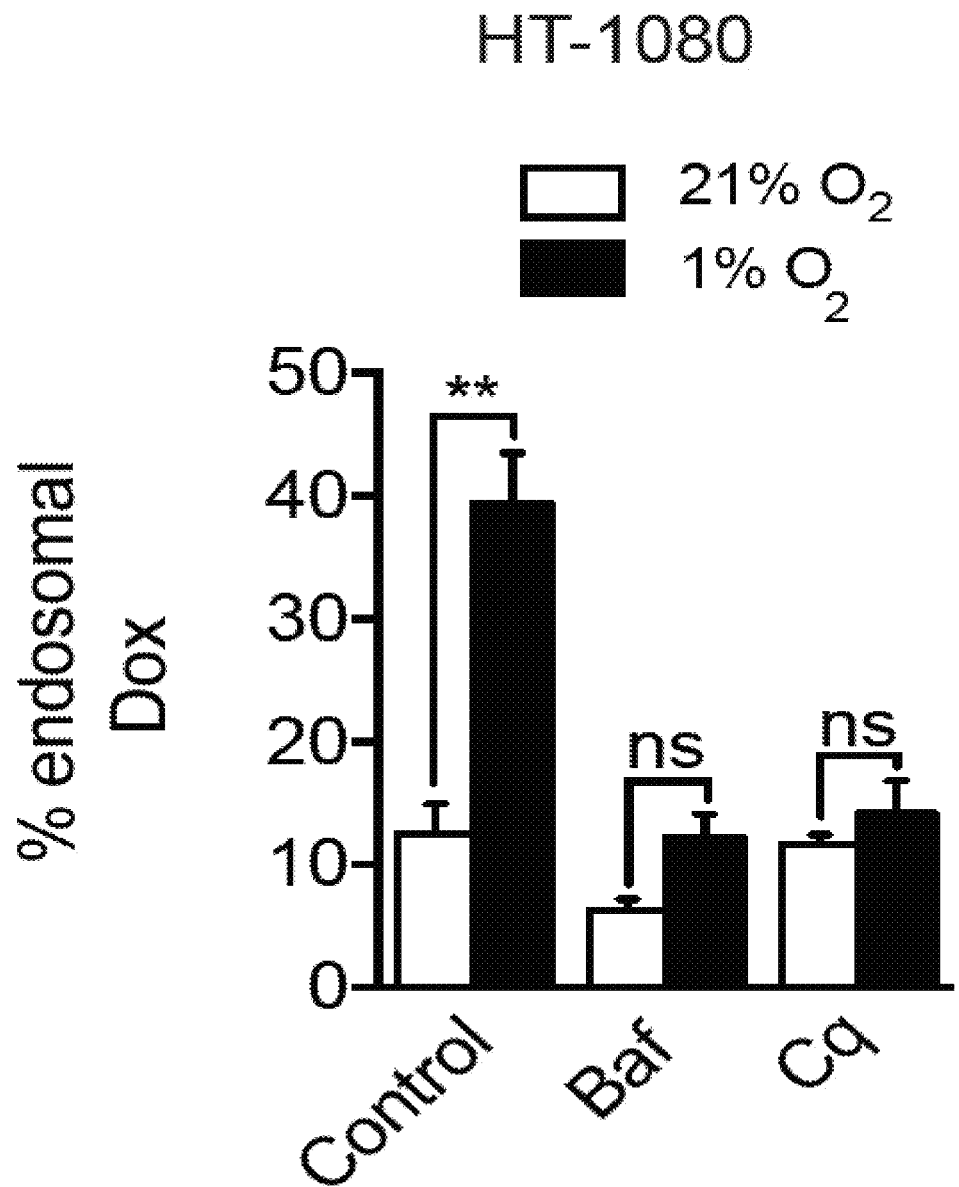
Figure 2J:
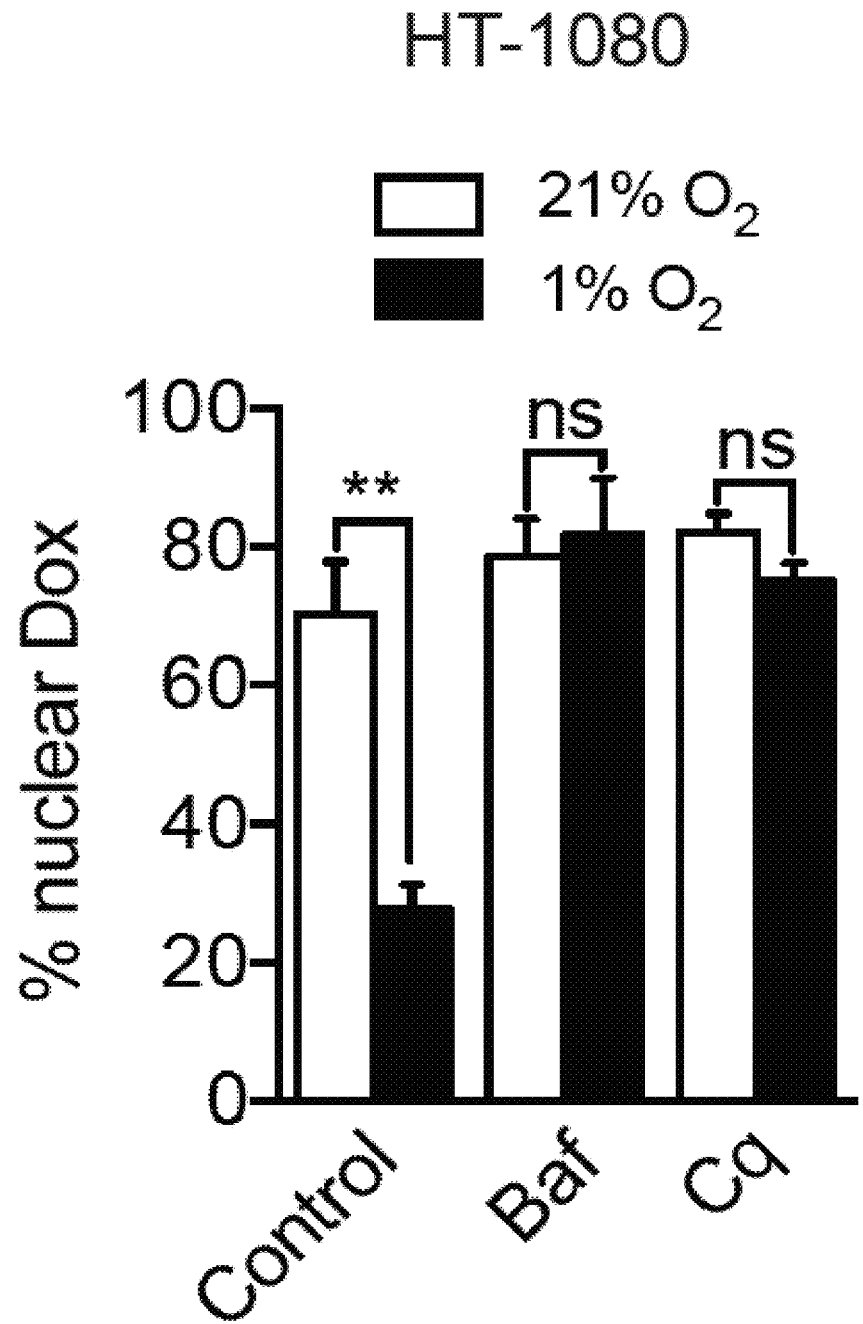
Figure 3A:
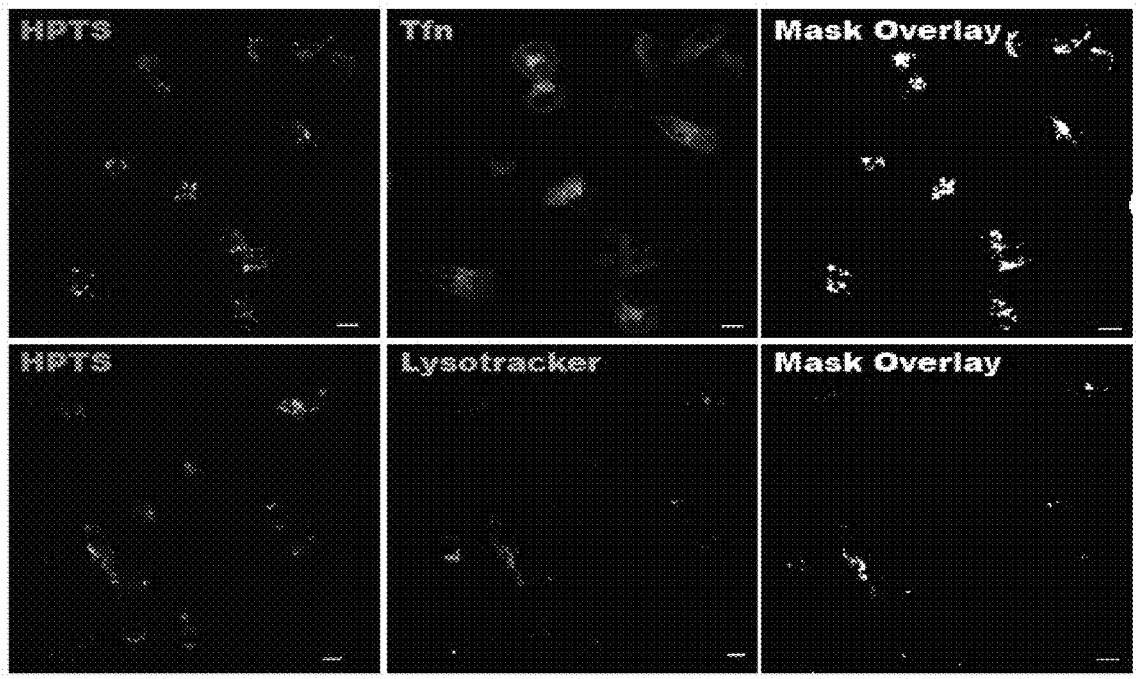
FIGS. 3A-L. Hypoxia promotes endosome hyperacidification.
Figure 3B:
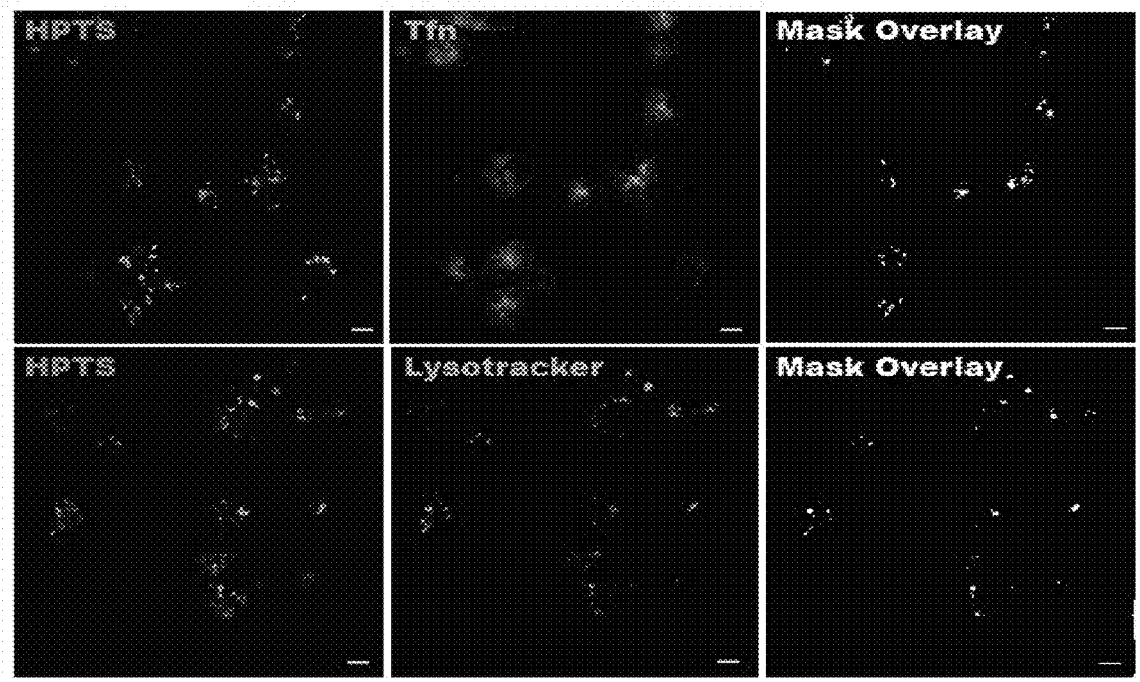
Figure 3C:
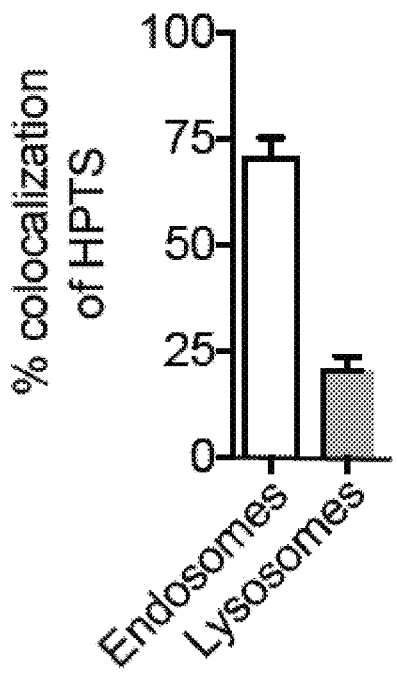
Figure 3D:
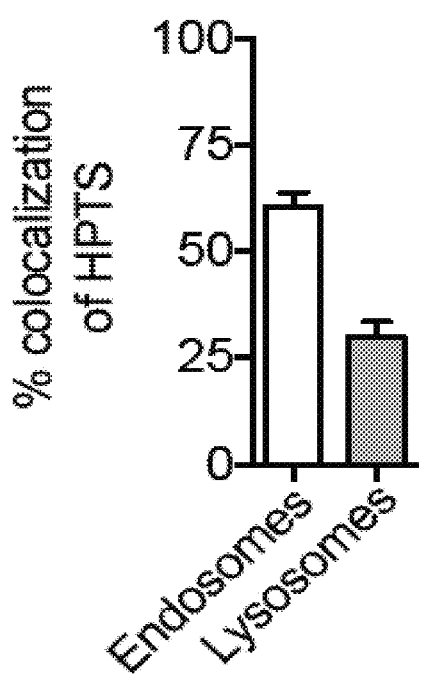
Figure 3E:
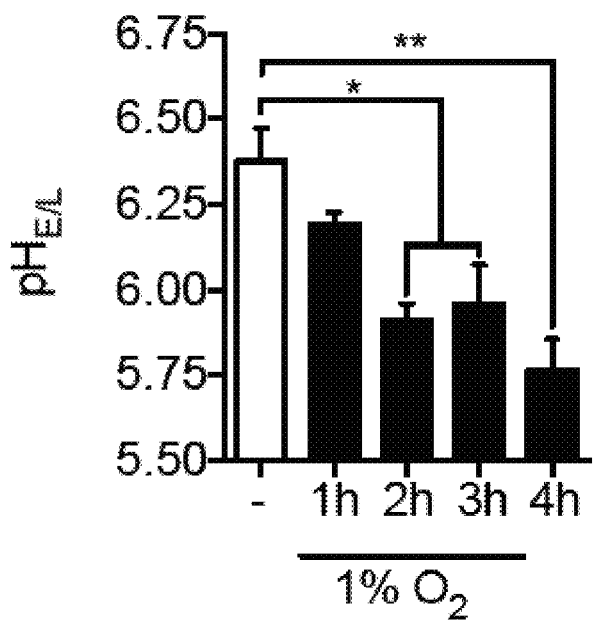
Figure 3F:
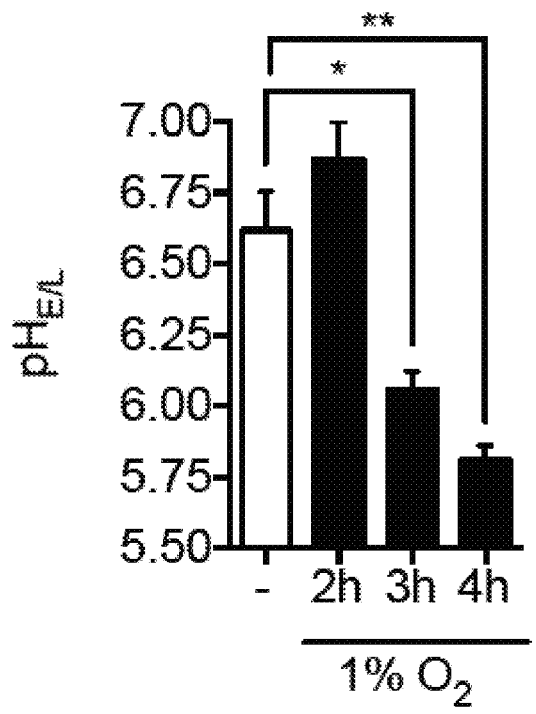
Figure 3G:
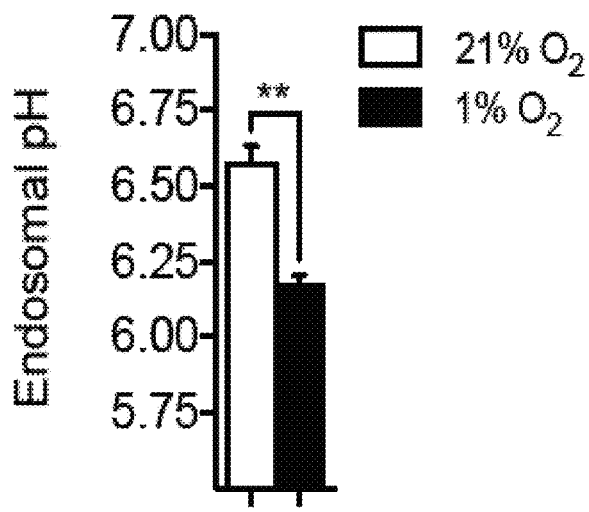
Figure 3H:
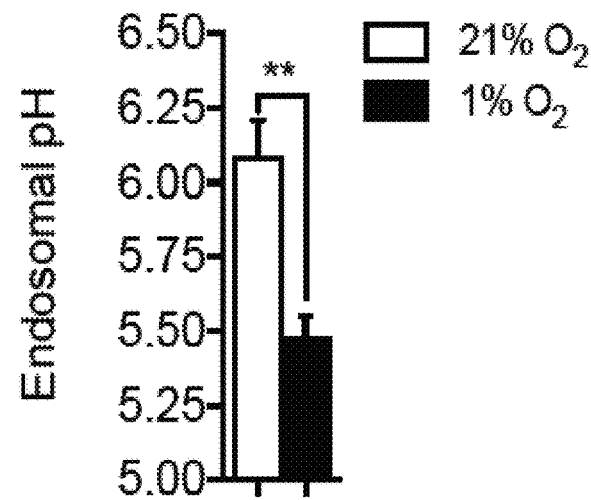
Figure 3I:
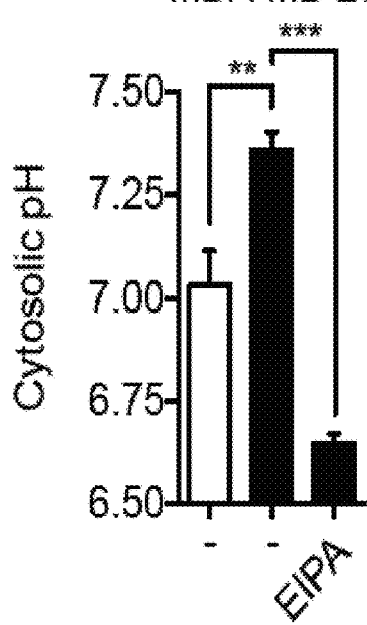
Figure 3J:
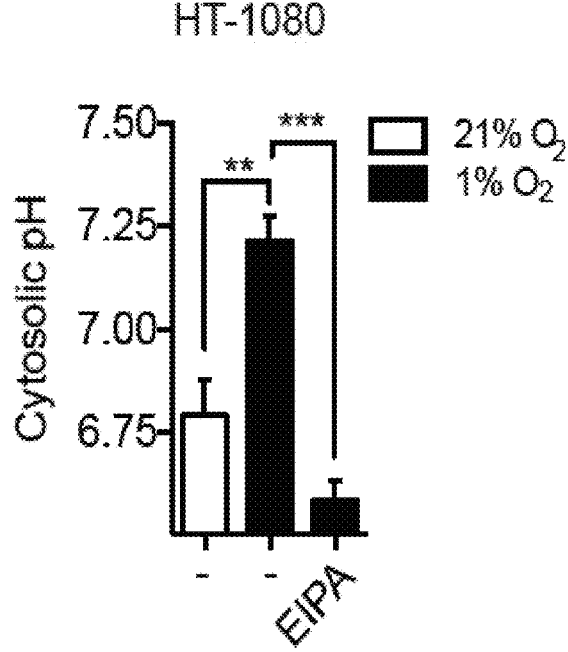
Figure 3K:
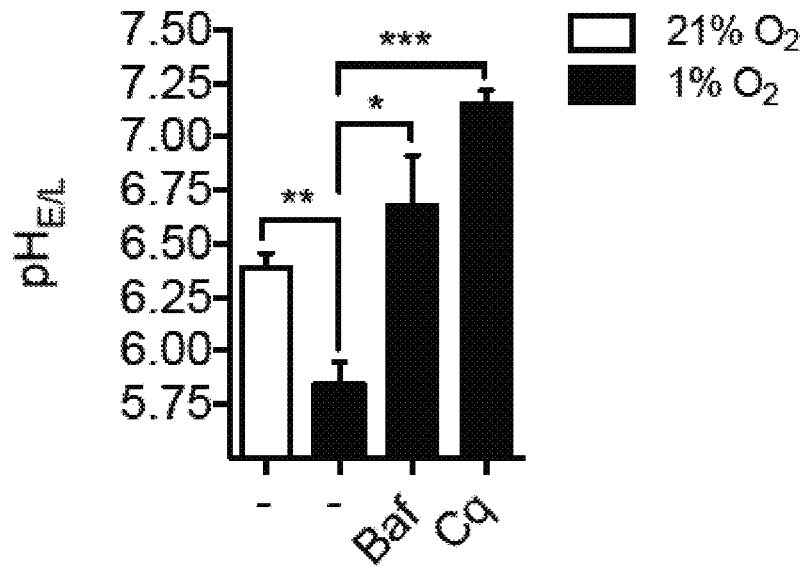
Figure 3L:
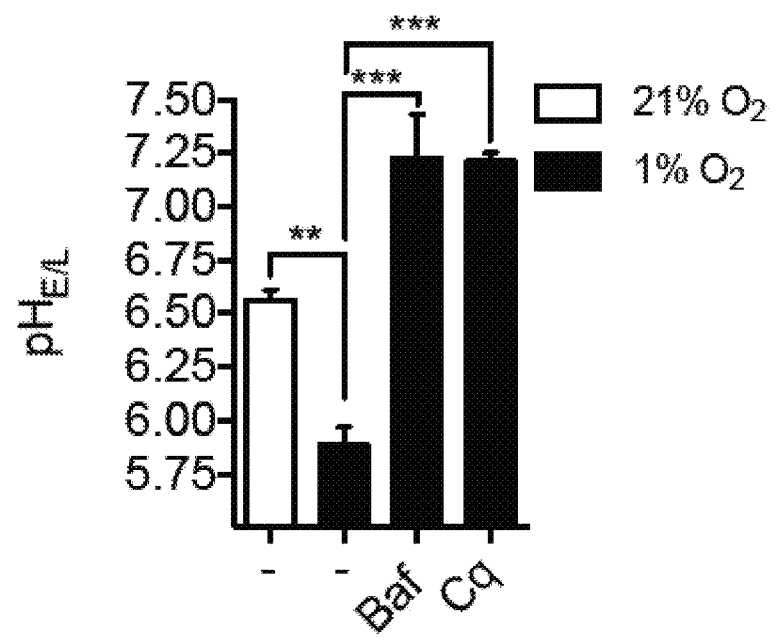

The finding that the increased endosomal sequestration of Dox was pH dependent led the inventors to investigate the influence of hypoxia on the pH of endosomal compartments. To do so, the inventors designed an optimized dual ratiometric approach that uses the pH-sensing probes HPTS and SNARF-1 to measure endosomal/lysosomal pH ($pH_{e/l}$) and cytosolic pH ($pH_c$) respectively, in living cells[30]. After a 16 h incubation of MDA-MB-231 or HT-1080 cells with HPTS, the dye was taken up by pinocytosis, and compartmentalized inside endosomal and lysosomal vesicles with a preferential localization within endosomes (FIGS. 3A-B). This was shown by the percentage of colocalization with the endosome marker transferrin (Tfn) (~60-70%) compared to the lysosomal dye LysoTracker™ (~20-30%) (FIGS. 3C-D). To assess the role of hypoxia in endosomal-lysosomal pH ($pH_{e/l}$), the inventors performed a time-course study of $pH_{e/l}$ measurement in cells incubated under normoxic or hypoxic conditions. Data showed that under normoxic condition, the $pH_{e/l}$ in MDA-MB-231 and HT-1080 cells were mildly acidic with pH values of 6.38±0.17 and 6.62±0.30 respectively. Hypoxia induced a hyperacidification of the vesicles with a decrease in $pH_{e/l}$ reaching 5.77±0.15 for MDA-MB-231 cells and 5.80±0.10 for HT-1080 cells (FIGS. 2E, F). To further detail the effects of hypoxia on endosomal pH, cells were co-labelled with fluorophore-conjugated Tfn and the pH of early and recycling endosomes was determined. Interestingly, Tfn-positive endosomes were significantly more acidic under hypoxic conditions as compared to normoxia, with a pH change of 0.4 and 0.6 pH units for MDA-MB-231 and HT-1080 cells, respectively (FIGS. 3G-H). Conversely, and as expected, hypoxia led to an increase in cytosolic pH which was prevented by the NHE1 inhibitor, EIPA (FIGS. 3I-J)[27]. Cytosol alkalinisation and endosome acidification resulted in an exacerbation of the pH gradient across the endosomal membranes (ΔpH) with a difference of 0.73 and 1.03 pH units for MDA-MB-231 and HT-1080 cells, respectively (Table IV). As expected, hypoxia-induced intravesicular acidification was prevented by the use of the pH neutralizing agents Cq or Baf (FIGS. 3K-L). Taken together, the data indicates that hypoxia leads to alterations in intracellular pH homeostasis resulting in an increase of the pH gradient across the endosomal membranes, a finding that is related to the observed Dox compartmentalization within acidified endosomes and Dox resistance.

Example 5: NHE6 Delocalization Triggers Endosome Hyperacidification

Figure 4A:
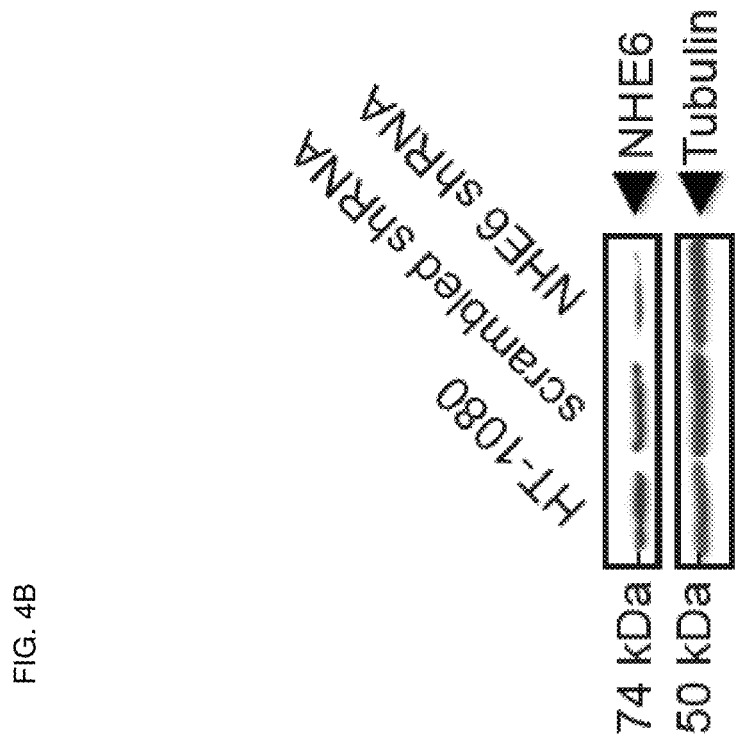
FIGS. 4A-L. NHE6 is a key NHE involved in hypoxia-induced endosome acidification and Dox resistance.
Figure 4B:
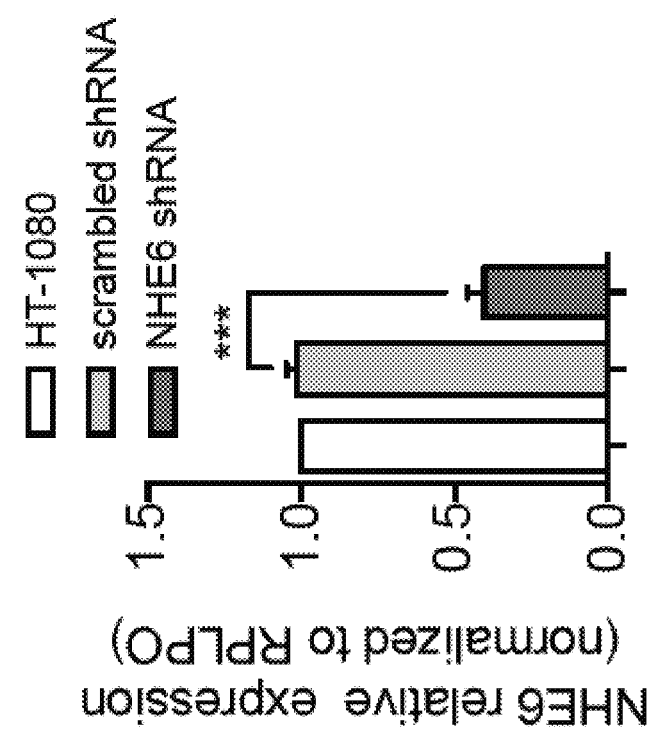
Figure 4C:
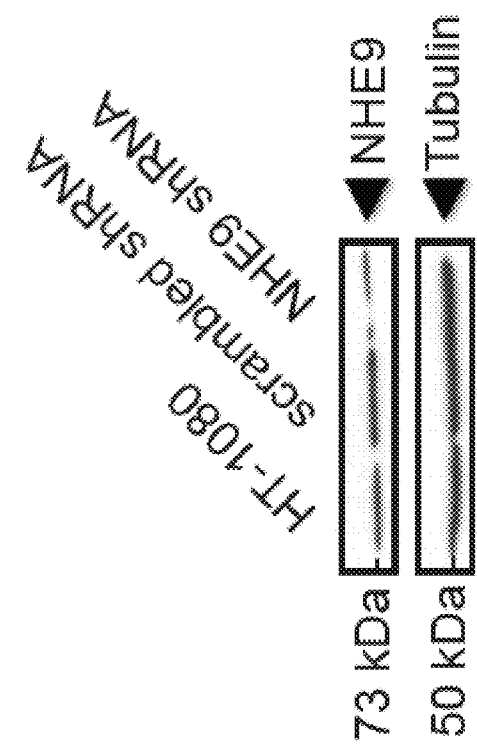
Figure 4D:
Figure 4F:
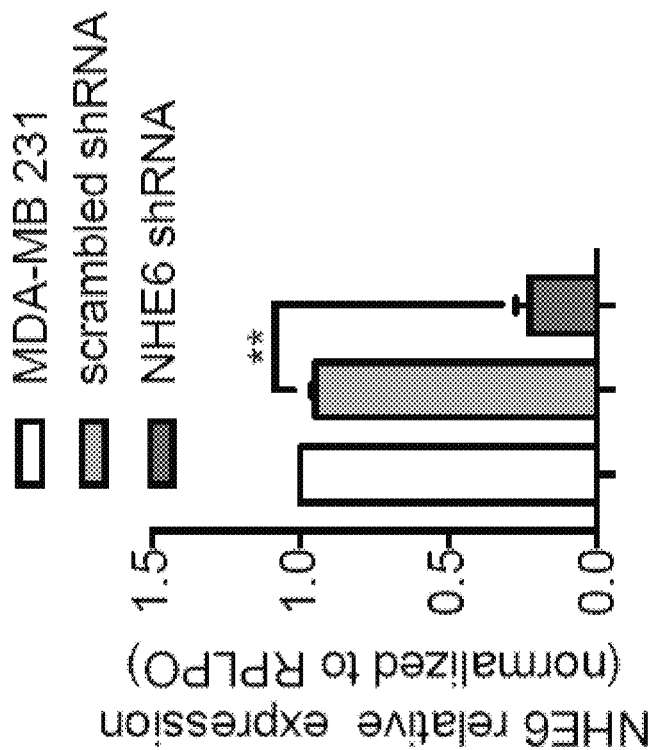
Figure 4E:
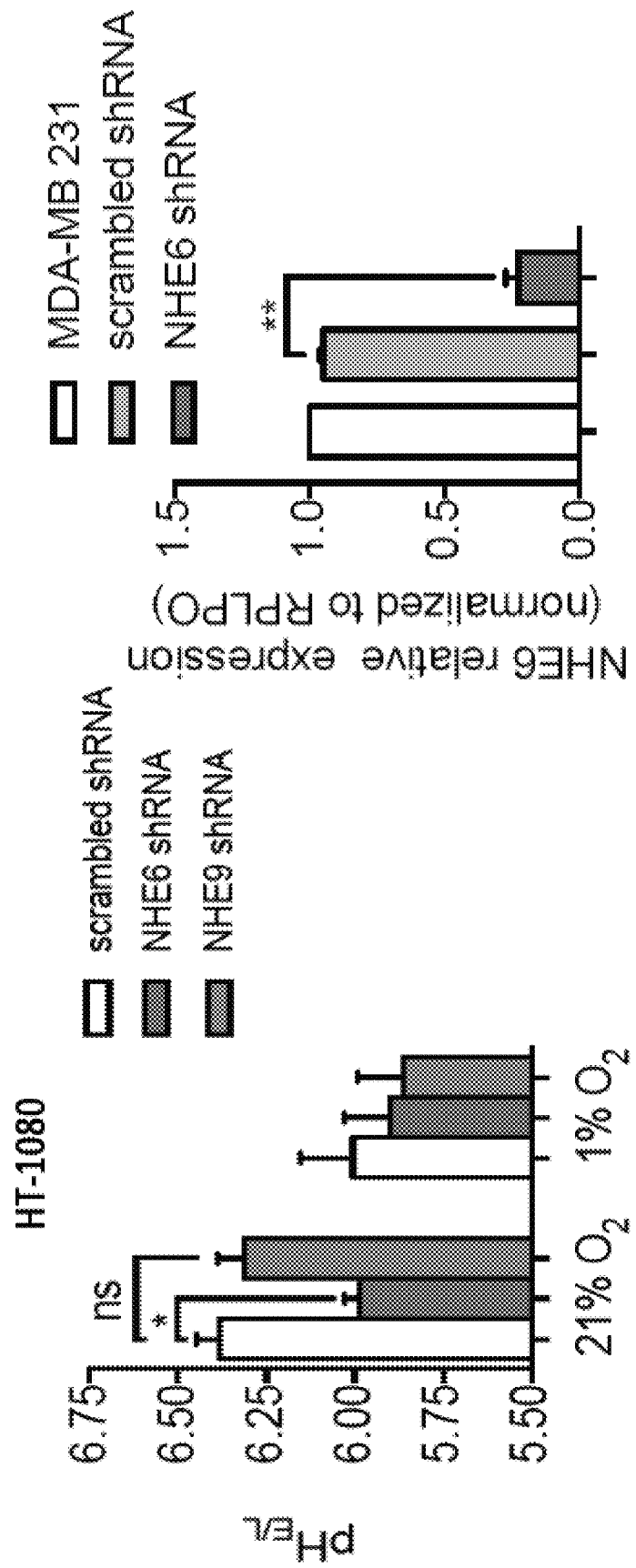
Figures 4G, 4H:
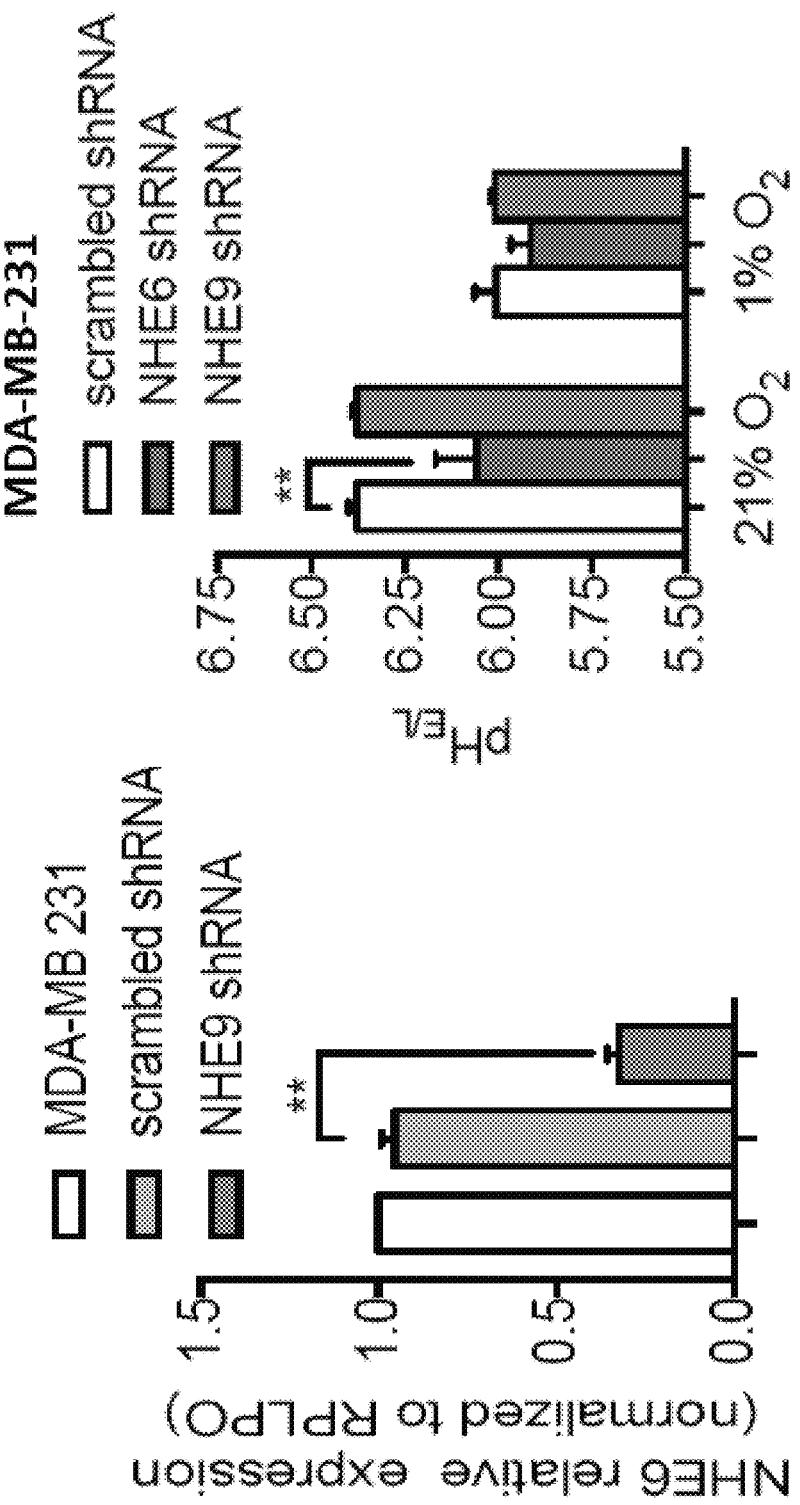
Figure 4I:
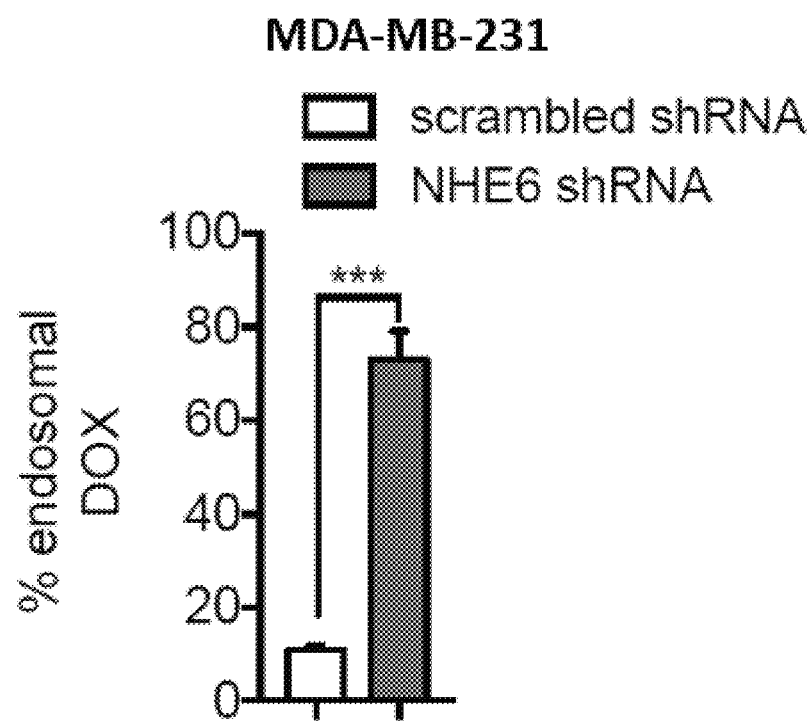
Figure 4J:
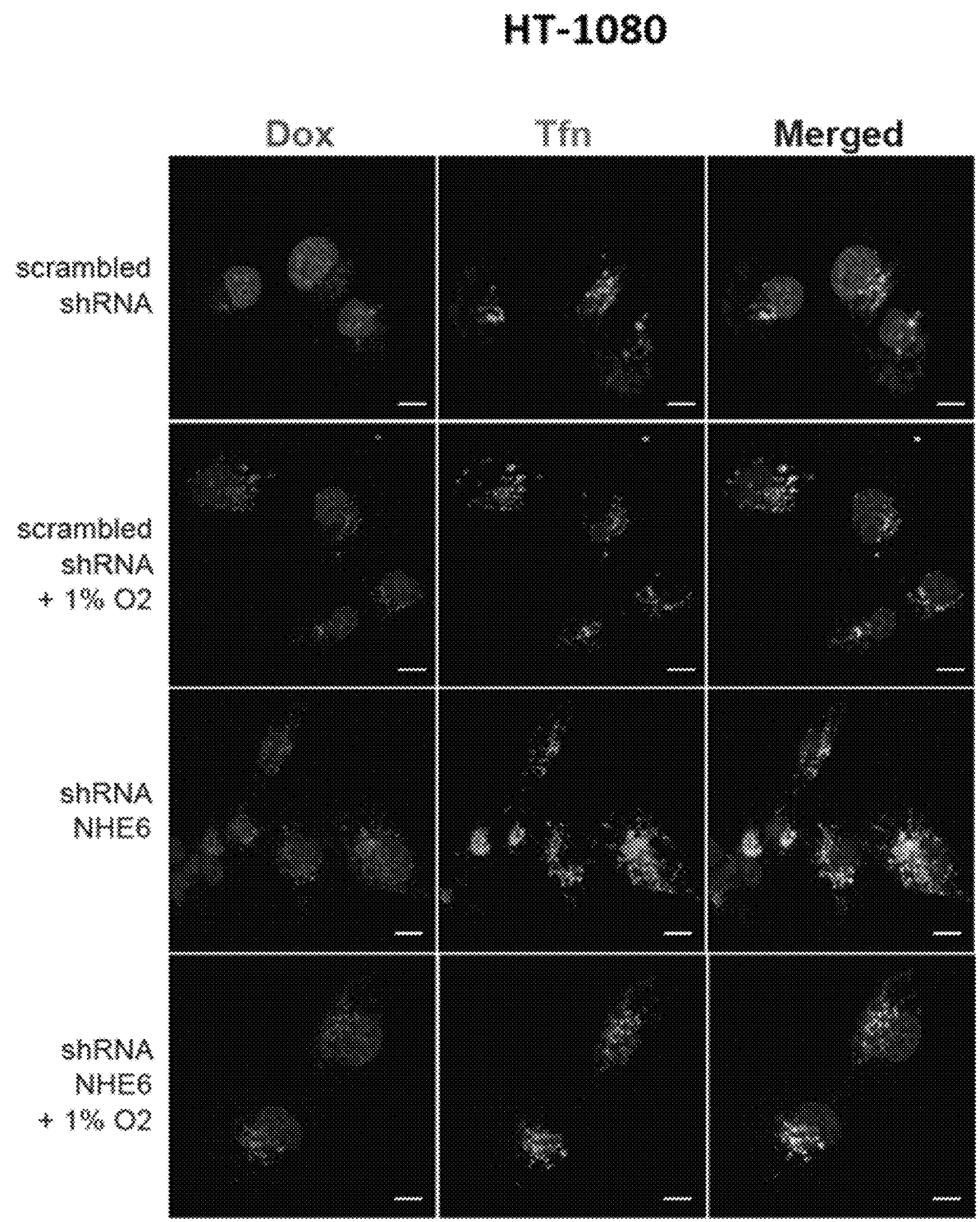
Figure 4K:
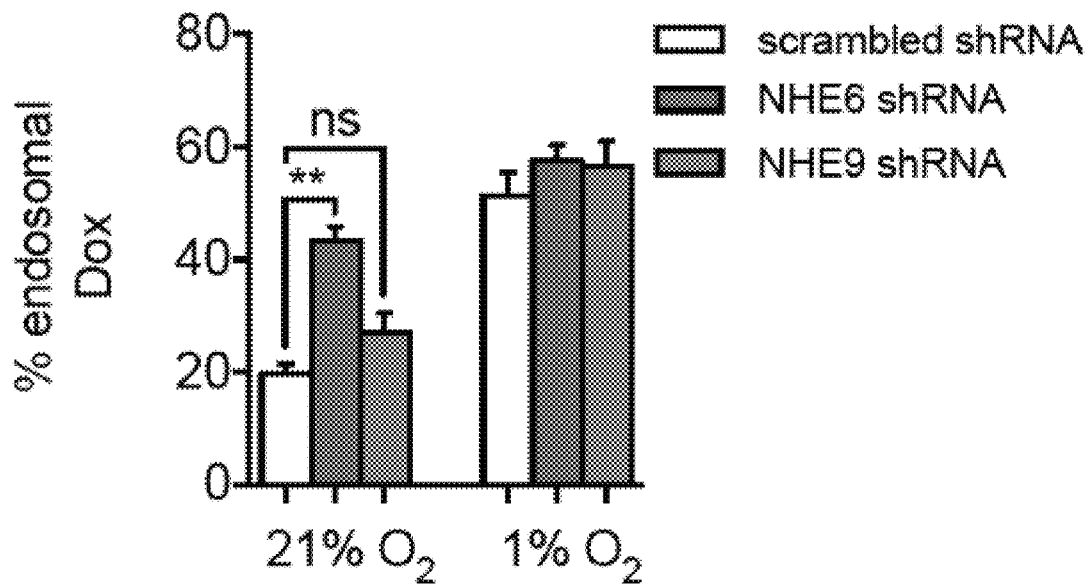
Figure 4L:
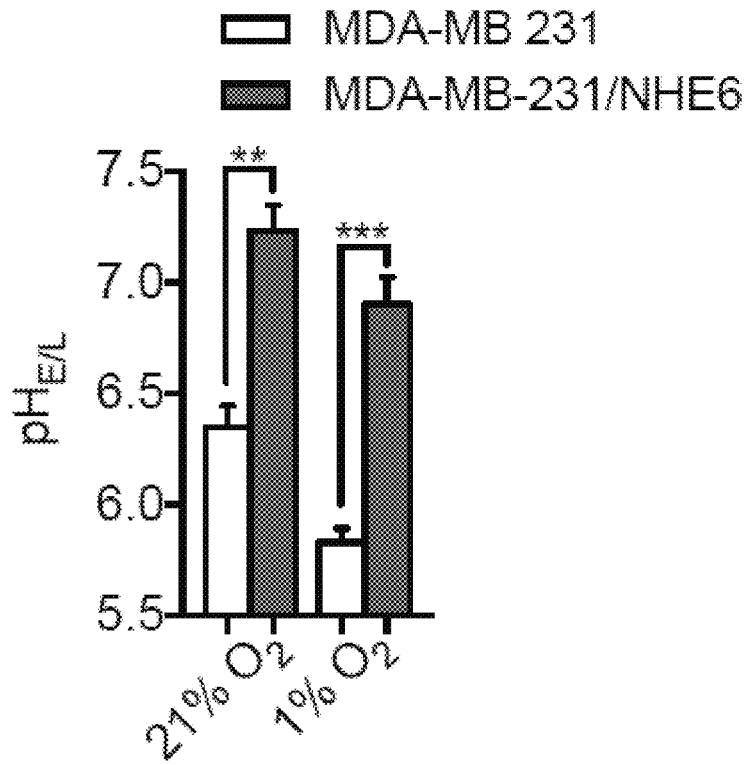

The inventors next investigated the mechanisms that could account for endosome acidification in hypoxia. To maintain pH homeostasis, cells utilize an array of acid-base modulators, such as the sodium/proton exchangers (NHEs) that are critical regulators of pH within the cell and the extracellular microenvironment. Nine NHE isoforms have been described in human[19]. NHE1-5 are located at the plasma membrane, whereas NHE6 and NHE9 are associated with sorting and recycling endosomes, and NHE7 and NHE8 with the trans- and mid-trans-Golgi stacks, respectively[20]. By facilitating proton efflux, organellar NHEs are thought to counteract the acidity generated by V-ATPase, thereby limiting luminal acidification[21]. The inventors evaluated the potential contribution of organellar NHE6, predominantly located at early endosomes, and NHE9, associated with recycling and late endosomes[20] to hypoxia-induced endosome acidification. Silencing of NHE6 in HT-1080 or MDA-MB-231 cells resulted in hyperacidification of the intravesicular compartment to a level similar to that induced by hypoxia, whereas depletion of the NHE9 isoform had no significant impact (FIGS. 4A-H). In contrast, overexpression of NHE6 increases the pH of intracellular vesicles and blocks the acidification induced by hypoxia (FIG. 4I). NHE6 knockdown in normoxic cells was also associated with increased sequestration of Dox within endosomes in HT-1080 (~20%, shScrambled vs ~45%, shNHE6) (FIGS. 4J-K) or MDA-MB-231 cells (~10%, shScrambled vs ~74%, shNHE6) (FIG. 4L), an event that correlated with a 2.4-fold increase in cell resistance to Dox reaching 1050 values similar to the ones observed under hypoxia (Table V). In contrast, NHE9 silencing did not significantly affect Dox sequestration (FIG. 4K) or cell sensitivity to Dox (Table V). These findings indicate that amongst the two endosome-located NHE isoforms, only depletion of NHE6 influences Dox sequestration in the endosomal compartment, an observation associated with drug resistance.

TABLE V

| IC$_{50}$ values of doxorubicin in NHE6 or NHE9 knockdown cells cultured in normoxia or hypoxia. | | | |
|---|---|---|---|
| Experimental condition | IC$_{50}$ DOX (nM) | Fold (compared to scrambled 21% O2) | p-value |
| scrambled shRNA 21% O$_2$ | 178.8 +/− 17.1 | 1.0 | — |
| scrambled shRNA 1% O$_2$ | 458.8 +/− 64.7 | 2.5 | 0.0001 |
| shRNA NHE6 21% O$_2$ | 421.4 +/− 27.8 | 2.4 | 0.0003 |

TABLE IV

| pH measurements in cytosol and endosomal compartments in MDA-MB-231 and HT-1080 cells exposed to 1% or 21% O$_2$ for 4 h. | | | | |
|---|---|---|---|---|
| | MDA-MB-231 | | HT-1080 | |
| | 21% O$_2$ | 1% O$_2$ | 21% O$_2$ | 1% O$_2$ |
| Cytosol | 7.03 +/− 0.14 | 7.36 +/− 0.17 | 6.79 +/− 0.19 | 7.22 +/− 0.13 |
| Endosome | 6.57 +/− 0.10 | 6.17 +/− 0.06 | 6.08 +/− 0.18 | 5.47 +/− 0.15 |
| ΔpH (Cytosol − Endosome) | 0.46 | 1.19 | 0.71 | 1.75 |
| Δ(ΔpH) (1%O$_2$ − 21%O$_2$) | | 0.73 | | 1.03 |

TABLE V-continued

IC$_{50}$ values of doxorubicin in NHE6 or NHE9 knockdown cells cultured in normoxia or hypoxia.

| Experimental condition | IC$_{50}$ DOX (nM) | Fold (compared to scrambled 21% O2) | p-value |
|---|---|---|---|
| shRNA NHE9 21% O$_2$ | 201.5 +/− 29.4 | 1.1 | Ns |

Data are presented at the mean (nM)+/− standard deviation. IC$_{50}$, half maximal inhibitory concentration (n=3 independent experiments with 3 replicates in each experiment). P-values were determined with unpaired t-test with Welch's correction.

Figure 5A:
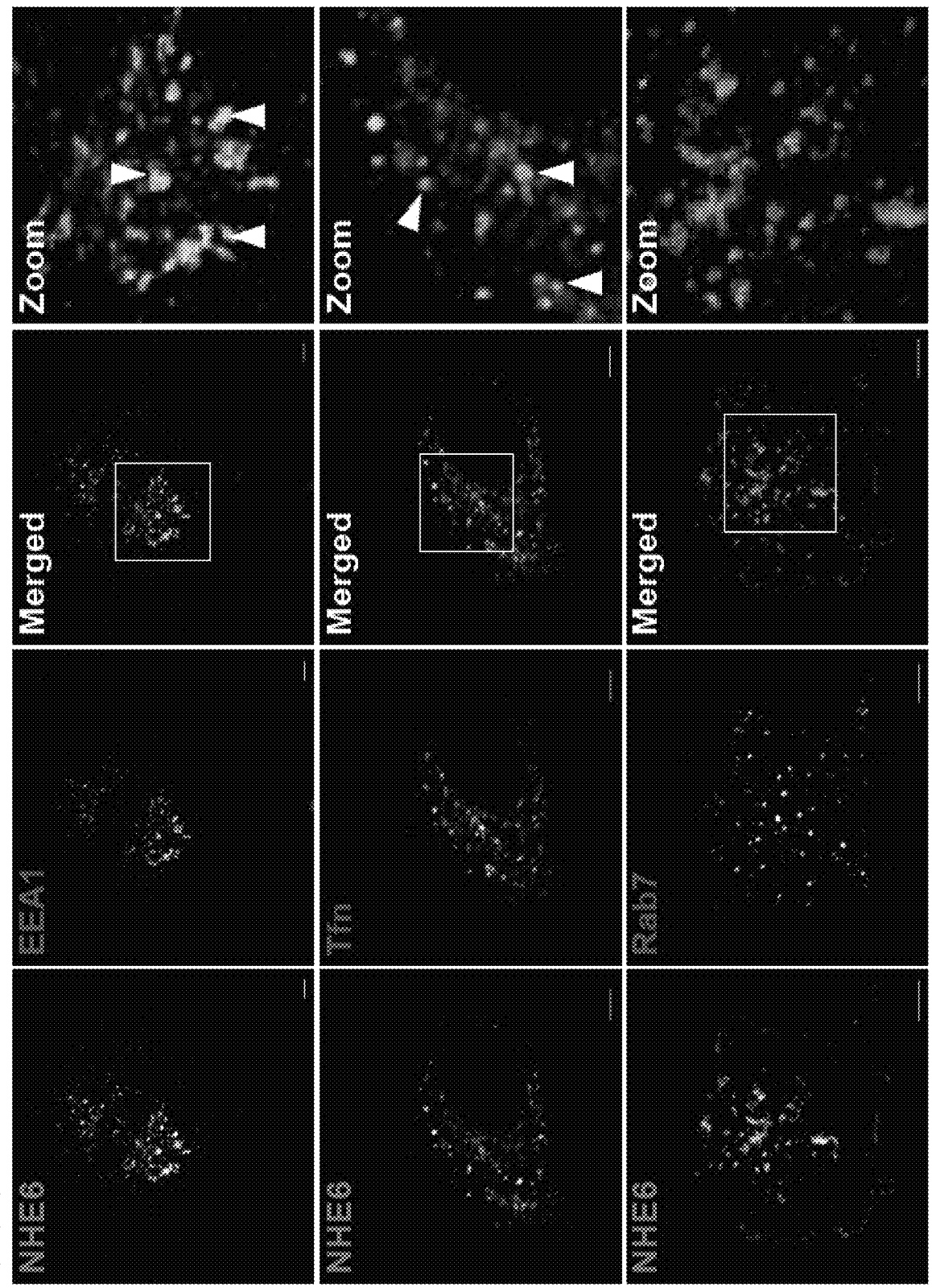
FIGS. 5A-B. NHE6 is predominantly located at early/recycling endosomes in HT-1080 cells.
Figure 5B:
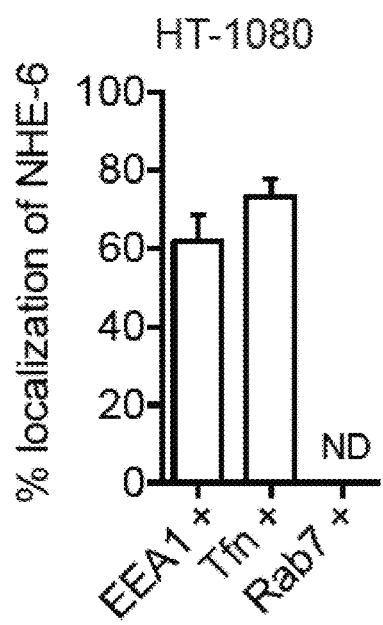

Because NHE6 is known to recycle between intravesicular compartments and the plasma membrane and interference with NHE6 trafficking or loss of the protein resulted in hyperacidification of the endosomal compartment[31], the inventors sought to determine whether NHE6 compartmentalization was altered by hypoxia. In normoxic cells, NHE6 strongly colocalized with the early endosomal markers EEA1 (~62%) and early and recycling endosomal marker transferrin (~76%), but not with the late endosomal/lysosomal marker Rab7 (FIGS. 5A-B). Using biotinylated cells to assess levels of NHE6 associated with the plasma membrane, the inventors also observed that a small percentage of NHE6 (~10% in MDA-MB-231 cells; ~9% in HT-1080 cells) was located at the plasma membrane under basal conditions (FIGS. 6 A-C). These results confirm that under normoxia, NHE6 is mainly localized at early and recycling endosomes with low levels also found at the plasma membrane[32].

Figure 6A:
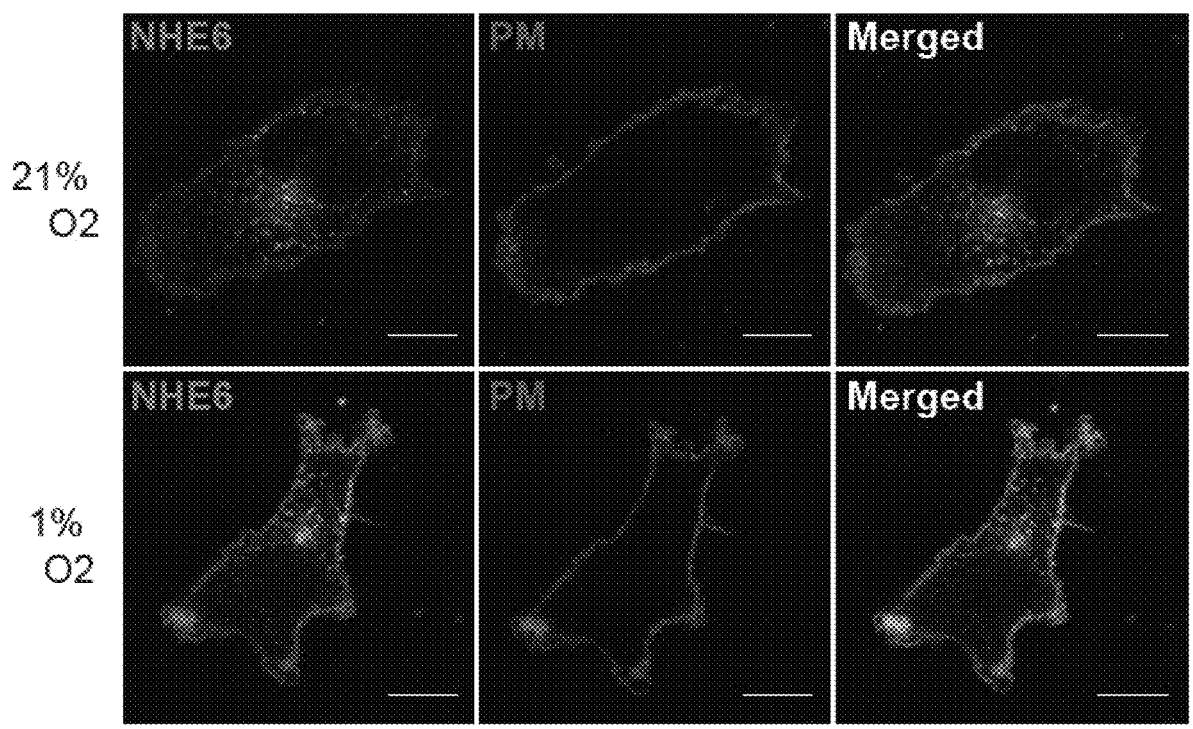
FIGS. 6A-L. NHE6 is relocalized to the plasma membrane in hypoxia leading to endosomal acidification.
Figure 6B:
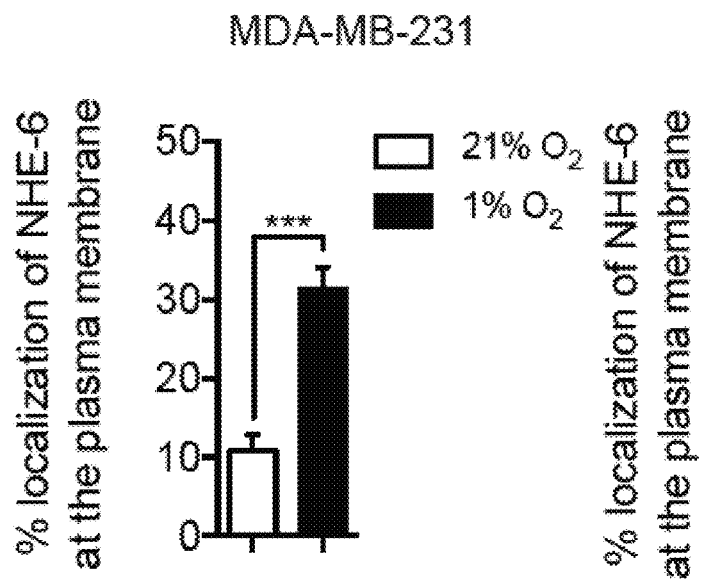
Figure 6C:
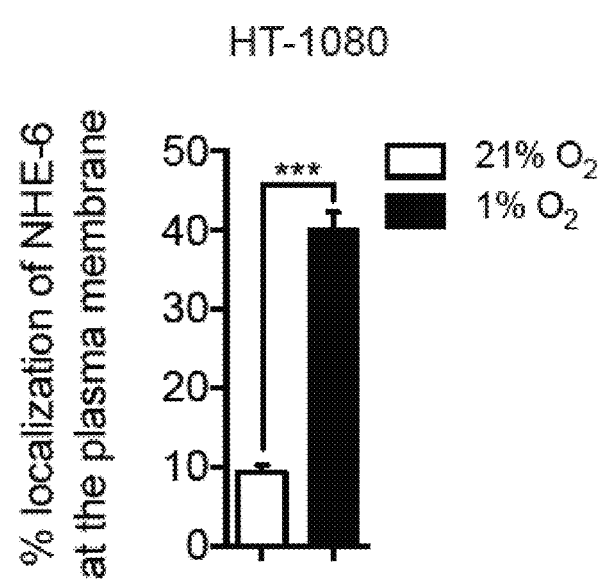
Figure 6D:
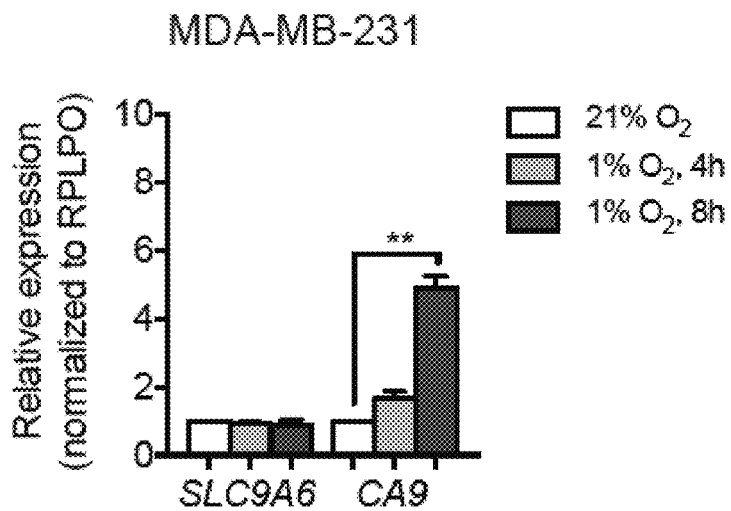
Figure 6E:
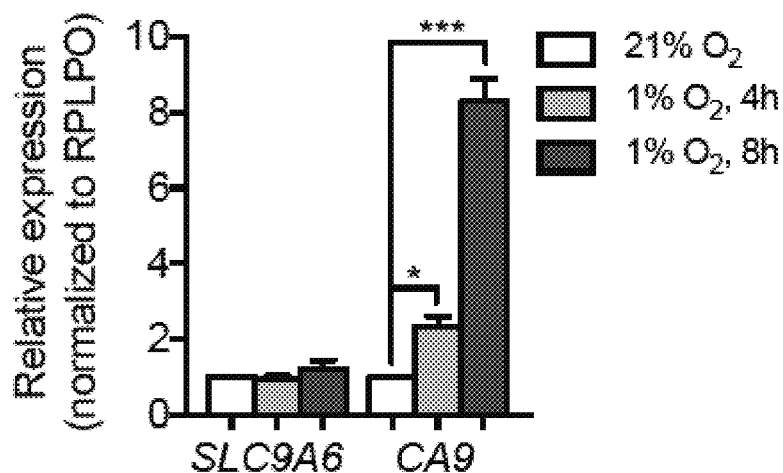
Figure 6F:
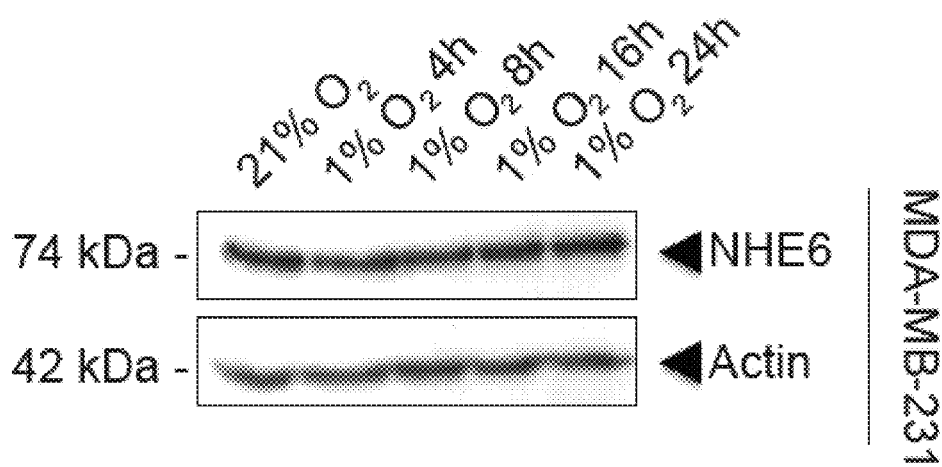
Figure 6G:
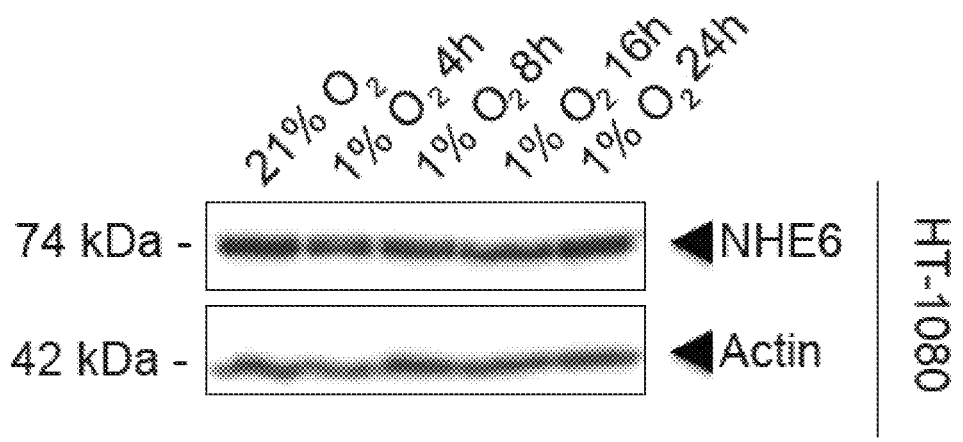
Figure 6H:
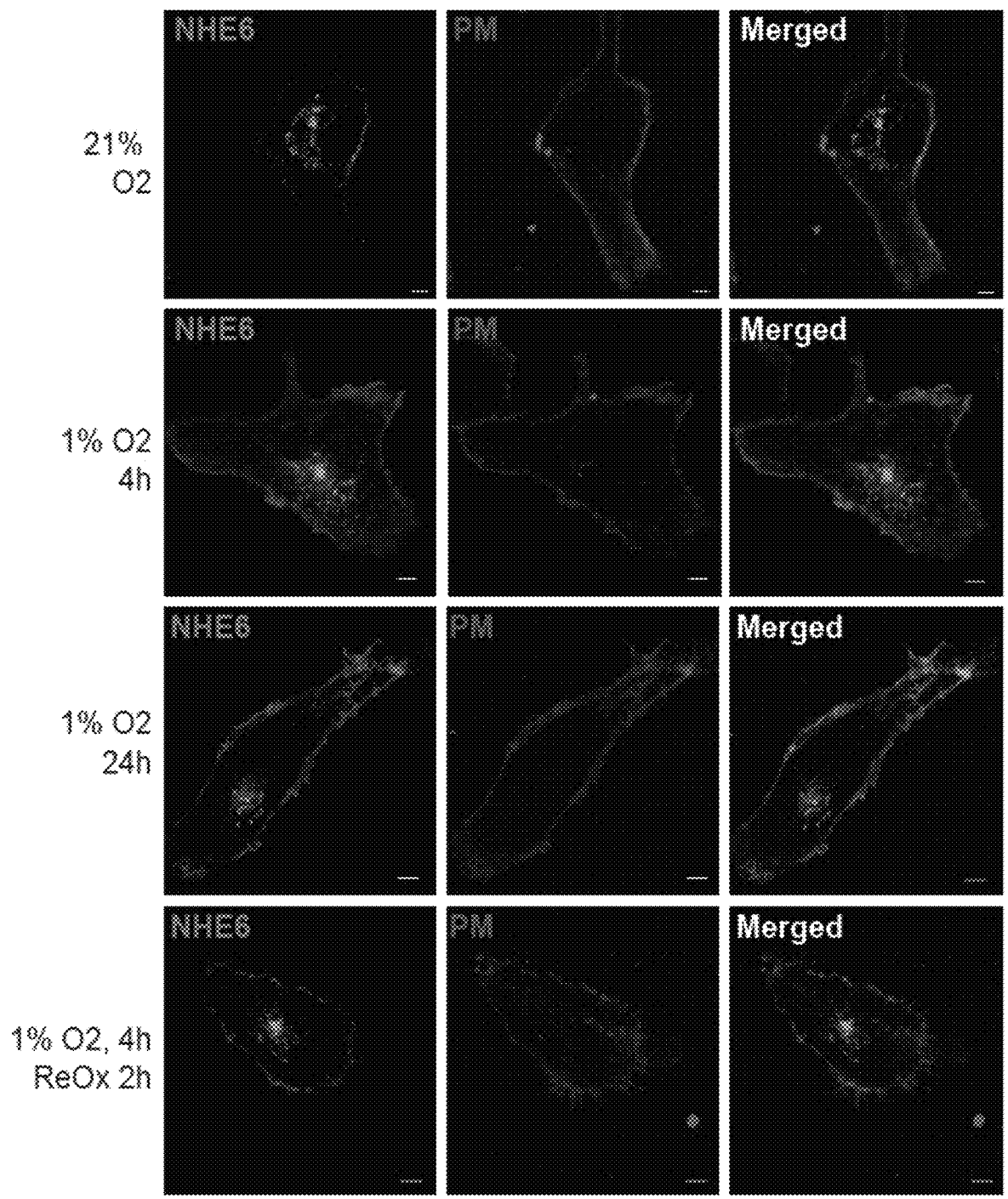
Figure 6I:
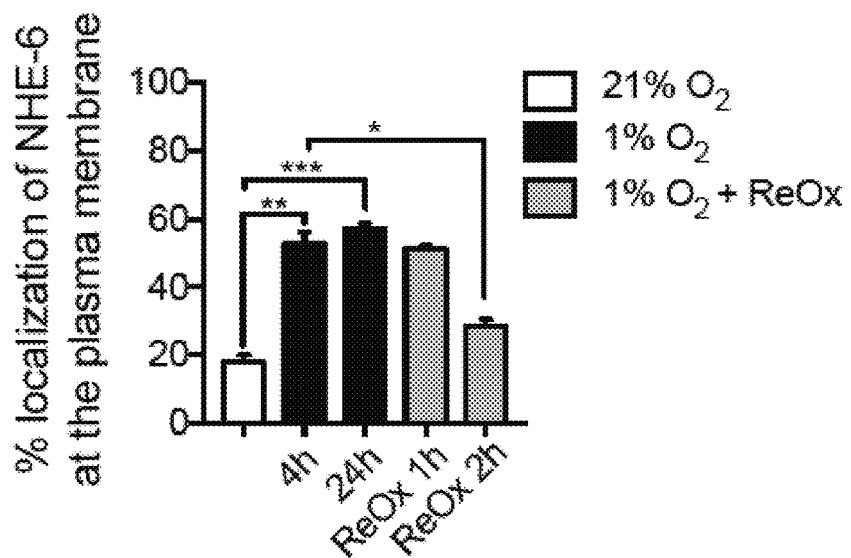

Interestingly, following a 4 h incubation period under hypoxic conditions, the proportion of NHE6 at the plasma membrane was increased 3-fold in MDA-MB-231 cells and, 4-fold in HT-1080 cells (FIGS. 6A-C). This increase was not associated with induction of NHE6 mRNA or protein levels (FIGS. 6D-G). In addition, incubation of HT-1080 cells under hypoxic conditions for 24 h resulted in a similar increase in NHE6 distribution to the plasma membrane as compared to the shorter (4 h) incubation time (FIGS. 6 H-I). Re-exposure of the cells to ambient oxygen levels reduced plasma membrane NHE6 levels (FIGS. 6 H-I), suggesting that the mobilization of NHE6 to the plasma membrane is a reversible event.

Figure 6J:
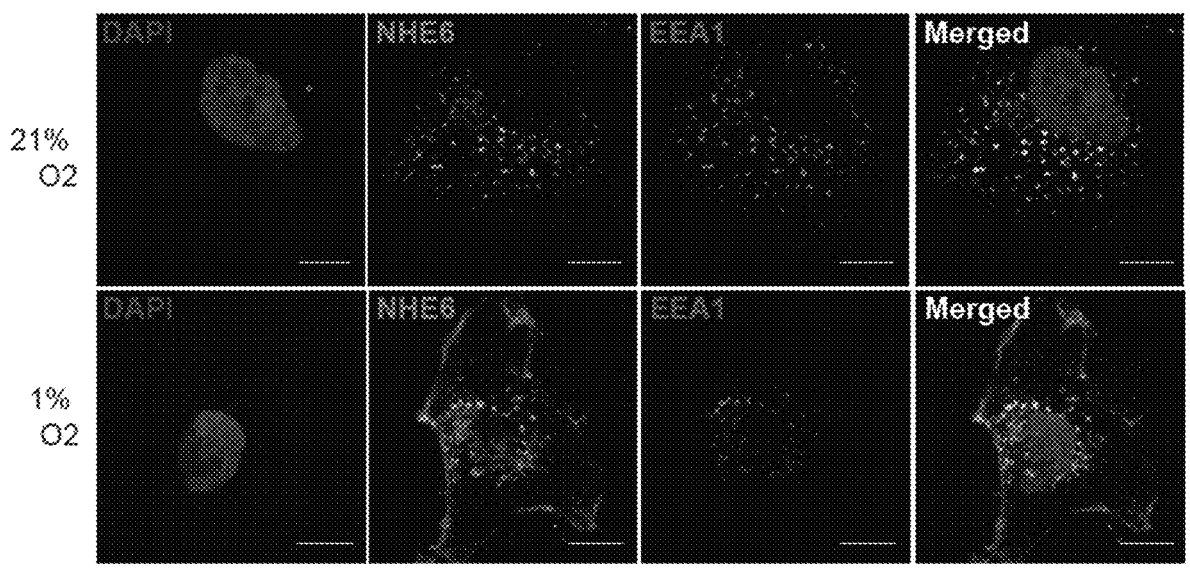
Figure 6K:
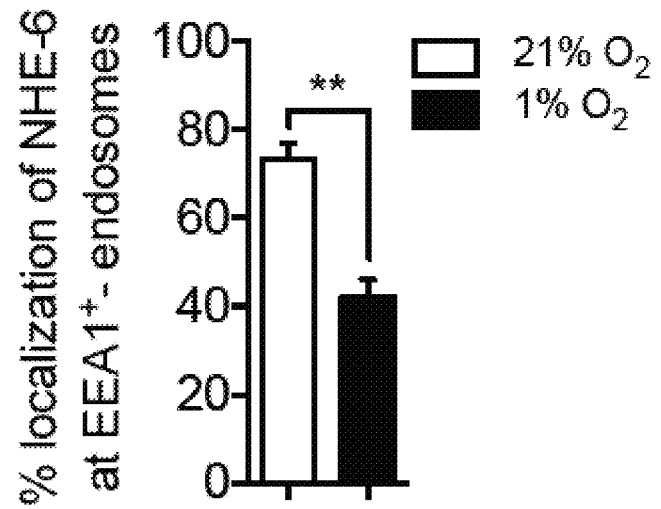
Figure 6L:
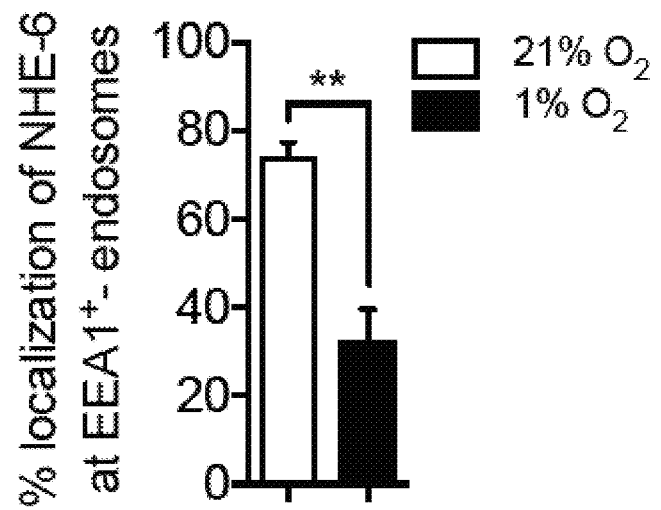

Co-staining with EEA1 indicated that the increased localization of NHE6 at the plasma membrane was associated with a 1.8-fold and 2.3-fold reduction in its localization at the EEA1+-endosomal compartment in MDA-MB-231 and HT-1080 cells, respectively (FIGS. 6J-L). These data suggest that the effects of hypoxia on Dox sequestration and cell resistance were related to the redistribution of NHE6 from endosomes to the plasma membrane, a mechanism that leads to hyperacidification of the endosomal lumen.

Example 6: The RACK1-PKC-NHE6 Axis Regulates Dox Resistance in Hypoxia

Figure 7A:
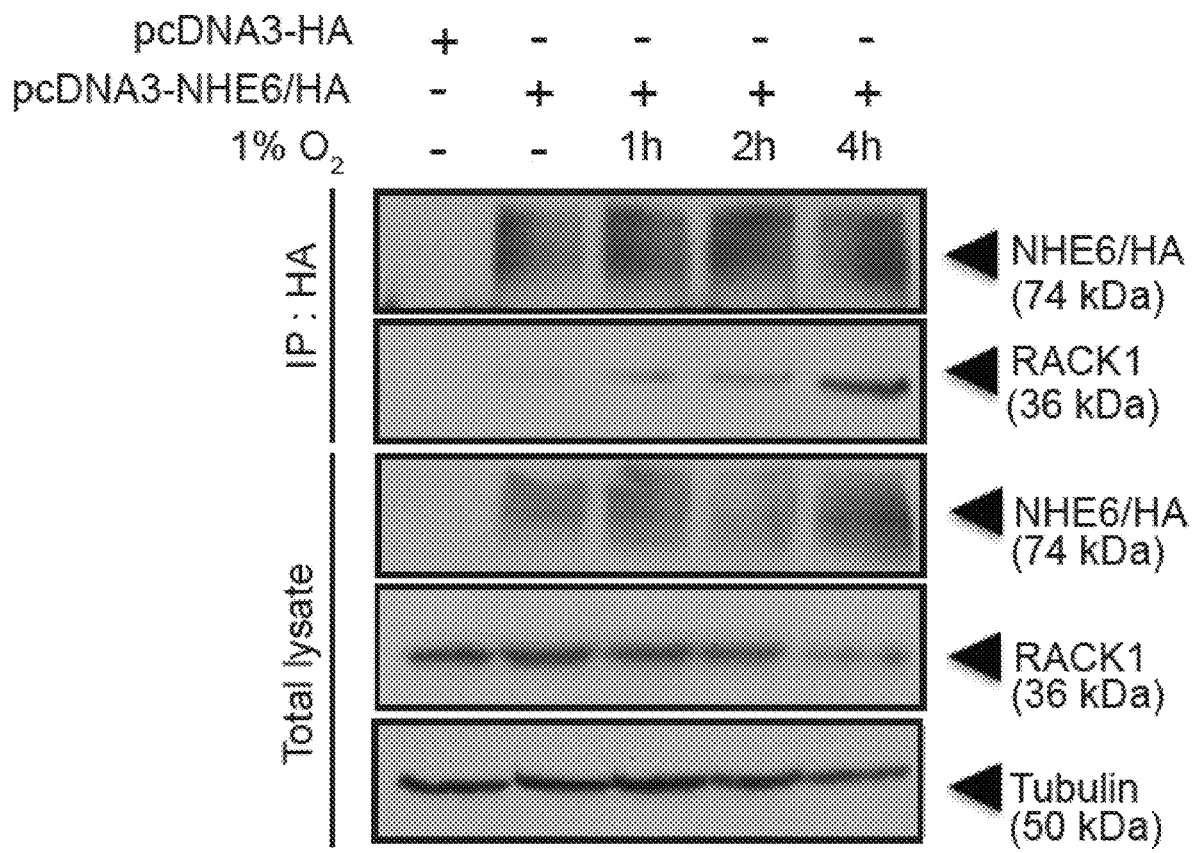
FIGS. 7A-G. Involvement of RACK1 in NHE6 relocalization to the plasma membrane.
Figure 7B:
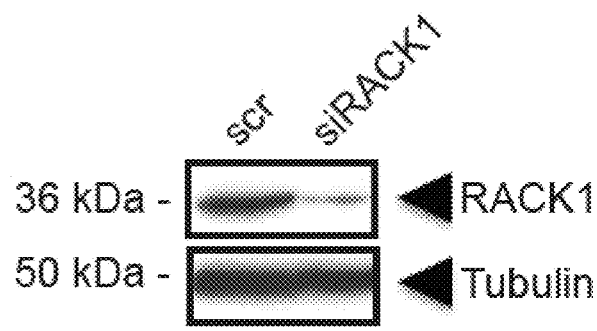
Figure 7C:
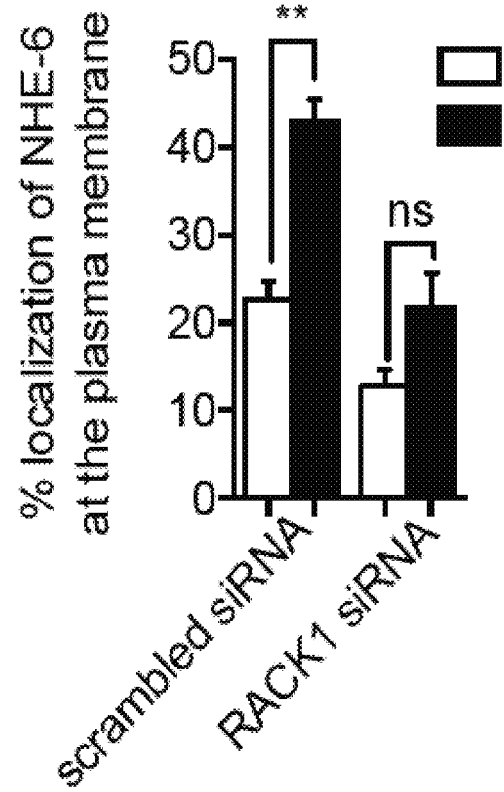
Figure 7D:
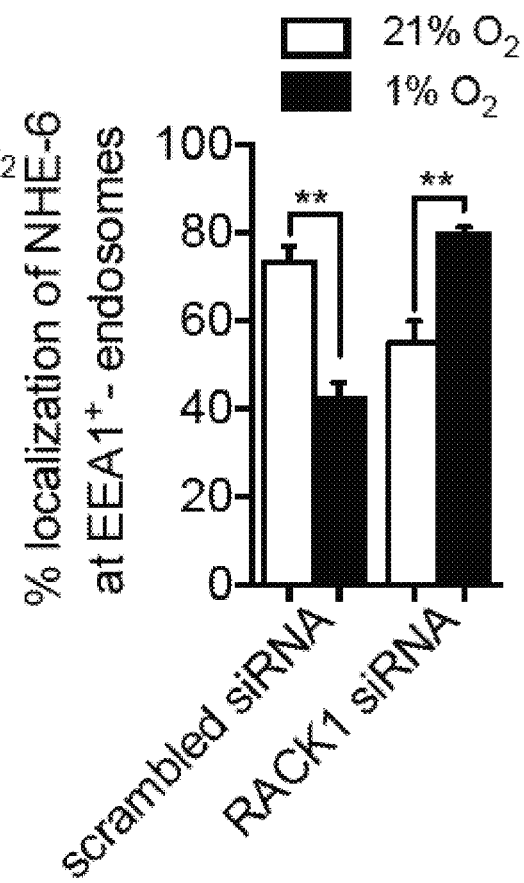
Figure 7E:
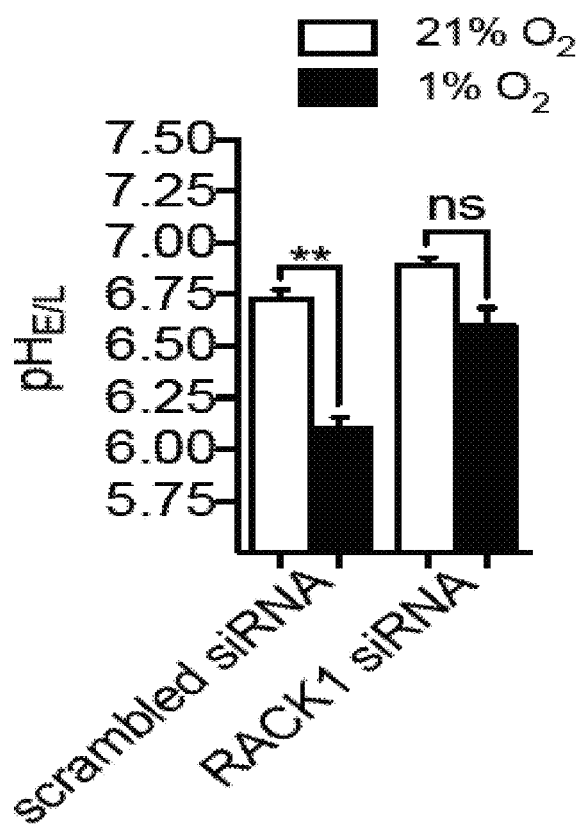
Figure 7F:
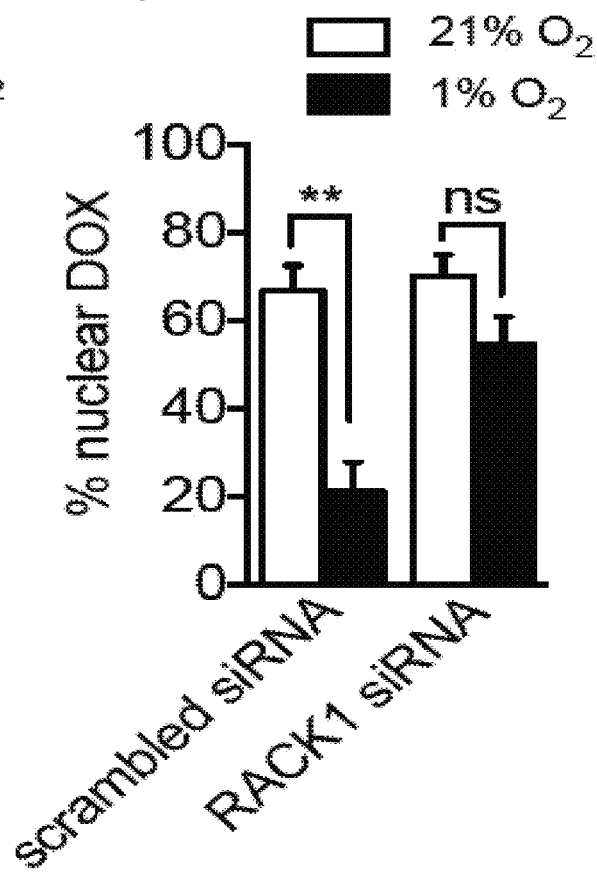
Figure 7G:
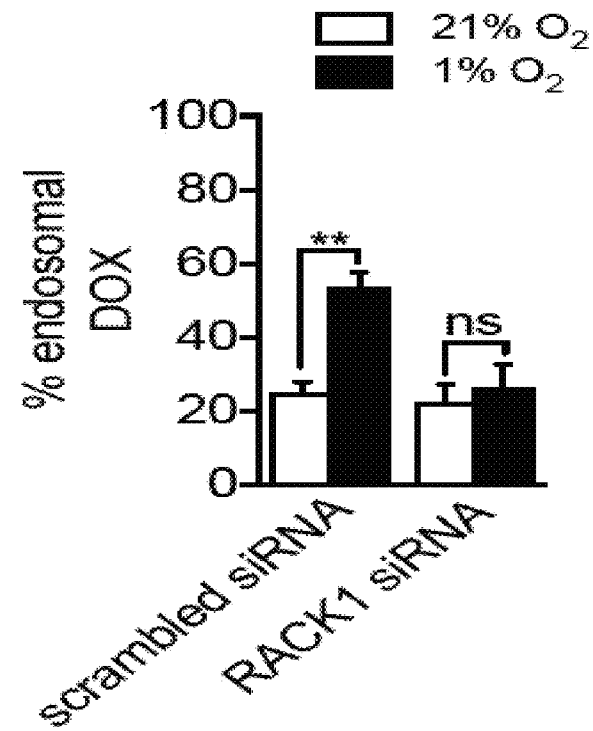

Co-immunoprecipitation assays consistently showed that incubation of HT-1080 cells under hypoxia increased the interaction of receptor for activated C kinase (RACK1) with NHE6 as early as 1 h after treatment (FIG. 7A). To address the potential link between RACK1-NHE6 binding and NHE6 accumulation at the plasma membrane, the inventors used biotin-labeled and RACK1-depleted (siRNA) cells. RACK1 knockdown resulted in a complete blockade of hypoxia-induced NHE6 relocalization from EEA1+ endosomes to the plasma membrane (FIGS. 7B-D). Interestingly, RACK1 depletion also restored normal endosomal pH and prevented the sequestration of Dox within the endosomal compartment (FIGS. 7E-G).

The inventors then investigated whether PKC was involved in hypoxia-induced NHE6-RACK1 interaction.

Figure 8A:
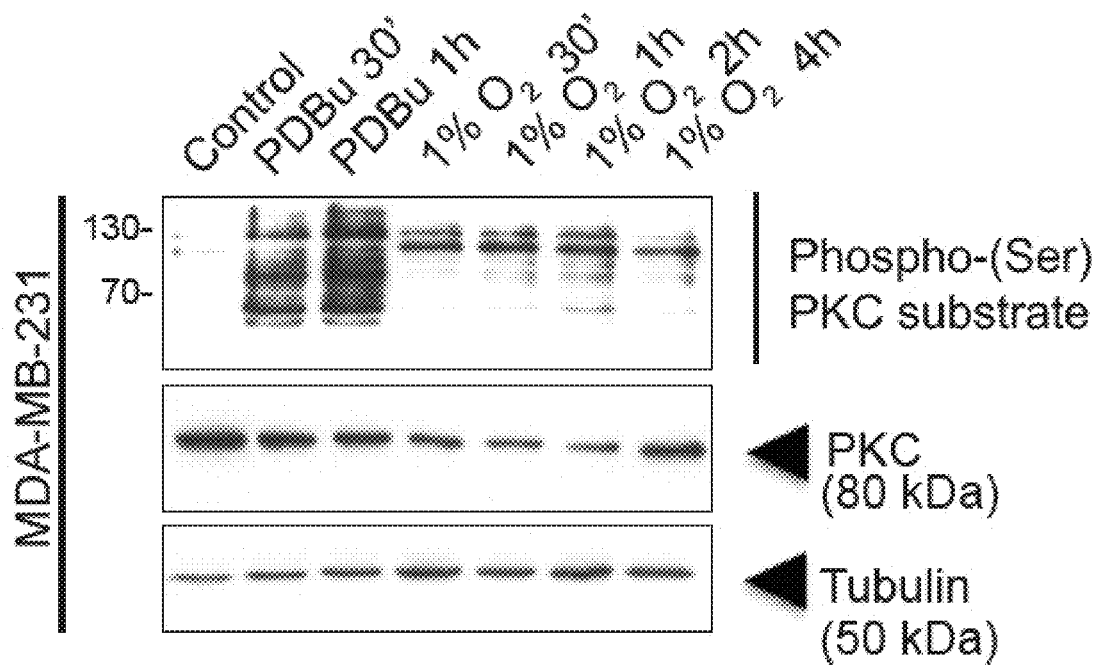
FIGS. 8A-H. NHE6 relocalization to the plasma membrane is dependent on PKC.
Figure 8B:
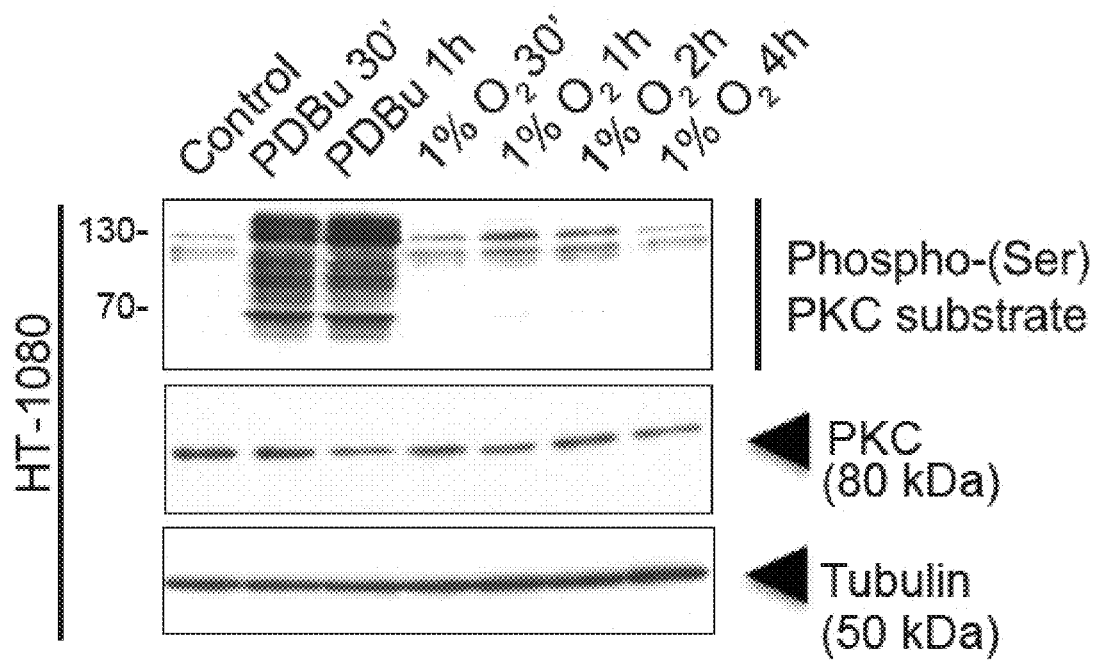
Figure 8C:
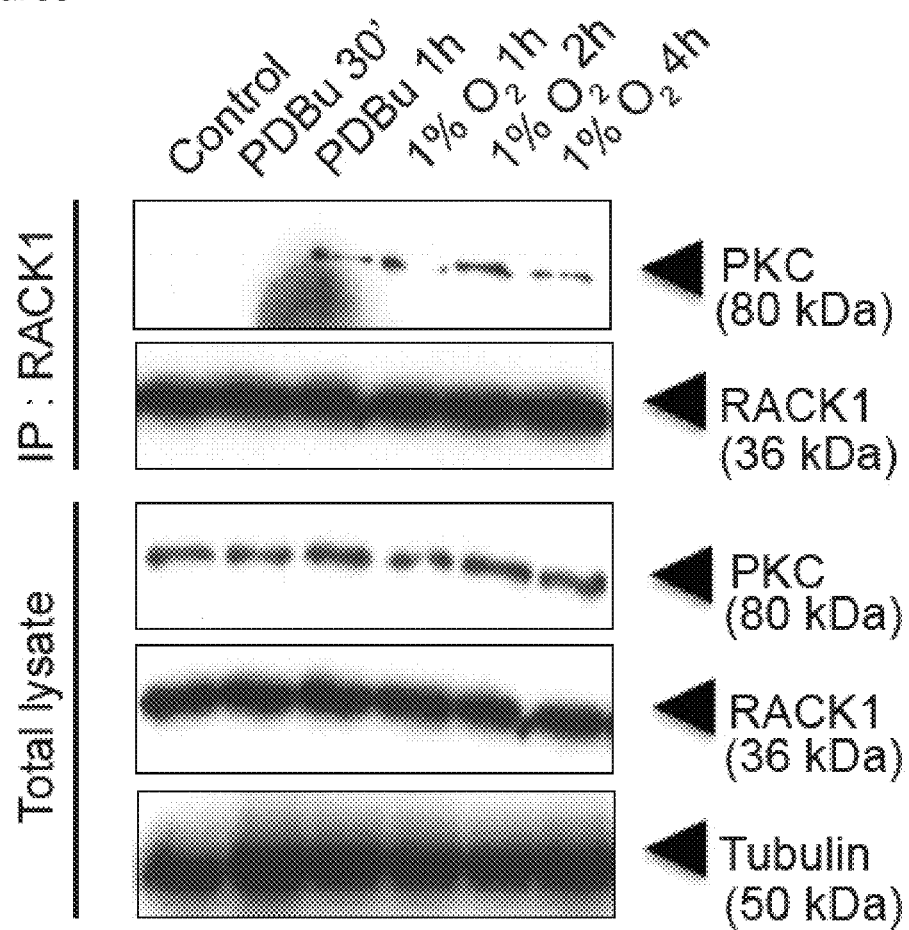
Figure 8D:
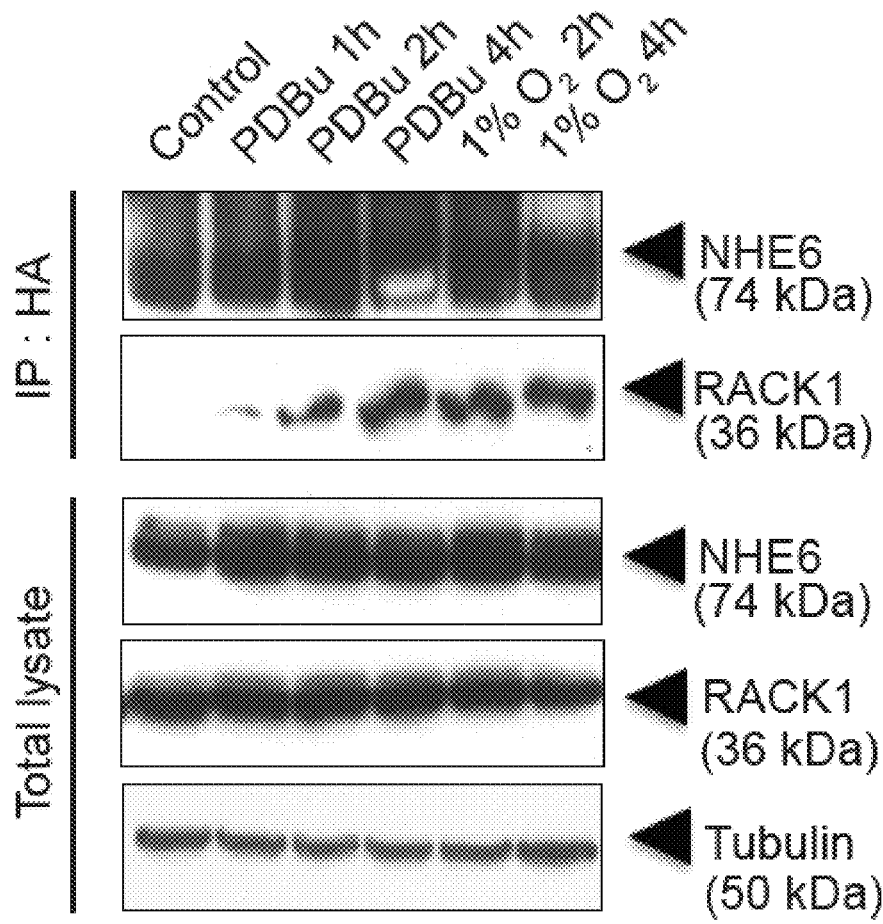
Figure 8E:
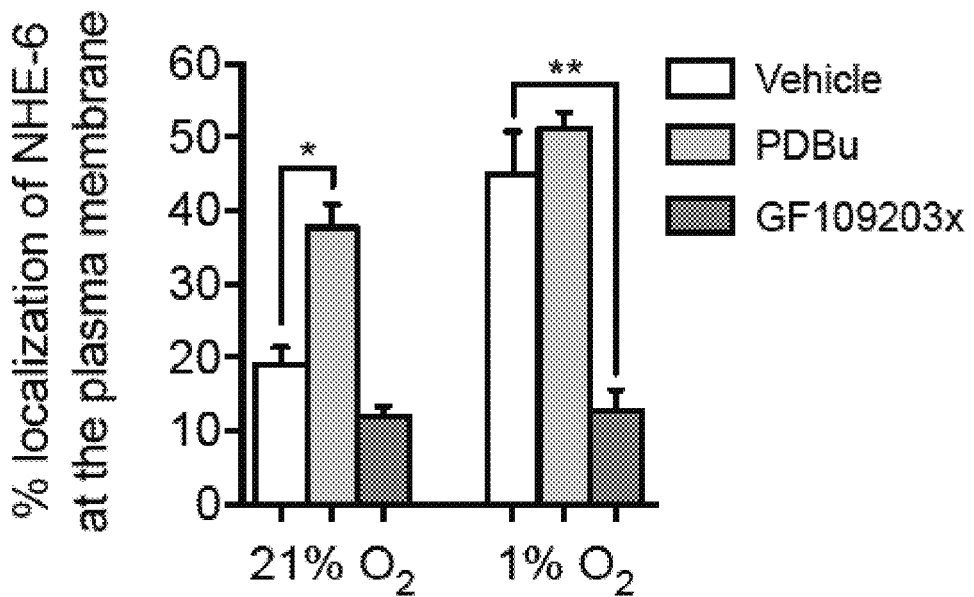
Figure 8F:
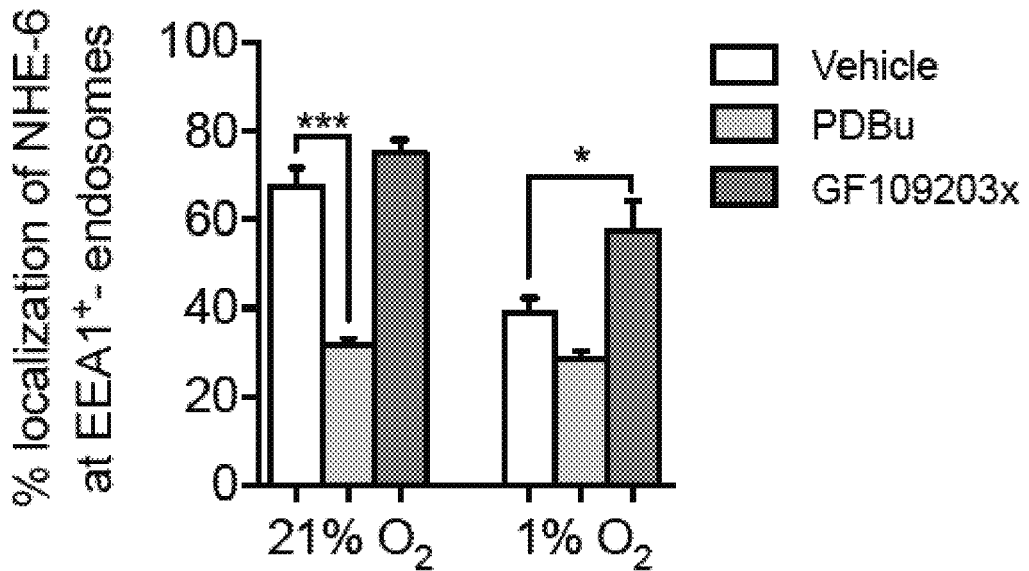
Figure 8G:
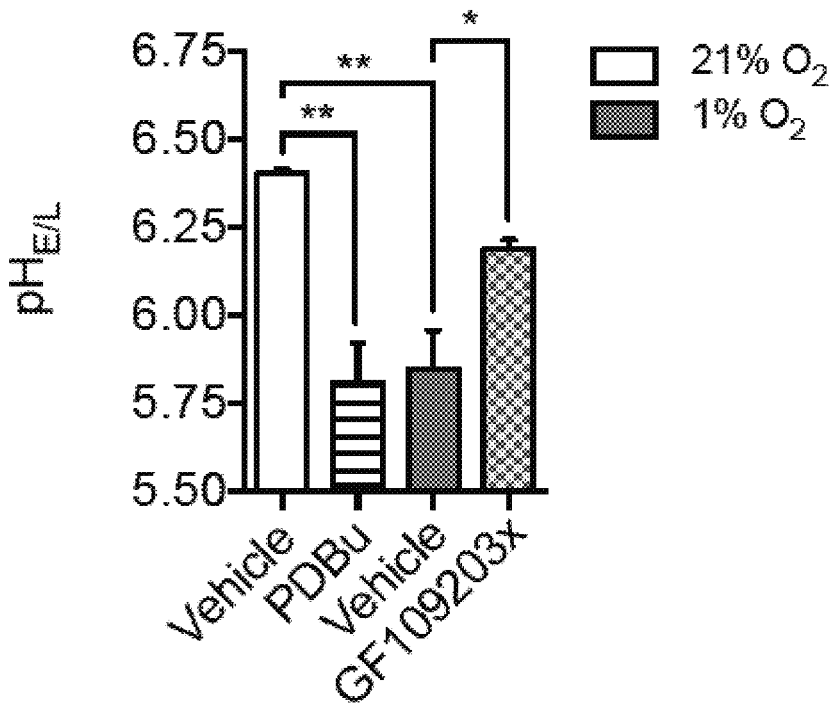
Figure 8H:
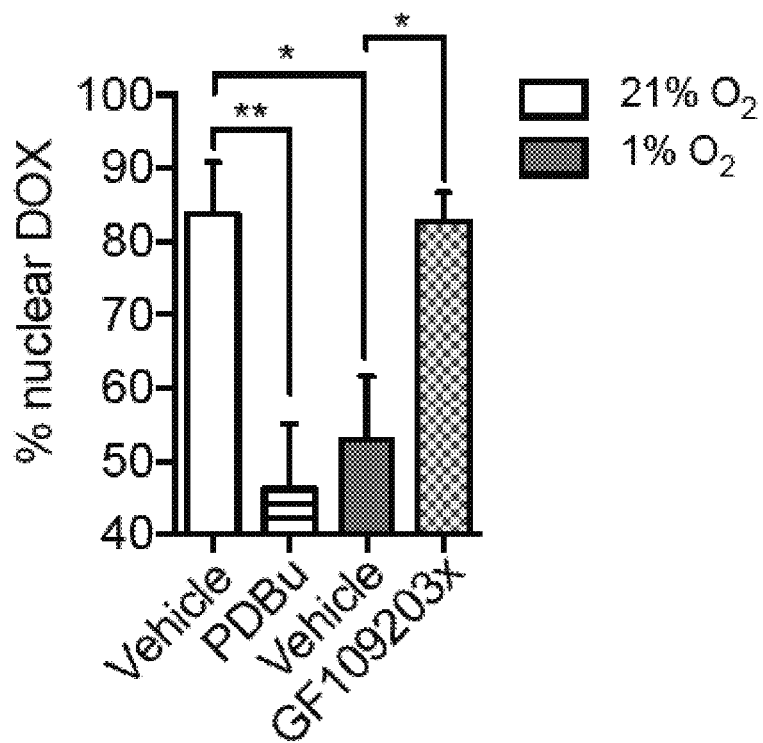

To first show that PKC is activated by hypoxia, the inventors used a phospho-(Ser) PKC substrate Ab in western blotting of total cell lysates from cells incubated under hypoxic conditions for various time points. Results indicated that hypoxia rapidly increases the phosphorylation of intracellular PKC substrates in HT-1080 and MDA-MB-231 cells with maximal effect observed at 1 and 2 hours (FIGS. 8A-B). Co-immunoprecipitation assays using HT-1080 cells resulted in detection of PKC in the RACK1 immunoprecipitate only in cells treated with the PKC activator phorbol-12,13-dibutyrate (PDBu) or cells incubated under hypoxic conditions, suggesting that RACK1 interacts with activated PKC in hypoxia (FIG. 8C). Treatment of the cells with PDBu promoted the association of NHE6 with RACK1 (FIG. 8D) and the relocalization of NHE6 from endosomes to the plasma membrane under normoxia (FIG. 8E). In contrast, inhibition of PKC with GF109203X[38] [39] blocked hypoxia-induced NHE6 relocalization (FIG. 8F), indicating that the plasma membrane mobilization of NHE6 in hypoxia is associated with PKC activation. Consistent with this interpretation, PKC inhibition allowed partial recovery of normal pH values under hypoxic conditions (FIG. 8G) and promoted the accumulation of Dox in the nuclear compartment (FIG. 8H). These results suggest that the increased binding of NHE6 to RACK1 occurs through a PKC-dependent mechanism and that this event regulates the delocalization of NHE6 under hypoxia resulting in changes in endosomal pH and drug sequestration.

Figure 9A:
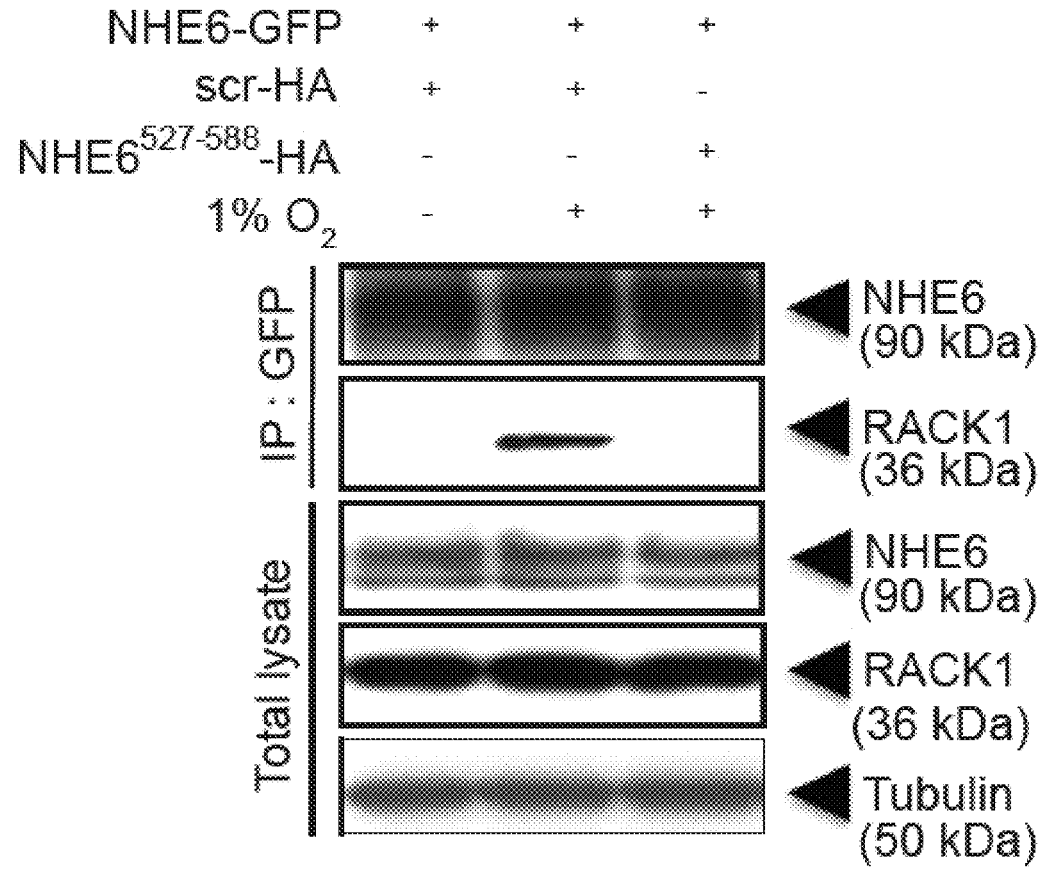
FIGS. 9A-G. Blockade of NHE6-RACK1 interaction prevents NHE6 redistribution to the plasma membrane. HT-1080 cells stably transfected with NHE6-GFP and transiently transfected with a plasmid encoding the NHE6$^{527-588}$ peptide or scrambled peptide were incubated under 1% $O_2$ or 21% $O_2$ for 4 h (FIGS. 9A-C and E-G).
Figure 9B:
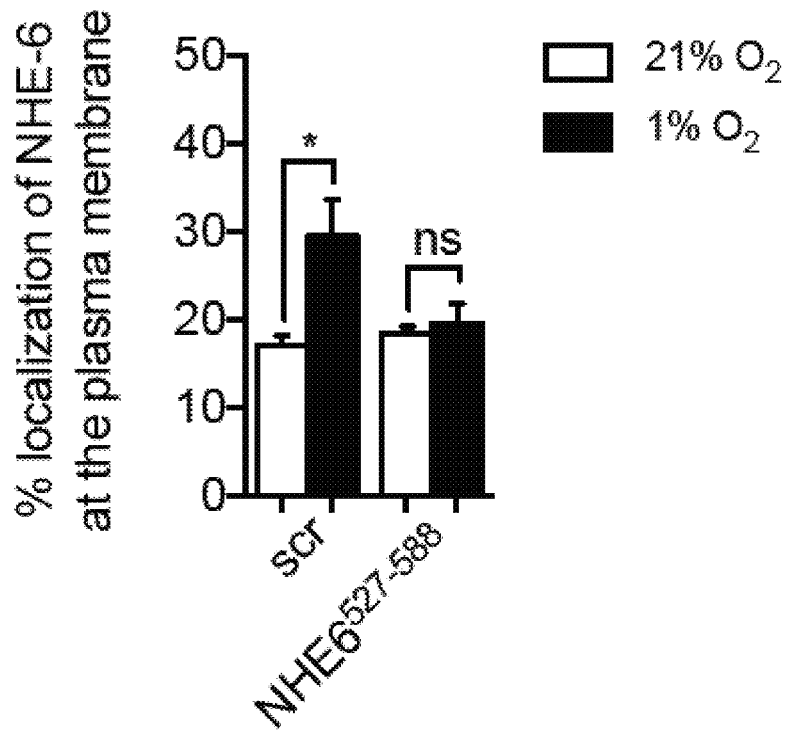
Figure 9C:
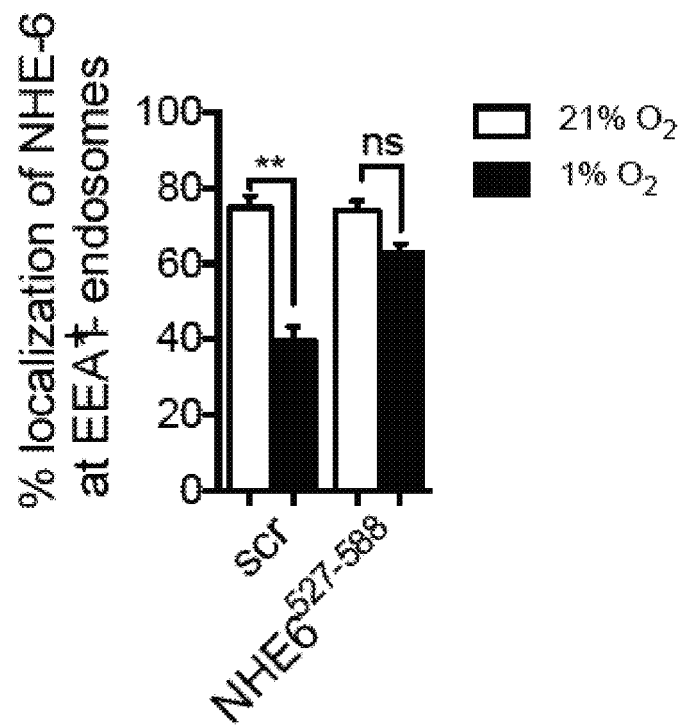
Figure 9D:
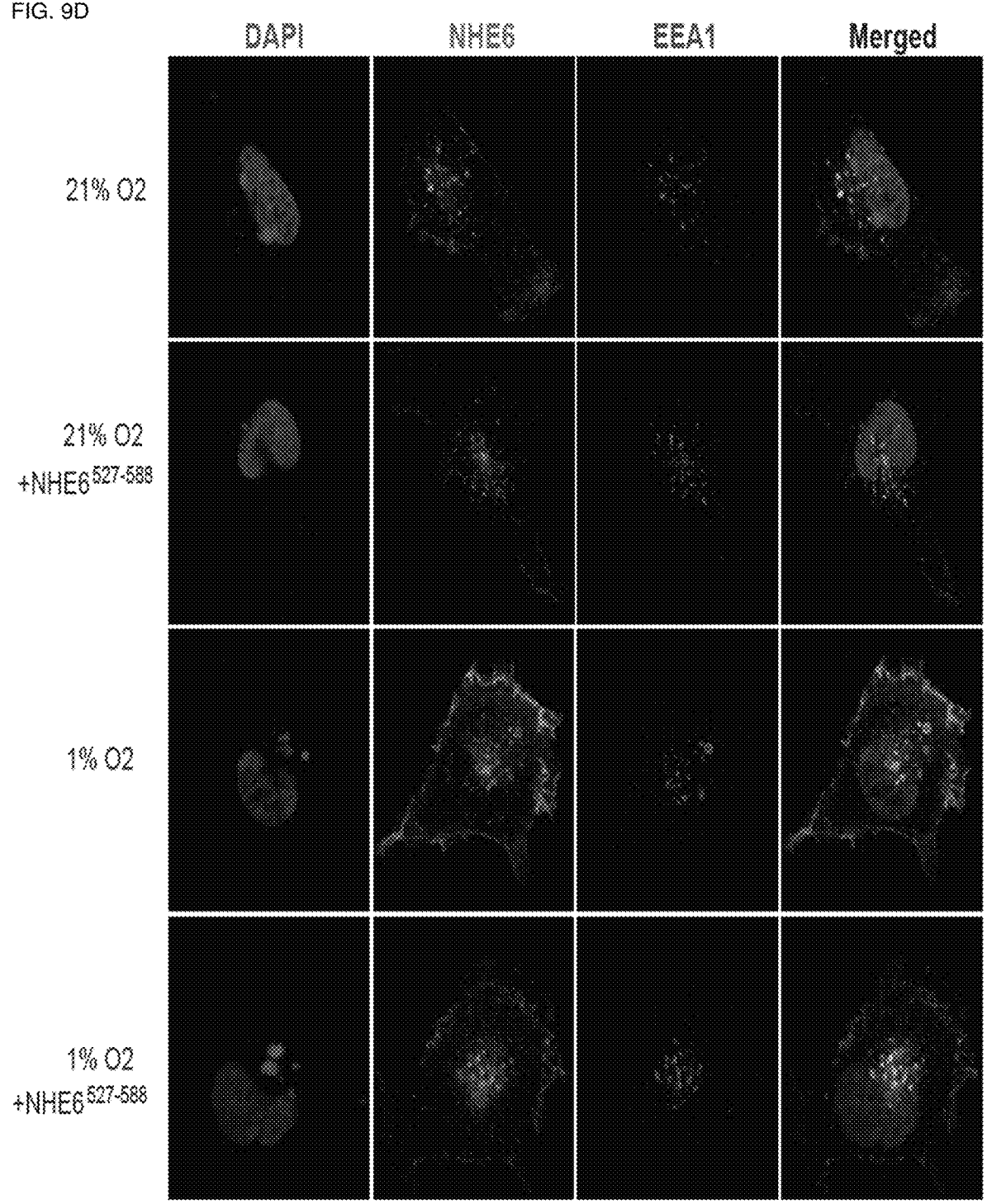
Figure 9E:
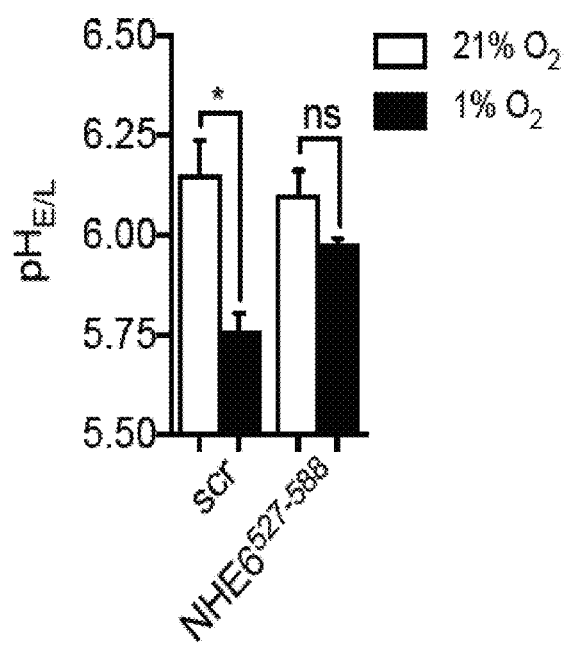
Figure 9F:
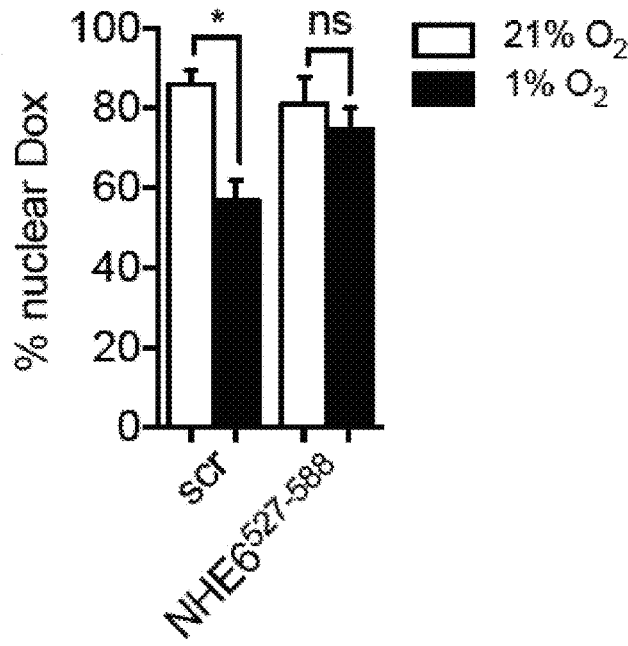
Figure 9G:
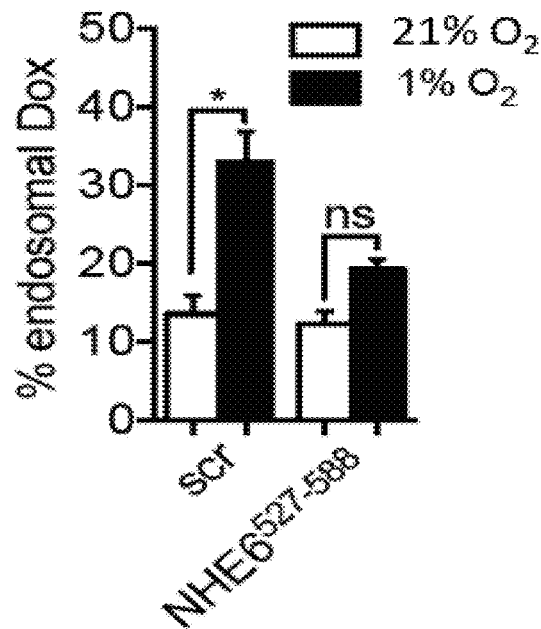

Example 7: NHE6-RACK1 Blockade Partially Restores Dox Sensitivity In Vitro and In Vivo The middle portion (position 527-588) of the NHE6 cytoplasmic tail has previously been reported to interact with RACK1[31]. Stable HT-1080 cells expressing the NHE6$^{527-588}$ fragment or a scrambled counterpart were generated. Results from co-immunoprecipitation assays indicated that ectopic expression of the NHE6$^{527-588}$ sequence, but not the control peptide sequence, prevented hypoxia-induced interaction of NHE6 with RACK1 (FIG. 9A). Furthermore, expression of NHE6$^{527-588}$ in cells greatly impaired hypoxia-induced NHE6 relocalization from endosomes to the plasma membrane (FIGS. 9B-D), intravesicular hyperacidification (FIG. 9E), diminution in nuclear Dox (FIG. 9F) and Dox accumulation within endosomes (FIG. 9G). In addition, results from cell viability assays indicated that overexpression of the NHE6$^{527-588}$ fragment did not change the sensitivity of the cells to Dox under normoxic conditions but a 2.8-fold increase in drug sensitivity was observed in cells exposed to hypoxia (Table VI). Taken together, these results demonstrate the usefulness of the NHE6$^{527-588}$ sequence in blocking hypoxia-induced NHE6-RACK1 interaction and the ensuing molecular events.

TABLE VI

IC$_{50}$ values of doxorubicin in HT-1080 overexpressing NHE6$^{527-588}$ peptide.

| IC50 (nM) | scr | NHE6$^{527-588}$ |
|---|---|---|
| 21% O2 | 117.2 +/− 19.8 | 136.9 +/− 20.4 |
| 1% O2 | 521.1 +/− 28.9 | 224.1 +/− 22.8 |
| Fold | 4.4 | 1.6 |
| p value | <0.0001 | 0.0081 |

Data are presented at the mean (nM)+/− standard deviation. IC$_{50}$, half maximal inhibitory concentration (n=3 independent experiments with 3 replicates in each experiment). P-values were determined with unpaired t-test with Welch's correction.

Figure 10A:
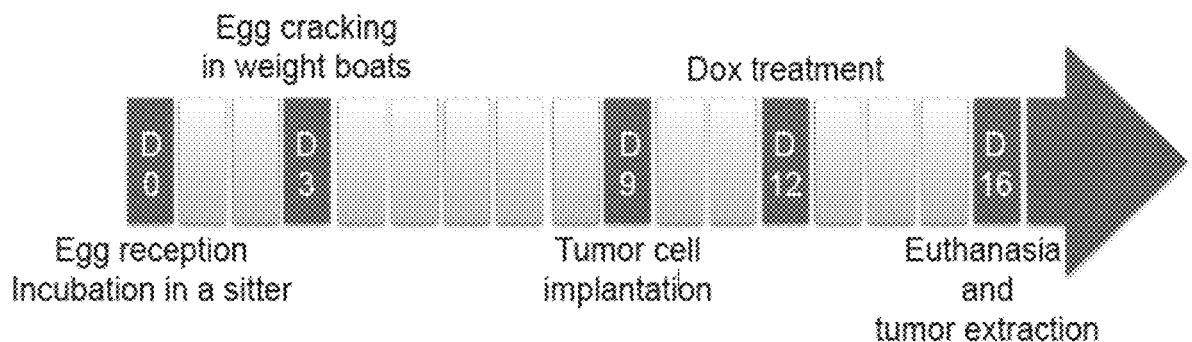
FIGS. 10A-H. Blockade of NHE6-RACK1 interaction minimizes Dox resistance in a chorioallantoic membrane xenograft assay.
Figure 10B:
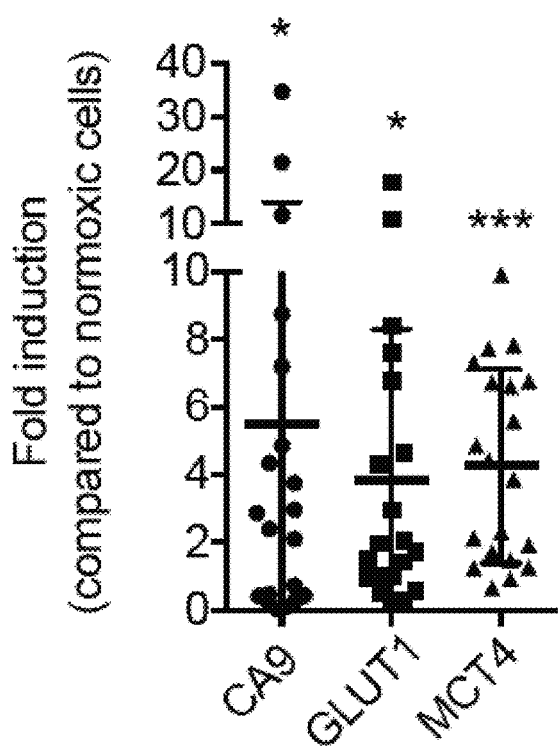
Figure 10C:
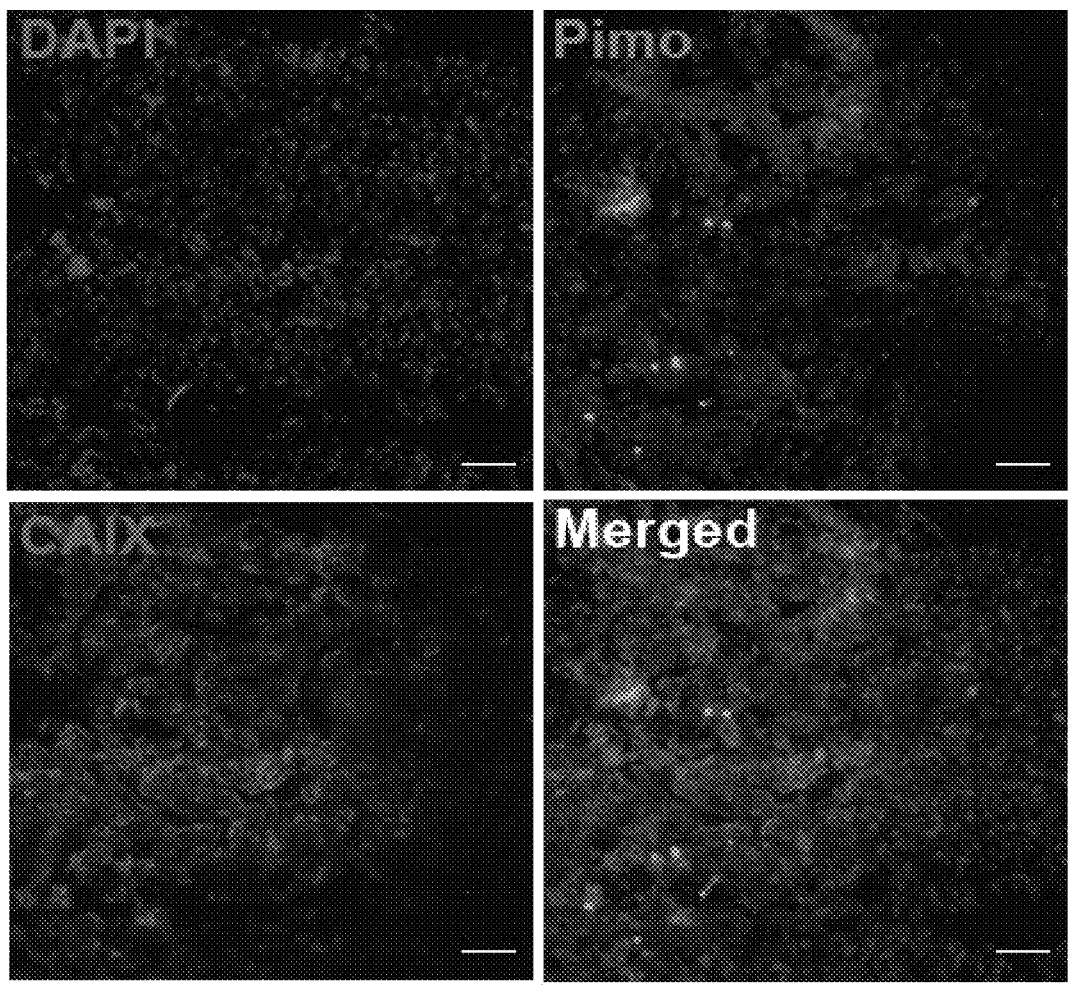
Figures 10D, 10E:
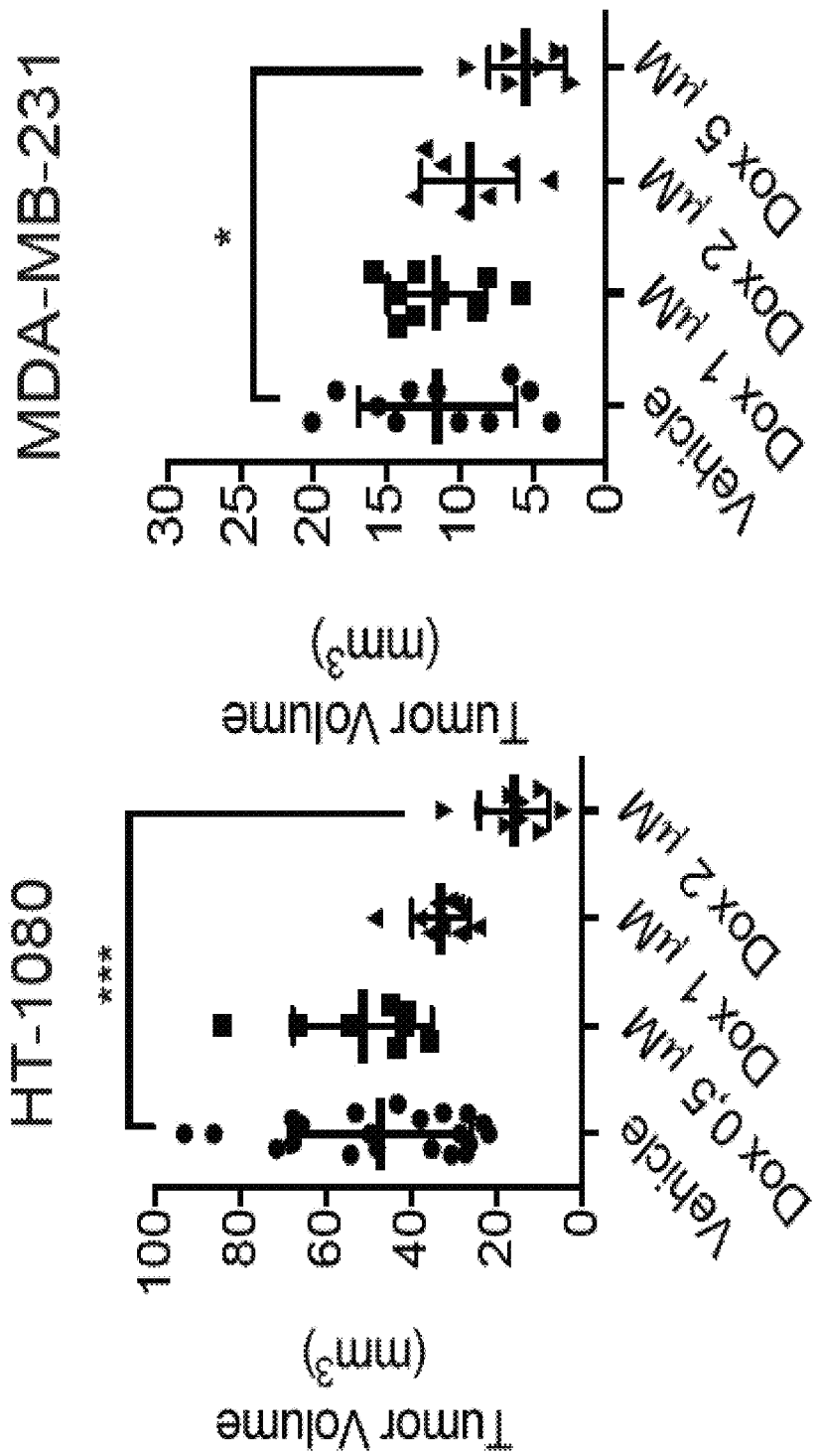
Figure 10F:
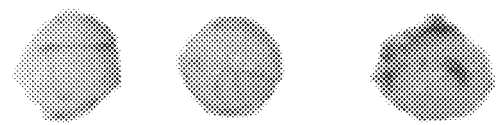
Figure 10F:
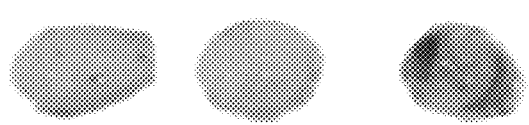
Figure 10F:
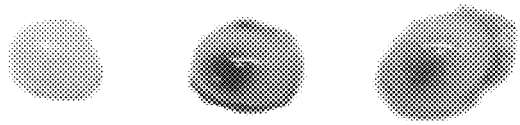
Figure 10F:
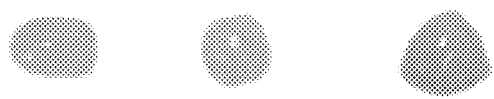
Figures 10G, 10H:
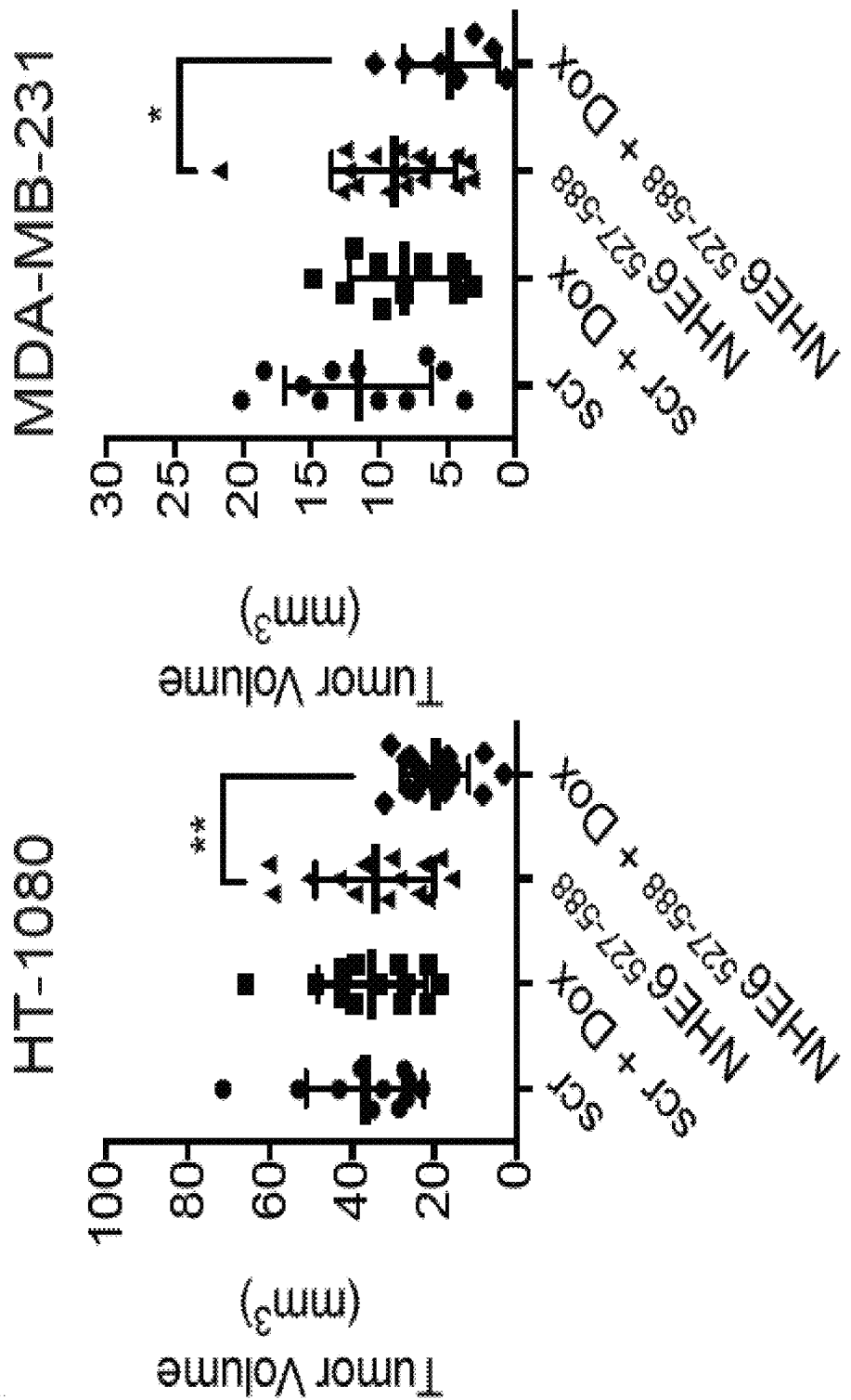
Figures 11A, 11B:
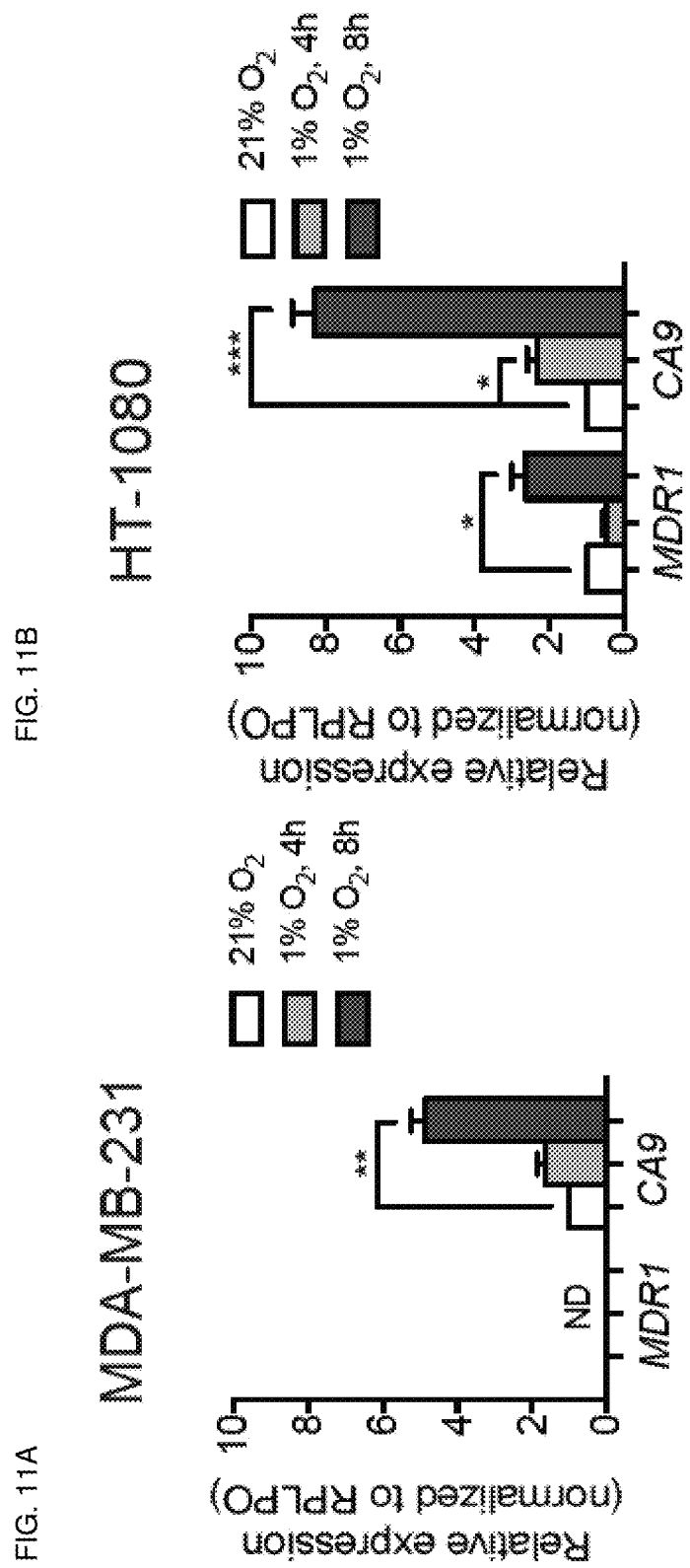
FIGS. 11A-E. Lack of expression of P-glycoprotein in endosomal or lysosomal compartments.
Figure 11C:
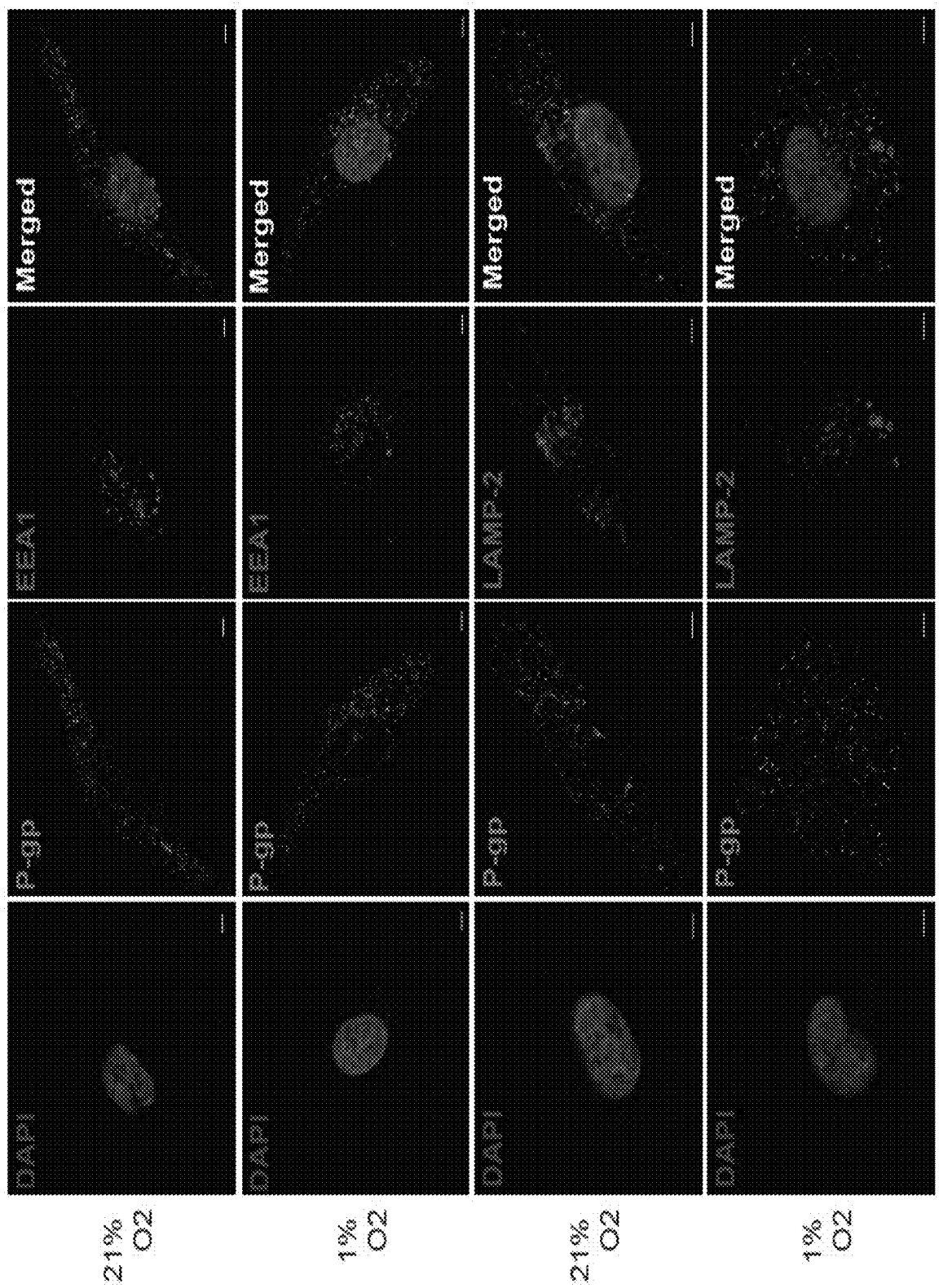
Figure 11D:
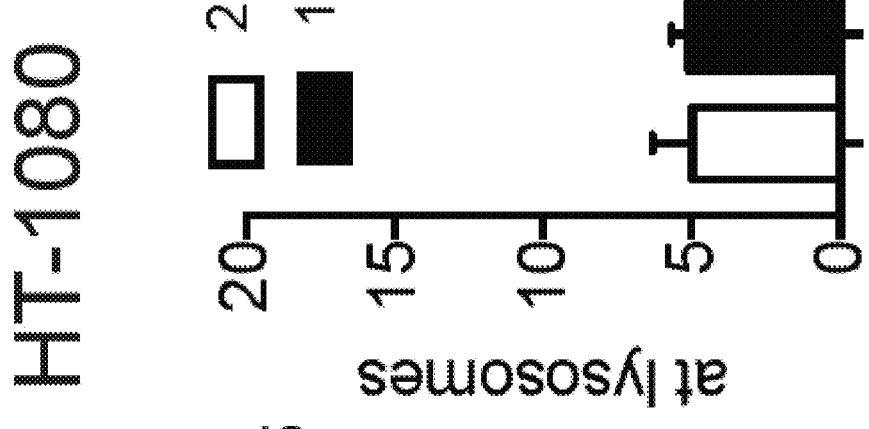
Figure 11E:
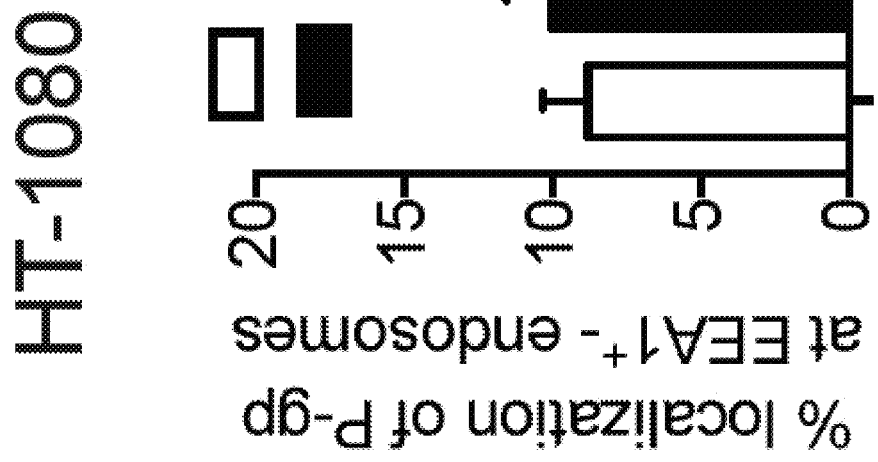

The in vitro results indicated that the interaction between RACK1 and NHE6 contributes to intrinsic Dox resistance in hypoxic cancer cells. To determine whether these observations were of relevance to tumor therapy in vivo, the inventors used an ex ovo chorioallantoic membrane (CAM) xenograft model in live chicken embryos[40]. MDA-MB-231 or HT-1080 cells, or cells expressing either the NHE6$^{527-588}$ competing fragment or its scrambled counterpart were inoculated onto the CAM of 9-day-old chick embryos. After allowing 3 days for cells to engraft, tumors were treated with Doxorubicin or PBS. Four days later, chick embryos were euthanized, and tumors were removed for analysis (FIG. 10A). To first ascertain that tumors implanted in CAM developed hypoxia, total mRNA was extracted from tumors generated by untransfected HT-1080 cells and gene expression of the hypoxic markers CA9, GLUT1 and MCT4 was measured by qPCR. Compared to HT-1080 cells cultured under normoxic conditions, tumor xenografts showed a 5.6-, 3.9- and 4.2-fold increase in CA9, GLUT1 and MCT4 gene expression, respectively (FIG. 10B). In addition, CA9 immunostaining in frozen tumor sections generally co-located with regions of binding of the hypoxic marker, pimonidazole (FIG. 10C), indicating the presence of hypoxic areas in xenograft tumors developed in the CAM assay. Of note, CA9 displayed greater areas of staining, consistent with earlier reports showing differences between the pO$_2$ dependency of 2-nitroimidazole binding and CA9 protein expression[41-43]. Dose-response Dox treatment indicated that tumor growth was significantly reduced in HT-1080 and MDA-MB-231 cells using 2 μM and 5 μM of Dox, respectively (FIGS. 10D-E). At lower concentrations (0.5 μM for HT-1080 cells and 1 μM for MDA-MB-231 cells), tumor growth was unaffected. Treatment of NHE6$^{527-588}$-overexpressing HT-1080 or MDA-MB-231 tumor xenografts with these suboptimal concentrations of Dox lead to a small but significant decrease in tumor volume compared to xenografts overexpressing a control peptide (FIGS. 10F-H). These observations indicate that blockade of NHE6-RACK1 interaction improved sensitivity of solid tumors to weak base chemotherapeutic treatment (e.g., Dox treatment).

Example 8: Localization of P-Glycoprotein in Tumor Cells

Among the cell lines used, only HT-1080 cells express detectable levels of p-glycoprotein (FIGS. 11 A-B). Confocal microscopy analysis of p-glycoprotein staining in HT-1080 cell line indicates that the protein does not co-localize with EEA1+ endosomes or LAMP1+ lysosomes under normoxic or hypoxic conditions data (FIGS. 11C-E) suggesting that this transporter is not a key component of endosomal Dox sequestration under acute hypoxia. Of note, a small but significant increase in MDR1 mRNA expression was observed after 8 h incubation in low O$_2$ which is consistent with a recent report showing that hypoxia can rapidly promote P-glycoprotein expression in laryngeal cancer cells[59].

Example 9: Cavity at the Surface of RACK1—Interaction with NHE6

Systematic inspection of the crystal structure of human RACK1, revealed clusters of exposed aromatic residues at the surface of RACK1. One of them involves four residues of the WD6 domain on the bottom face of RACK1; this site involves two tyrosine (Y) residues, one phenylalanine residue (F) and one tryptophan (W) residue. This site was also identified using IsoCleft™ Finder tool (Kurbatova, 2013) in domains WD5-7 that can correspond to the typical small size of transient protein-protein interactions. This cavity is formed by a total of 12 residues found on the WD5 and WD6 domains of the bottom face of the human RACK1 protein (see underlined residues in WD5: TNHIGHTGYLNTVTV SPDGSLCASGGKDGQAMLWDLNEG (SEQ ID NO: 56); and WD6: KHLYTLDGGDIINALCFSPN RYWLCAATGPSIKIWDLEGKIIVDEL (SEQ ID NO: 57). The two sites identified on the bottom face of RACK1 partially overlapped with the two tyrosine residues found on both sites; the remaining residues were adjacent to each other ("NHE binding site").

Example 10: Peptide Binding to RACK1

Figures 12A, 12B:
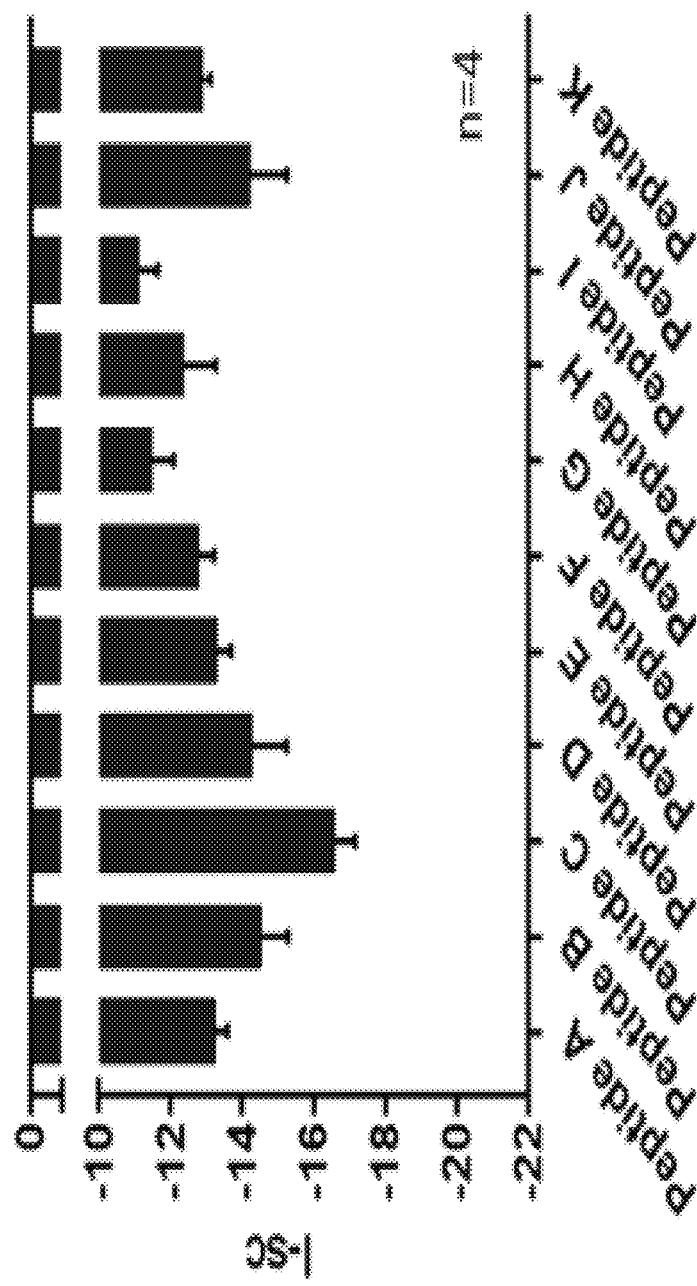
FIGS. 12A-D. Simulation of peptide-protein interaction through molecular docking refinement protocol.

A peptide-protein molecular docking refinement protocol was used as a tool to help further refining key residues in the NHE6 RACK1 binding domain. To do so, the [527-588] NHE6 sequence (SEQ ID NO: 2) of 62 amino acids was separated into eleven arbitrarily generated 10 amino acids overlapping peptides as shown in FIG. 12A. Each of peptides 1 to 11 (SEQ ID NOs: 3 to 5 and 10 to 17) was thereafter designated A to K, respectively.

Figures 12C, 12D:
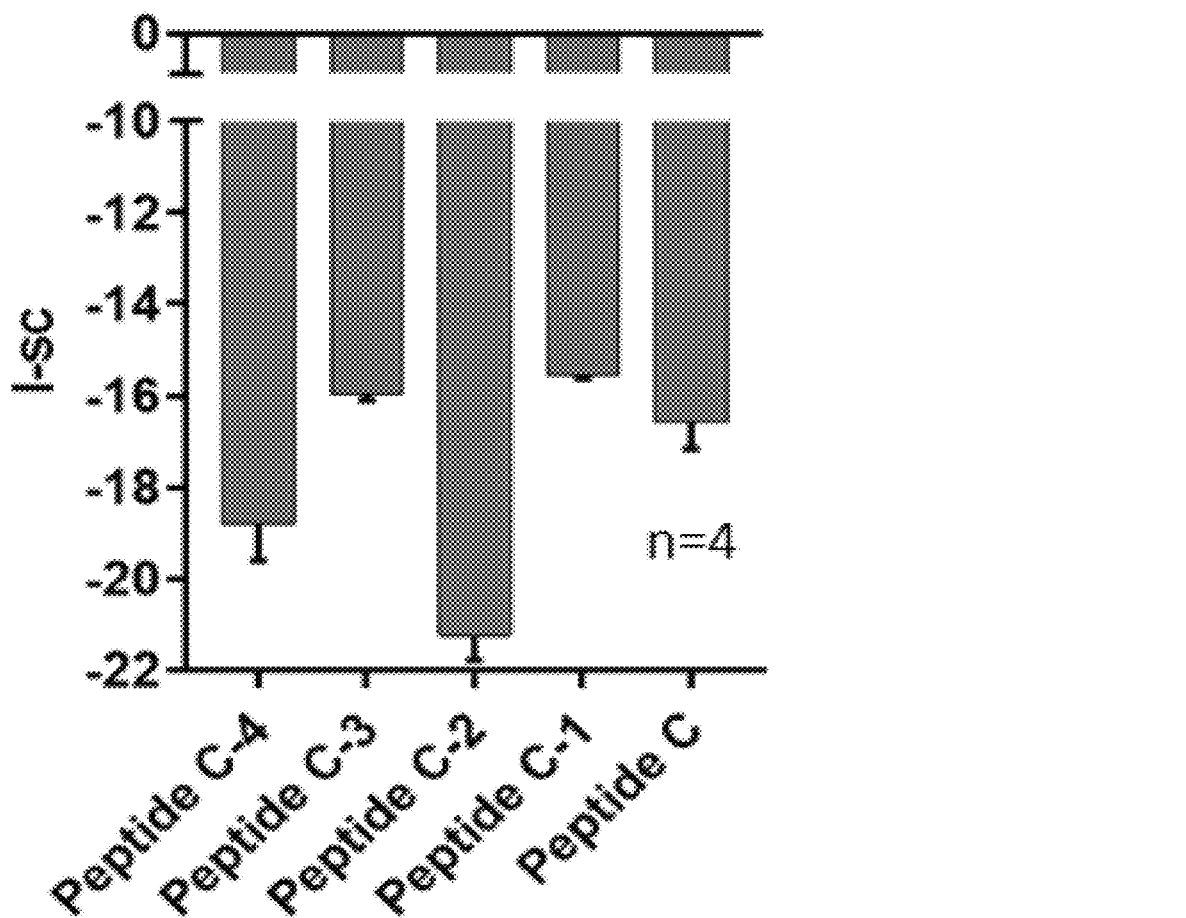

A 3D structure was then generated with the most likely initial conformation for every peptide using the PEP-FOLD™ de novo peptide structure prediction tool. The FlexPepDock™ protocol using each of these eleven peptides in close proximity to the NHE binding site disclosed in Example 9. The protocol yielded 200 possible structures of which only the Rosetta score value for the most energetically favourable structure was retained and presented under FIG. 12B. The most energetically favourable structure created yielded a result of −18.263 Rosetta energy units; it was a structure formed with Peptide C (SEQ ID NO: 5) which spans from W-538 to K-547 of the NHE6 sequence. The interface energy score for this peptide was significantly lower than other peptides except for peptides B, D and J (SEQ ID NOs: 4, 10 and 16) (peptide B, p=0.0763; peptide D, p=0.0901 and peptide J, p=0.0983). The search for key residues of the NHE6 RACK1 binding domain was further refined by creating four more 10 amino acid peptides (SEQ ID NOs: 6 to 9) derived from Peptide C (FIG. 12C). The derived peptides were created by sequentially removing one amino acid from the C-terminal end and adding another to the N-terminal end. Two of these new peptides produced structures that were even more energetically favourable than Peptide C (FIG. 12D). These energetically favourable peptides correspond to Peptide C-2 with −21.2428 Rosetta energy units and Peptide C-4 with −18.8083 Rosetta energy units. The interface energy score associated with Peptide C-4 was significantly lower than any other peptide tested through the docking protocol.

Following the molecular docking refinement protocol experiment, the 3D generated structures with the lowest interface energy score were inspected for each simulation presented in FIG. 12D to identify which residues could act as anchorage residues at the predicted NHE binding pocket of RACK1. The buried residues were identified for each of the 20 structures examined (4 structures for each of the 5 peptides). From all structures examined, 5 residues were found to be partially or completely buried in at least 50% of cases. These residues in order of prevalence were, Y-539 (95%), F-535 (88%), R-536 (75%), W-538 and Y-545 (67%). Since Tyrosine 539 was found to be the most often buried in our simulations it is predicted to be central to the NHE6/RACK interaction interface.

Example 11: NHE6-RACK1 Blocker Partially Restores Dox Sensitivity In Vitro

The IC50 (half-maximal inhibitory concentration) values of doxorubicin for HT1080 cancer cell line treated with the C2 peptide (RMWYNFDHNY (SEQ ID NO: 7)) or the C2WY→AA peptide (RMAANFDHNY (SEQ ID NO: 60)) were determined in normoxia or hypoxia.

Cells ($5 \times 10^3$) were cultured in 96-well plates and preincubated under 21% $O_2$ or 1% $O_2$ for 4 h following the addition of doxorubicin (dose response from $10^{-1}$ to $10^5$ nM) in the presence or absence of C2 and C2WY→AA peptides (SEQ ID NOs: 7 and 60) for 72 h. Cell viability was measured using the MTT dye (Life Technologies) according to the manufacturer's instructions. Because hypoxic conditions may affect the reduction of MTT to formazan, incubation of all cell cultures with MTT were performed under normoxic conditions. Each experiment was performed in triplicate. Log-scale dose-response data were plotted on a graph and a three-parameter nonlinear regression was applied to determine IC50 values. Data are presented as the mean (nM).

| Experiment 1: IC50 values | | | |
|---|---|---|---|
| Drug | Peptide | 21% $O_2$ | 1% $O_2$ |
| Doxorubicin | Vehicle | 16.0 | 83.8 |
| Doxorubicin | C2 - 0.25 µM | 12.2 | 39.7 |
| Doxorubicin | C2 - 5.00 µM | 17.2 | 39.1 |
| Doxorubicin | C2WY→AA - 0.25 µM | 21.3 | 99.1 |
| Doxorubicin | C2WY→AA - 5.00 µM | 16.4 | 76.4 |

| Experiment 2: IC50 values | | | |
|---|---|---|---|
| Drug | Peptide | 21% $O_2$ | 1% $O_2$ |
| Doxorubicin | Vehicle | 13.4 | 70.0 |
| Doxorubicin | C2 - 0.25 µM | 11.7 | 30.6 |
| Doxorubicin | C2 - 20.0 µM | 10.0 | 15.7 |
| Doxorubicin | C2WY→AA - 0.25 µM | 12.5 | 98.9 |
| Doxorubicin | C2WY→AA - 20.0 µM | 10.9 | 74.3 |

The foregoing shows that Tryptophan 538 and Tyrosine 539 contribute to the NHE6/RACK interaction interface and that smaller NHE6 fragment effectively act as NHE6/RACK blockers.

The scope of the claims should not be limited by the preferred embodiments set forth in the examples, but should be given the broadest interpretation consistent with the description as a whole.

REFERENCES

1 Holohan, C., Van Schaeybroeck, S., Longley, D. B. & Johnston, P. G. Cancer drug resistance: an evolving paradigm. *Nat Rev Cancer* 13, 714-726 (2013).

2 Vermorken, J. B. The role of anthracyclines in second-line therapy of ovarian cancer. *Int J Gynecol Cancer* 13 Suppl 2, 178-184 (2003).

3 Oostendorp, L. J., Stalmeier, P. F., Donders, A. R., van der Graaf, W. T. & Ottevanger, P. B. Efficacy and safety of palliative chemotherapy for patients with advanced breast cancer pretreated with anthracyclines and taxanes: a systematic review. *Lancet Oncol* 12, 1053-1061(2011).

4 Childhood Acute Lymphoblastic Leukaemia Collaborative, G. Beneficial and harmful effects of anthracyclines in the treatment of childhood acute lymphoblastic leukaemia: a systematic review and meta-analysis. *Br J Haematol* 145, 376-388 (2009).

5 Valero, V. et al. Phase II trial of docetaxel: a new, highly effective antineoplastic agent in the management of patients with anthracycline-resistant metastatic breast cancer. *J Clin Oncol* 13, 2886-2894 (1995).

6 Kim, S. B. et al. Combination of docetaxel and TSU-68, an oral antiangiogenic agent, in patients with metastatic breast cancer previously treated with anthracycline: randomized phase II multicenter trial. *Invest New Drugs* 32, 753-761 (2014).

7 Tredan, O., Galmarini, C. M., Patel, K. & Tannock, I. F. Drug resistance and the solid tumor microenvironment. *J Natl Cancer Inst* 99, 1441-1454 (2007).

8 Wojtkowiak, J. W., Verduzco, D., Schramm, K. J. & Gillies, R. J. Drug resistance and cellular adaptation to tumor acidic pH microenvironment. *Mol Pharm* 8, 2032-2038 (2011).

9 Wilson, W. R. & Hay, M. P. Targeting hypoxia in cancer therapy. *Nat Rev Cancer* 11, 393-410 (2011).

10 Baguley, B. C. Multiple drug resistance mechanisms in cancer. *Mol Biotechnol* 46, 308-316 (2010).

11 Lotz, C. et al. Role of the tumor microenvironment in the activity and expression of the p-glycoprotein in human colon carcinoma cells. *Oncol Rep* 17, 239-244 (2007).

12 Thews, O., Gassner, B., Kelleher, D. K., Schwerdt, G. & Gekle, M. Impact of extracellular acidity on the activity of P-glycoprotein and the cytotoxicity of chemotherapeutic drugs. *Neoplasia* 8, 143-152 (2006).

13 Alfarouk, K. O. et al. Resistance to cancer chemotherapy: failure in drug response from ADME to P-gp. *Cancer Cell Int* 15, 71 (2015).

14 Zhitomirsky, B. & Assaraf, Y. G. Lysosomal sequestration of hydrophobic weak base chemotherapeutics triggers lysosomal biogenesis and lysosome-dependent cancer multidrug resistance. *Oncotarget* 6, 1143-1156 (2015).

15 Avnet, S. et al. Altered pH gradient at the plasma membrane of osteosarcoma cells is a key mechanism of drug resistance. *Oncotarget* 7, 63408-63423 (2016).

16 Raghunand, N., Mahoney, B. P. & Gillies, R. J. Tumor acidity, ion trapping and chemotherapeutics. II. pH-dependent partition coefficients predict importance of ion trapping on pharmacokinetics of weakly basic chemotherapeutic agents. *Biochem Pharmacol* 66, 1219-1229 (2003).

17 Mahoney, B. P., Raghunand, N., Baggett, B. & Gillies, R. J. Tumor acidity, ion trapping and chemotherapeutics. I. Acid pH affects the distribution of chemotherapeutic agents in vitro. *Biochem Pharmacol* 66, 1207-1218 (2003).
18 Zhitomirsky, B. & Assaraf, Y. G. Lysosomes as mediators of drug resistance in cancer. *Drug Resist Updat* 24, 23-33 (2016).
19 Fuster, D. G. & Alexander, R. T. Traditional and emerging roles for the SLC9 Na+/H+ exchangers. *Pflugers Arch* 466, 61-76 (2014).
20 Nakamura, N., Tanaka, S., Teko, Y., Mitsui, K. & Kanazawa, H. Four Na+/H+ exchanger isoforms are distributed to Golgi and post-Golgi compartments and are involved in organelle pH regulation. *J Biol Chem* 280, 1561-1572 (2005).
21 Casey, J. R., Grinstein, S. & Orlowski, J. Sensors and regulators of intracellular pH. *Nat Rev Mol Cell Biol* 11, 50-61 (2010).
22 Morrow, E. M. et al. Identifying autism loci and genes by tracing recent shared ancestry. *Science* 321, 218-223 (2008).
23 Gilfillan, G. D. et al. SLC9A6 mutations cause X-linked mental retardation, microcephaly, epilepsy, and ataxia, a phenotype mimicking Angelman syndrome. *Am J Hum Genet* 82, 1003-1010 (2008).
24 Kondapalli, K. C., Prasad, H. & Rao, R. An inside job: how endosomal Na(+)/H(+) exchangers link to autism and neurological disease. *Front Cell Neurosci* 8, 172 (2014).
25 Kondapalli, K. C. et al. A leak pathway for luminal protons in endosomes drives oncogenic signalling in glioblastoma. *Nat Commun* 6, 6289 (2015).
26 Chen, J. et al. NHE9 induces chemoradiotherapy resistance in esophageal squamous cell carcinoma by upregulating the Src/Akt/beta-catenin pathway and Bcl-2 expression. *Oncotarget* 6, 12405-12420 (2015).
27 Lucien, F., Brochu-Gaudreau, K., Arsenault, D., Harper, K. & Dubois, C. M. Hypoxia-induced invadopodia formation involves activation of NHE-1 by the p90 ribosomal S6 kinase (p90RSK). *PLoS One* 6, e28851 (2011).
28 Gerweck, L. E., Kozin, S. V. & Stocks, S. J. The pH partition theory predicts the accumulation and toxicity of doxorubicin in normal and low-pH-adapted cells. *Br J Cancer* 79, 838-842 (1999).
29 Altan, N., Chen, Y., Schindler, M. & Simon, S. M. Defective acidification in human breast tumor cells and implications for chemotherapy. *J Exp Med* 187, 1583-1598 (1998).
30 Lucien, F., Harper, K., Pelletier, P. P., Volkov, L. & Dubois, C. M. Simultaneous pH measurement in endocytic and cytosolic compartments in living cells using confocal microscopy. *J Vis Exp* 28 (86) (2014).
31 Ohgaki, R., Fukura, N., Matsushita, M., Mitsui, K. & Kanazawa, H. Cell surface levels of organellar Na+/H+ exchanger isoform 6 are regulated by interaction with RACK1. *J Biol Chem* 283, 4417-4429 (2008).
32 Xinhan, L. et al. Na+/H+ exchanger isoform 6 (NHE6/SLC9A6) is involved in clathrin-dependent endocytosis of transferrin. *Am J Physiol Cell Physiol* 301, C1431-1444 (2011).
33 Ruan, Y. et al. Ribosomal RACK1 promotes chemoresistance and growth in human hepatocellular carcinoma. *J Clin Invest* 122, 2554-2566 (2012).
34 Ron, D. et al. Cloning of an intracellular receptor for protein kinase C: a homolog of the beta subunit of G proteins. *Proc Natl Acad Sci USA* 91, 839-843 (1994).
35 Rigas, A. C., Ozanne, D. M., Neal, D. E. & Robson, C. N. The scaffolding protein RACK1 interacts with androgen receptor and promotes cross-talk through a protein kinase C signaling pathway. *J Biol Chem* 278, 46087-46093 (2003).
36 Liedtke, C. M., Yun, C. H., Kyle, N. & Wang, D. Protein kinase C epsilon-dependent regulation of cystic fibrosis transmembrane regulator involves binding to a receptor for activated C kinase (RACK1) and RACK1 binding to Na+/H+ exchange regulatory factor. *J Biol Chem* 277 (2002).
37 Bird, R. J., Baillie, G. S. & Yarwood, S. J. Interaction with receptor for activated C-kinase 1 (RACK1) sensitizes the phosphodiesterase PDE4D5 towards hydrolysis of cAMP and activation by protein kinase C. *Biochem J* 432, 207-216 (2010).
38 Park, H. Y., Wu, H., Killoran, C. E. & Gilchrest, B. A. The receptor for activated C-kinase-I (RACK-I) anchors activated PKC-beta on melanosomes. *J Cell Sci* 117, 3659-3668 (2004).
39 Parent, A., Laroche, G., Hamelin, E. & Parent, J. L. RACK1 regulates the cell surface expression of the G protein-coupled receptor for thromboxane A(2). *Traffic* 9, 394-407 (2008).
40 Ribatti, D. The chick embryo chorioallantoic membrane in the study of tumor angiogenesis. *Rom J Morphol Embryol* 49, 131-135 (2008).
41 Rademakers, S. E., Lok, J., van der Kogel, A. J., Bussink, J. & Kaanders, J. H. Metabolic markers in relation to hypoxia; staining patterns and colocalization of pimonidazole, HIF-lalpha, CAIX, LDH-5, GLUT-1, MCT1 and MCT4. *BMC Cancer* 11, 167 (2011).
42 Shin, K. H. et al. Detecting changes in tumor hypoxia with carbonic anhydrase IX and pimonidazole. *Cancer Biol Ther* 6, 70-75 (2007).
43 Li, X. F. et al. Visualization of hypoxia in microscopic tumors by immunofluorescent microscopy. *Cancer Res* 67, 7646-7653 (2007).
44 De Milito, A. & Fais, S. Tumor acidity, chemoresistance and proton pump inhibitors. *Future Oncol* 1, 779-786 (2005).
45 Taylor, S. et al. Microenvironment acidity as a major determinant of tumor chemoresistance: Proton pump inhibitors (PPIs) as a novel therapeutic approach. *Drug Resist Updat* 23, 69-78 (2015).
46 Harguindey, S., Arranz, J. L., Wahl, M. L., Orive, G. & Reshkin, S. J. Proton transport inhibitors as potentially selective anticancer drugs. *Anticancer Res* 29, 2127-2136 (2009).
47 Parks, S. K., Chiche, J. & Pouyssegur, J. Disrupting proton dynamics and energy metabolism for cancer therapy. *Nat Rev Cancer* 13, 611-623 (2013).
48 Hashim, A. I., Zhang, X., Wojtkowiak, J. W., Martinez, G. V. & Gillies, R. J. Imaging pH and metastasis. *NMR Biomed* 24 (2011).
49 Gillies, R. J., Raghunand, N., Karczmar, G. S. & Bhujwalla, Z. M. MRI of the tumor microenvironment. *J Magn Reson Imaging* 16, 430-450 (2002).
50 Madshus, I. H. Regulation of intracellular pH in eukaryotic cells. *Biochem J* 250, 1-8 (1988).
51 Gerweck, L. E. & Seetharaman, K. Cellular pH gradient in tumor versus normal tissue: potential exploitation for the treatment of cancer. *Cancer Res* 56, 1194-1198 (1996).

52 Gerweck, L. E., Vijayappa, S. & Kozin, S. Tumor pH controls the in vivo efficacy of weak acid and base chemotherapeutics. *Mol Cancer Ther* 5, 1275-1279 (2006).

53 Raghunand, N. et al. Enhancement of chemotherapy by manipulation of tumour pH. *Br J Cancer* 80, 1005-1011 (1999).

54 Harguindey, S. et al. Cariporide and other new and powerful NHE1 inhibitors as potentially selective anti-cancer drugs—an integral molecular/biochemical/metabolic/clinical approach after one hundred years of cancer research. *J Transl Med* 11, 282, (2013).

55 Sharma, M. et al. pH Gradient Reversal: An Emerging Hallmark of Cancers. *Recent Pat Anticancer Drug Discov* 10, 244-258 (2015).

56 Miraglia, E. et al. Na+/H+ exchanger activity is increased in doxorubicin-resistant human colon cancer cells and its modulation modifies the sensitivity of the cells to doxorubicin. *Int J Cancer* 115, 924-929 (2005).

57 Jin, W. et al. Reversal of Imatinib resistance in BCR-ABL-positive leukemia after inhibition of the Na+/H+ exchanger. *Cancer Lett* 308, 81-90 (2011).

58 Pusztai, L. et al. Phase II study of tariquidar, a selective P-glycoprotein inhibitor, in patients with chemotherapy-resistant, advanced breast carcinoma. *Cancer* 104, 682-691 (2005).

59 Li, D., Zhou, L., Huang, J. & Xiao, X. Effect of multidrug resistance 1/P-glycoprotein on the hypoxia-induced multidrug resistance of human laryngeal cancer cells. *Oncol Lett* 12, 1569-1574 (2016).

60 Chen, A. et al. Photoacoustic "nanobombs" fight against undesirable vesicular compartmentalization of anticancer drugs. *Sci Rep* 5, 15527 (2015).

61 Brett, C. L., Wei, Y., Donowitz, M. & Rao, R. Human Na(+)/H(+) exchanger isoform 6 is found in recycling endosomes of cells, not in mitochondria. *Am J Physiol Cell Physiol* 282, C1031-1041 (2002).

62 Prior, M. J. et al. Quantitative proteomic analysis of the adipocyte plasma membrane. *J Proteome Res* 10, 4970-4982 (2011).

63 Liu, L., Schlesinger, P. H., Slack, N. M., Friedman, P. A. & Blair, H. C. High capacity Na+/H+ exchange activity in mineralizing osteoblasts. *J Cell Physiol* 226, 1702-1712 (2011).

64 Pulakat, L. et al. Ligand-dependent complex formation between the Angiotensin II receptor subtype AT2 and Na+/H+ exchanger NHE6 in mammalian cells. *Peptides* 26, 863-873 (2005).

65 Paolicchi, E. et al. Targeting hypoxic response for cancer therapy. *Oncotarget* 7, 13464-13478 (2016).

66 Charbonneau, M. et al. Hypoxia-inducible factor mediates hypoxic and tumor necrosis factor alpha-induced increases in tumor necrosis factor-alpha converting enzyme/ADAM17 expression by synovial cells. *J Biol Chem* 282, 33714-33724 (2007).

67 Leong, H. S. et al. Intravital imaging of embryonic and tumor neovasculature using viral nanoparticles. *Nat Protoc* 5, 1406-1417 (2010).

68 Kurbatova, N., Chartier, M., Zylber, M. I., & Najmanovich, R. (2013) IsoCleft Finder—a web-based tool for the detection and analysis of protein binding-site geometric and chemical similarities. F1000Research, 2, 117.

The invention claimed is:

1. A method of sensitizing a tumor cell of a subject to a weak base chemotherapeutic drug comprising administering an effective amount of a NHE6-RACK1 blocker to the subject, wherein the NHE6-RACK1 blocker is a peptide of at least 4 consecutive amino acids of the cytoplasmic tail of human NHE6.

2. The method of claim 1, wherein the weak base chemotherapeutic drug is an anthracycline.

3. The method of claim 2, wherein the weak base chemotherapeutic drug is daunorubicin, doxorubicin, or mitoxantrone, or a pharmaceutically acceptable salt thereof.

4. The method of claim 1, wherein the NHE6-RACK1 blocker is a peptide of at least 4 consecutive amino acids of the amino acid sequence at positions 527 to 591 of human NHE6.

5. The method of claim 4, wherein the peptide comprises at least 4 consecutive amino acids of the amino acid sequence at positions 527 to 591 of human NHE6, including tryptophan 538 and tyrosine 539.

6. The method of claim 4, wherein the peptide comprises at least 4 consecutive amino acids of the amino acid sequence at positions 530 to 547 of human NHE6, including tryptophan 538 and tyrosine 539.

7. The method of claim 4, wherein the peptide comprises at least 4 consecutive amino acids of the amino acid sequence at positions 536 to 545 of human NHE6, including tryptophan 538 and tyrosine 539.

8. The method of claim 4, wherein the peptide comprises RMWYNFDHNY (SEQ ID NO: 7).

9. The method of claim 4, wherein the NHE6-RACK1 blocker is a peptide of at least 4 consecutive amino acids comprising $W^{538}Y^{539}$.

10. A method of preventing or treating cancer or a symptom thereof in a subject, comprising administering (a) an effective amount of a NHE6-RACK1 blocker; and (b) an effective amount of a weak base chemotherapeutic drug, to the subject, wherein the NHE6-RACK1 blocker is a peptide of at least 4 consecutive amino acids of the cytoplasmic tail of human NHE6.

11. The method of claim 10, wherein (a) and (b) are simultaneous.

12. The method of claim 10, wherein (a) and (b) are sequential.

* * * * *

SEQUENCE LISTING

```
<160> NUMBER OF SEQ ID NOS: 66

<210> SEQ ID NO 1
<211> LENGTH: 65
<212> TYPE: PRT
<213> ORGANISM: homo sapiens

<400> SEQUENCE: 1

Thr Lys Ala Glu Ser Ala Trp Leu Phe Arg Met Trp Tyr Asn Phe Asp
1               5                   10                  15

His Asn Tyr Leu Lys Pro Leu Leu Thr His Ser Gly Pro Pro Leu Thr
            20                  25                  30

Thr Thr Leu Pro Ala Cys Cys Gly Pro Ile Ala Arg Cys Leu Thr Ser
        35                  40                  45

Pro Gln Ala Tyr Glu Asn Gln Glu Gln Leu Lys Asp Asp Asp Ser Asp
    50                  55                  60

Leu
65

<210> SEQ ID NO 2
<211> LENGTH: 62
<212> TYPE: PRT
<213> ORGANISM: Artificial Sequence
<220> FEATURE:
<223> OTHER INFORMATION: Synthetic construct

<400> SEQUENCE: 2

Thr Lys Ala Glu Ser Ala Trp Leu Phe Arg Met Trp Tyr Asn Phe Asp
1               5                   10                  15

His Asn Tyr Leu Lys Pro Leu Leu Thr His Ser Gly Pro Pro Leu Thr
            20                  25                  30
```

```
Thr Thr Leu Pro Ala Cys Cys Gly Pro Ile Ala Arg Cys Leu Thr Ser
            35                  40                  45

Pro Gln Ala Tyr Glu Asn Gln Glu Gln Leu Lys Asp Asp Asp
    50                  55                  60

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Thr Lys Ala Glu Ser Ala Trp Leu Phe Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct

<400> SEQUENCE: 4

Trp Leu Phe Arg Met Trp Tyr Asn Phe Asp
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Trp Tyr Asn Phe Asp His Asn Tyr Leu Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic construct

<400> SEQUENCE: 6

Met Trp Tyr Asn Phe Asp His Asn Tyr Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic construct

<400> SEQUENCE: 7

Arg Met Trp Tyr Asn Phe Asp His Asn Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 8

Phe Arg Met Trp Tyr Asn Phe Asp His Asn
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic construct

<400> SEQUENCE: 9

Leu Phe Arg Met Trp Tyr Asn Phe Asp His
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic construct

<400> SEQUENCE: 10

His Asn Tyr Leu Lys Pro Leu Leu Thr His
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Pro Leu Leu Thr His Ser Gly Pro Pro Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic construct

<400> SEQUENCE: 12

Ser Gly Pro Pro Leu Thr Thr Thr Leu Pro
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic construct

<400> SEQUENCE: 13

Thr Thr Thr Leu Pro Ala Cys Cys Gly Pro
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic construct
```

<400> SEQUENCE: 14

Ala Cys Cys Gly Pro Ile Ala Arg Cys Leu
1               5                  10

<210> SEQ ID NO 15
<211> LENGTH: 10
<212> TYPE: PRT
<213> ORGANISM: Artificial Sequence
<220> FEATURE:
<223> OTHER INFORMATION: Synthetic construct

<400> SEQUENCE: 15

Ala Arg Cys Leu Thr Ser Pro Gln Ala Tyr
1               5                  10

<210> SEQ ID NO 16
<211> LENGTH: 10
<212> TYPE: PRT
<213> ORGANISM: Artificial Sequence
<220> FEATURE:
<223> OTHER INFORMATION: Synthetic construct

<400> SEQUENCE: 16

Ser Pro Gln Ala Tyr Glu Asn Gln Glu Gln
1               5                  10

<210> SEQ ID NO 17
<211> LENGTH: 10
<212> TYPE: PRT
<213> ORGANISM: Artificial Sequence
<220> FEATURE:
<223> OTHER INFORMATION: Synthetic construct

<400> SEQUENCE: 17

Glu Asn Gln Glu Gln Leu Lys Asp Asp Asp
1               5                  10

<210> SEQ ID NO 18
<211> LENGTH: 10
<212> TYPE: PRT
<213> ORGANISM: Artificial Sequence
<220> FEATURE:
<223> OTHER INFORMATION: Synthetic construct

<400> SEQUENCE: 18

Ala Trp Leu Phe Arg Met Trp Tyr Asn Phe
1               5                  10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct

<400> SEQUENCE: 19

Ser Ala Trp Leu Phe Arg Met Trp Tyr Asn
1               5                  10

<210> SEQ ID NO 20
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 20

Glu Ser Ala Trp Leu Phe Arg Met Trp Tyr
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic construct

<400> SEQUENCE: 21

Trp Tyr Asn Phe Asp His Asn Tyr Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

Met Trp Tyr Asn Phe Asp His Asn Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic construct

<400> SEQUENCE: 23

Arg Met Trp Tyr Asn Phe Asp His Asn
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic construct

<400> SEQUENCE: 24

Phe Arg Met Trp Tyr Asn Phe Asp His
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic construct

<400> SEQUENCE: 25

Leu Phe Arg Met Trp Tyr Asn Phe Asp
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 26

Trp Leu Phe Arg Met Trp Tyr Asn Phe
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic construct

<400> SEQUENCE: 27

Ala Trp Leu Phe Arg Met Trp Tyr Asn
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Ser Ala Trp Leu Phe Arg Met Trp Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic construct

<400> SEQUENCE: 29

Trp Tyr Asn Phe Asp His Asn Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic construct

<400> SEQUENCE: 30

Met Trp Tyr Asn Phe Asp His Asn
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic construct

<400> SEQUENCE: 31

Arg Met Trp Tyr Asn Phe Asp His
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 32

Phe Arg Met Trp Tyr Asn Phe Asp
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic construct

<400> SEQUENCE: 33

Leu Phe Arg Met Trp Tyr Asn Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic construct

<400> SEQUENCE: 34

Trp Leu Phe Arg Met Trp Tyr Asn
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic construct

<400> SEQUENCE: 35

Ala Trp Leu Phe Arg Met Trp Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic construct

<400> SEQUENCE: 36

Trp Tyr Asn Phe Asp His Asn
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic construct

<400> SEQUENCE: 37

Met Trp Tyr Asn Phe Asp His
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 38

Arg Met Trp Tyr Asn Phe Asp
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic construct

<400> SEQUENCE: 39

Phe Arg Met Trp Tyr Asn Phe
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic construct

<400> SEQUENCE: 40

Leu Phe Arg Met Trp Tyr Asn
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic construct

<400> SEQUENCE: 41

Trp Leu Phe Arg Met Trp Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic construct

<400> SEQUENCE: 42

Trp Tyr Asn Phe Asp His
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic construct

<400> SEQUENCE: 43

Met Trp Tyr Asn Phe Asp
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic construct
```

```
<400> SEQUENCE: 44

Arg Met Trp Tyr Asn Phe
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic construct

<400> SEQUENCE: 45

Phe Arg Met Trp Tyr Asn
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic construct

<400> SEQUENCE: 46

Leu Phe Arg Met Trp Tyr
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic construct

<400> SEQUENCE: 47

Trp Tyr Asn Phe Asp
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic construct

<400> SEQUENCE: 48

Met Trp Tyr Asn Phe
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic construct

<400> SEQUENCE: 49

Arg Met Trp Tyr Asn
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic construct
```

```
<400> SEQUENCE: 50

Phe Arg Met Trp Tyr
1               5

<210> SEQ ID NO 51
<211> LENGTH: 4
<212> TYPE: PRT
<213> ORGANISM: Artificial Sequence
<220> FEATURE:
<223> OTHER INFORMATION: Synthetic construct

<400> SEQUENCE: 51

Trp Tyr Asn Phe
1

<210> SEQ ID NO 52
<211> LENGTH: 4
<212> TYPE: PRT
<213> ORGANISM: Artificial Sequence
<220> FEATURE:
<223> OTHER INFORMATION: Synthetic construct

<400> SEQUENCE: 52

Met Trp Tyr Asn
1

<210> SEQ ID NO 53
<211> LENGTH: 4
<212> TYPE: PRT
<213> ORGANISM: Artificial Sequence
<220> FEATURE:
<223> OTHER INFORMATION: Synthetic construct

<400> SEQUENCE: 53

Arg Met Trp Tyr
1

<210> SEQ ID NO 54
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (11)..(18)
<223> OTHER INFORMATION: Xaa can be any naturally occurring amino acid

<400> SEQUENCE: 54

Xaa Xaa Xaa Xaa Xaa Xaa Xaa Xaa Trp Tyr Xaa Xaa Xaa Xaa Xaa Xaa
1               5                   10                  15

Xaa Xaa

<210> SEQ ID NO 55
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
```

<220> FEATURE:
<221> NAME/KEY: misc_feature
<222> LOCATION: (5)..(10)
<223> OTHER INFORMATION: Xaa can be any naturally occurring amino acid

<400> SEQUENCE: 55

Xaa Xaa Trp Tyr Xaa Xaa Xaa Xaa Xaa Xaa
1               5                   10

<210> SEQ ID NO 56
<211> LENGTH: 39
<212> TYPE: PRT
<213> ORGANISM: Artificial Sequence
<220> FEATURE:
<223> OTHER INFORMATION: Synthetic construct

<400> SEQUENCE: 56

Thr Asn His Ile Gly His Thr Gly Tyr Leu Asn Thr Val Thr Val Ser
1               5                   10                  15

Pro Asp Gly Ser Leu Cys Ala Ser Gly Gly Lys Asp Gly Gln Ala Met
            20                  25                  30

Leu Trp Asp Leu Asn Glu Gly
        35

<210> SEQ ID NO 57
<211> LENGTH: 46
<212> TYPE: PRT
<213> ORGANISM: Artificial Sequence
<220> FEATURE:
<223> OTHER INFORMATION: Synthetic construct

<400> SEQUENCE: 57

Lys His Leu Tyr Thr Leu Asp Gly Gly Asp Ile Ile Asn Ala Leu Cys
1               5                   10                  15

Phe Ser Pro Asn Arg Tyr Trp Leu Cys Ala Ala Thr Gly Pro Ser Ile
            20                  25                  30

Lys Ile Trp Asp Leu Glu Gly Lys Ile Ile Val Asp Glu Leu
        35                  40                  45

<210> SEQ ID NO 58
<211> LENGTH: 30
<212> TYPE: PRT
<213> ORGANISM: Artificial Sequence
<220> FEATURE:
<223> OTHER INFORMATION: Synthetic construct

<400> SEQUENCE: 58

Ala Thr Gly Cys Gly Gly Ala Thr Cys Cys Ala Cys Ala Ala Ala
1               5                   10                  15

Gly Cys Ala Gly Ala Gly Ala Gly Thr Gly Cys Thr Thr Gly
            20                  25                  30

<210> SEQ ID NO 59
<211> LENGTH: 33
<212> TYPE: PRT
<213> ORGANISM: Artificial Sequence
<220> FEATURE:
<223> OTHER INFORMATION: Synthetic construct

```
<400> SEQUENCE: 59

Gly Cys Ala Thr Gly Ala Ala Thr Thr Cys Thr Thr Ala Ala Thr Cys
1               5                   10                  15

Ala Thr Cys Ala Thr Cys Thr Thr Thr Cys Ala Ala Cys Thr Gly Thr
                20                  25                  30

Thr

<210> SEQ ID NO 60
<211> LENGTH: 10
<212> TYPE: PRT
<213> ORGANISM: Artificial Sequence
<220> FEATURE:
<223> OTHER INFORMATION: Synthetic construct

<400> SEQUENCE: 60

Arg Met Ala Ala Asn Phe Asp His Asn Tyr
1               5                   10

<210> SEQ ID NO 61
<211> LENGTH: 4
<212> TYPE: PRT
<213> ORGANISM: Artificial Sequence
<220> FEATURE:
<223> OTHER INFORMATION: Synthetic construct

<400> SEQUENCE: 61

Asp Ser Asp Leu
1

<210> SEQ ID NO 62
<211> LENGTH: 669
<212> TYPE: PRT
<213> ORGANISM: Homo Sapiens

<400> SEQUENCE: 62

Met Ala Arg Arg Gly Trp Arg Arg Ala Pro Leu Arg Arg Gly Val Gly
1               5                   10                  15

Ser Ser Pro Arg Ala Arg Arg Leu Met Arg Pro Leu Trp Leu Leu Leu
                20                  25                  30

Ala Val Gly Val Phe Asp Trp Ala Gly Ala Ser Asp Gly Gly Gly Gly
            35                  40                  45

Glu Ala Arg Ala Met Asp Glu Glu Ile Val Ser Glu Lys Gln Ala Glu
        50                  55                  60

Glu Ser His Arg Gln Asp Ser Ala Asn Leu Leu Ile Phe Ile Leu Leu
65                  70                  75                  80

Leu Thr Leu Thr Ile Leu Thr Ile Trp Leu Phe Lys His Arg Arg Ala
                85                  90                  95

Arg Phe Leu His Glu Thr Gly Leu Ala Met Ile Tyr Gly Leu Leu Val
                100                 105                 110

Gly Leu Val Leu Arg Tyr Gly Ile His Val Pro Ser Asp Val Asn Asn
            115                 120                 125

Val Thr Leu Ser Cys Glu Val Gln Ser Ser Pro Thr Thr Leu Leu Val
        130                 135                 140

Thr Phe Asp Pro Glu Val Phe Phe Asn Ile Leu Leu Pro Pro Ile Ile
145                 150                 155                 160

Phe Tyr Ala Gly Tyr Ser Leu Lys Arg Arg His Phe Phe Arg Asn Leu
                165                 170                 175

Gly Ser Ile Leu Ala Tyr Ala Phe Leu Gly Thr Ala Ile Ser Cys Phe
                180                 185                 190
```

```
Val Ile Gly Ser Ile Met Tyr Gly Cys Val Thr Leu Met Lys Val Thr
            195                 200                 205
Gly Gln Leu Ala Gly Asp Phe Tyr Phe Thr Asp Cys Leu Leu Phe Gly
        210                 215                 220
Ala Ile Ser Ala Thr Asp Pro Val Thr Val Leu Ala Ile Phe His
225                 230                 235                 240
Glu Leu Gln Val Asp Val Glu Leu Tyr Ala Leu Leu Phe Gly Glu Ser
                245                 250                 255
Val Leu Asn Asp Ala Val Ala Ile Val Leu Ser Ser Ser Ile Val Ala
            260                 265                 270
Tyr Gln Pro Ala Gly Asp Asn Ser His Thr Phe Asp Val Thr Ala Met
        275                 280                 285
Phe Lys Ser Ile Gly Ile Phe Leu Gly Ile Phe Ser Gly Ser Phe Ala
    290                 295                 300
Met Gly Ala Ala Thr Gly Val Val Thr Ala Leu Val Thr Lys Phe Thr
305                 310                 315                 320
Lys Leu Arg Glu Phe Gln Leu Leu Glu Thr Gly Leu Phe Phe Leu Met
                325                 330                 335
Ser Trp Ser Thr Phe Leu Leu Ala Glu Ala Trp Gly Phe Thr Gly Val
            340                 345                 350
Val Ala Val Leu Phe Cys Gly Ile Thr Gln Ala His Tyr Thr Tyr Asn
        355                 360                 365
Asn Leu Ser Thr Glu Ser Gln His Arg Thr Lys Gln Leu Phe Glu Leu
    370                 375                 380
Leu Asn Phe Leu Ala Glu Asn Phe Ile Phe Ser Tyr Met Gly Leu Thr
385                 390                 395                 400
Leu Phe Thr Phe Gln Asn His Val Phe Asn Pro Thr Phe Val Val Gly
                405                 410                 415
Ala Phe Val Ala Ile Phe Leu Gly Arg Ala Ala Asn Ile Tyr Pro Leu
            420                 425                 430
Ser Leu Leu Leu Asn Leu Gly Arg Arg Ser Lys Ile Gly Ser Asn Phe
        435                 440                 445
Gln His Met Met Met Phe Ala Gly Leu Arg Gly Ala Met Ala Phe Ala
    450                 455                 460
Leu Ala Ile Arg Asp Thr Ala Thr Tyr Ala Arg Gln Met Met Phe Ser
465                 470                 475                 480
Thr Thr Leu Leu Ile Val Phe Phe Thr Val Trp Val Phe Gly Gly Gly
                485                 490                 495
Thr Thr Ala Met Leu Ser Cys Leu His Ile Arg Val Gly Val Asp Ser
            500                 505                 510
Asp Gln Glu His Leu Gly Val Pro Glu Asn Glu Arg Arg Thr Thr Lys
        515                 520                 525
Ala Glu Ser Ala Trp Leu Phe Arg Met Trp Tyr Asn Phe Asp His Asn
    530                 535                 540
Tyr Leu Lys Pro Leu Leu Thr His Ser Gly Pro Pro Leu Thr Thr Thr
545                 550                 555                 560
Leu Pro Ala Cys Cys Gly Pro Ile Ala Arg Cys Leu Thr Ser Pro Gln
                565                 570                 575
Ala Tyr Glu Asn Gln Glu Gln Leu Lys Asp Asp Ser Asp Leu Ile
            580                 585                 590
Leu Asn Asp Gly Asp Ile Ser Leu Thr Tyr Gly Asp Ser Thr Val Asn
        595                 600                 605
```

Thr Glu Pro Ala Thr Ser Ser Ala Pro Arg Arg Phe Met Gly Asn Ser
610                 615                 620

Ser Glu Asp Ala Leu Asp Arg Glu Leu Ala Phe Gly Asp His Glu Leu
625                 630                 635                 640

Val Ile Arg Gly Thr Arg Leu Val Leu Pro Met Asp Asp Ser Glu Pro
            645                 650                 655

Pro Leu Asn Leu Leu Asp Asn Thr Arg His Gly Pro Ala
            660                 665

<210> SEQ ID NO 63
<211> LENGTH: 617
<212> TYPE: PRT
<213> ORGANISM: Homo Sapiens

<400> SEQUENCE: 63

Met Asp Glu Glu Ile Val Ser Glu Lys Gln Ala Glu Glu Ser His Arg
1               5                   10                  15

Gln Asp Ser Ala Asn Leu Leu Ile Phe Ile Leu Leu Thr Leu Thr
            20                  25                  30

Ile Leu Thr Ile Trp Leu Phe Lys His Arg Arg Ala Arg Phe Leu His
            35                  40                  45

Glu Thr Gly Leu Ala Met Ile Tyr Gly Leu Leu Val Gly Leu Val Leu
50                  55                  60

Arg Tyr Gly Ile His Val Pro Ser Asp Val Asn Asn Val Thr Leu Ser
65                  70                  75                  80

Cys Glu Val Gln Ser Ser Pro Thr Thr Leu Leu Val Thr Phe Asp Pro
                85                  90                  95

Glu Val Phe Phe Asn Ile Leu Leu Pro Pro Ile Ile Phe Tyr Ala Gly
            100                 105                 110

Tyr Ser Leu Lys Arg Arg His Phe Phe Arg Asn Leu Gly Ser Ile Leu
            115                 120                 125

Ala Tyr Ala Phe Leu Gly Thr Ala Ile Ser Cys Phe Val Ile Gly Ser
            130                 135                 140

Ile Met Tyr Gly Cys Val Thr Leu Met Lys Val Thr Gly Gln Leu Ala
145                 150                 155                 160

Gly Asp Phe Tyr Phe Thr Asp Cys Leu Leu Phe Gly Ala Ile Val Ser
                165                 170                 175

Ala Thr Asp Pro Val Thr Val Leu Ala Ile Phe His Glu Leu Gln Val
            180                 185                 190

Asp Val Glu Leu Tyr Ala Leu Leu Phe Gly Glu Ser Val Leu Asn Asp
            195                 200                 205

Ala Val Ala Ile Val Leu Ser Ser Ser Ile Val Ala Tyr Gln Pro Ala
210                 215                 220

Gly Asp Asn Ser His Thr Phe Asp Val Thr Ala Met Phe Lys Ser Ile
225                 230                 235                 240

Gly Ile Phe Leu Gly Ile Phe Ser Gly Ser Phe Ala Met Gly Ala Ala
                245                 250                 255

Thr Gly Val Val Thr Ala Leu Val Thr Lys Phe Thr Lys Leu Arg Glu
            260                 265                 270

Phe Gln Leu Leu Glu Thr Gly Leu Phe Phe Leu Met Ser Trp Ser Thr
            275                 280                 285

Phe Leu Leu Ala Glu Ala Trp Gly Phe Thr Gly Val Val Ala Val Leu
290                 295                 300

Phe Cys Gly Ile Thr Gln Ala His Tyr Thr Tyr Asn Asn Leu Ser Thr
305                 310                 315                 320

-continued

```
Glu Ser Gln His Arg Thr Lys Gln Leu Phe Glu Leu Leu Asn Phe Leu
            325                 330                 335

Ala Glu Asn Phe Ile Phe Ser Tyr Met Gly Leu Thr Leu Phe Thr Phe
        340                 345                 350

Gln Asn His Val Phe Asn Pro Thr Phe Val Val Gly Ala Phe Val Ala
            355                 360                 365

Ile Phe Leu Gly Arg Ala Ala Asn Ile Tyr Pro Leu Ser Leu Leu Leu
370                 375                 380

Asn Leu Gly Arg Arg Ser Lys Ile Gly Ser Asn Phe Gln His Met Met
385                 390                 395                 400

Met Phe Ala Gly Leu Arg Gly Ala Met Ala Phe Ala Leu Ala Ile Arg
                405                 410                 415

Asp Thr Ala Thr Tyr Ala Arg Gln Met Met Phe Ser Thr Thr Leu Leu
            420                 425                 430

Ile Val Phe Phe Thr Val Trp Val Phe Gly Gly Thr Thr Ala Met
            435                 440                 445

Leu Ser Cys Leu His Ile Arg Val Gly Val Asp Ser Asp Gln Glu His
    450                 455                 460

Leu Gly Val Pro Glu Asn Glu Arg Arg Thr Thr Lys Ala Glu Ser Ala
465                 470                 475                 480

Trp Leu Phe Arg Met Trp Tyr Asn Phe Asp His Asn Tyr Leu Lys Pro
                485                 490                 495

Leu Leu Thr His Ser Gly Pro Pro Leu Thr Thr Thr Leu Pro Ala Cys
            500                 505                 510

Cys Gly Pro Ile Ala Arg Cys Leu Thr Ser Pro Gln Ala Tyr Glu Asn
        515                 520                 525

Gln Glu Gln Leu Lys Asp Asp Ser Asp Leu Ile Leu Asn Asp Gly
    530                 535                 540

Asp Ile Ser Leu Thr Tyr Gly Asp Ser Thr Val Asn Thr Glu Pro Ala
545                 550                 555                 560

Thr Ser Ser Ala Pro Arg Arg Phe Met Gly Asn Ser Ser Glu Asp Ala
                565                 570                 575

Leu Asp Arg Glu Leu Ala Phe Gly Asp His Glu Leu Val Ile Arg Gly
            580                 585                 590

Thr Arg Leu Val Leu Pro Met Asp Asp Ser Glu Pro Pro Leu Asn Leu
        595                 600                 605

Leu Asp Asn Thr Arg His Gly Pro Ala
    610                 615

<210> SEQ ID NO 64
<211> LENGTH: 649
<212> TYPE: PRT
<213> ORGANISM: Homo Sapiens

<400> SEQUENCE: 64

Met Asp Glu Glu Ile Val Ser Glu Lys Gln Ala Glu Glu Ser His Arg
1               5                   10                  15

Gln Asp Ser Ala Asn Leu Leu Ile Phe Ile Leu Leu Leu Thr Leu Thr
            20                  25                  30

Ile Leu Thr Ile Trp Leu Phe Lys His Arg Arg Ala Arg Phe Leu His
        35                  40                  45

Glu Thr Gly Leu Ala Met Ile Tyr Gly Leu Leu Val Gly Leu Val Leu
    50                  55                  60

Arg Tyr Gly Ile His Val Pro Ser Asp Val Asn Asn Val Thr Leu Ser
65                  70                  75                  80
```

```
Cys Glu Val Gln Ser Ser Pro Thr Thr Leu Leu Val Asn Val Ser Gly
             85                  90                  95
Lys Phe Tyr Glu Tyr Met Leu Lys Gly Glu Ile Ser Ser His Glu Leu
        100                 105                 110
Asn Asn Val Gln Asp Asn Glu Met Leu Arg Lys Val Thr Phe Asp Pro
            115                 120                 125
Glu Val Phe Phe Asn Ile Leu Leu Pro Pro Ile Ile Phe Tyr Ala Gly
        130                 135                 140
Tyr Ser Leu Lys Arg Arg His Phe Phe Arg Asn Leu Gly Ser Ile Leu
145                 150                 155                 160
Ala Tyr Ala Phe Leu Gly Thr Ala Ile Ser Cys Phe Val Ile Gly Ser
                165                 170                 175
Ile Met Tyr Gly Cys Val Thr Leu Met Lys Val Thr Gly Gln Leu Ala
            180                 185                 190
Gly Asp Phe Tyr Phe Thr Asp Cys Leu Leu Phe Gly Ala Ile Val Ser
        195                 200                 205
Ala Thr Asp Pro Val Thr Val Leu Ala Ile Phe His Glu Leu Gln Val
        210                 215                 220
Asp Val Glu Leu Tyr Ala Leu Leu Phe Gly Glu Ser Val Leu Asn Asp
225                 230                 235                 240
Ala Val Ala Ile Val Leu Ser Ser Ser Ile Val Ala Tyr Gln Pro Ala
                245                 250                 255
Gly Asp Asn Ser His Thr Phe Asp Val Thr Ala Met Phe Lys Ser Ile
            260                 265                 270
Gly Ile Phe Leu Gly Ile Phe Ser Gly Ser Phe Ala Met Gly Ala Ala
        275                 280                 285
Thr Gly Val Val Thr Ala Leu Val Thr Lys Phe Thr Lys Leu Arg Glu
        290                 295                 300
Phe Gln Leu Leu Glu Thr Gly Leu Phe Phe Leu Met Ser Trp Ser Thr
305                 310                 315                 320
Phe Leu Leu Ala Glu Ala Trp Gly Phe Thr Gly Val Val Ala Val Leu
                325                 330                 335
Phe Cys Gly Ile Thr Gln Ala His Tyr Thr Tyr Asn Asn Leu Ser Thr
            340                 345                 350
Glu Ser Gln His Arg Thr Lys Gln Leu Phe Glu Leu Leu Asn Phe Leu
        355                 360                 365
Ala Glu Asn Phe Ile Phe Ser Tyr Met Gly Leu Thr Leu Phe Thr Phe
        370                 375                 380
Gln Asn His Val Phe Asn Pro Thr Phe Val Val Gly Ala Phe Val Ala
385                 390                 395                 400
Ile Phe Leu Gly Arg Ala Ala Asn Ile Tyr Pro Leu Ser Leu Leu Leu
                405                 410                 415
Asn Leu Gly Arg Arg Ser Lys Ile Gly Ser Asn Phe Gln His Met Met
            420                 425                 430
Met Phe Ala Gly Leu Arg Gly Ala Met Ala Phe Ala Leu Ala Ile Arg
        435                 440                 445
Asp Thr Ala Thr Tyr Ala Arg Gln Met Met Phe Ser Thr Thr Leu Leu
        450                 455                 460
Ile Val Phe Phe Thr Val Trp Val Phe Gly Gly Gly Thr Thr Ala Met
465                 470                 475                 480
Leu Ser Cys Leu His Ile Arg Val Gly Val Asp Ser Asp Gln Glu His
                485                 490                 495
```

```
Leu Gly Val Pro Glu Asn Glu Arg Arg Thr Thr Lys Ala Glu Ser Ala
                500                 505                 510

Trp Leu Phe Arg Met Trp Tyr Asn Phe Asp His Asn Tyr Leu Lys Pro
        515                 520                 525

Leu Leu Thr His Ser Gly Pro Pro Leu Thr Thr Thr Leu Pro Ala Cys
    530                 535                 540

Cys Gly Pro Ile Ala Arg Cys Leu Thr Ser Pro Gln Ala Tyr Glu Asn
545                 550                 555                 560

Gln Glu Gln Leu Lys Asp Asp Ser Asp Leu Ile Leu Asn Asp Gly
                565                 570                 575

Asp Ile Ser Leu Thr Tyr Gly Asp Ser Thr Val Asn Thr Glu Pro Ala
                580                 585                 590

Thr Ser Ser Ala Pro Arg Arg Phe Met Gly Asn Ser Ser Glu Asp Ala
            595                 600                 605

Leu Asp Arg Glu Leu Ala Phe Gly Asp His Glu Leu Val Ile Arg Gly
        610                 615                 620

Thr Arg Leu Val Leu Pro Met Asp Asp Ser Glu Pro Pro Leu Asn Leu
625                 630                 635                 640

Leu Asp Asn Thr Arg His Gly Pro Ala
                645

<210> SEQ ID NO 65
<211> LENGTH: 317
<212> TYPE: PRT
<213> ORGANISM: Homo Sapiens

<400> SEQUENCE: 65

Met Thr Glu Gln Met Thr Leu Arg Gly Thr Leu Lys Gly His Asn Gly
1               5                   10                  15

Trp Val Thr Gln Ile Ala Thr Thr Pro Gln Phe Pro Asp Met Ile Leu
            20                  25                  30

Ser Ala Ser Arg Asp Lys Thr Ile Ile Met Trp Lys Leu Thr Arg Asp
        35                  40                  45

Glu Thr Asn Tyr Gly Ile Pro Gln Arg Ala Leu Arg Gly His Ser His
    50                  55                  60

Phe Val Ser Asp Val Val Ile Ser Ser Asp Gly Gln Phe Ala Leu Ser
65                  70                  75                  80

Gly Ser Trp Asp Gly Thr Leu Arg Leu Trp Asp Leu Thr Thr Gly Thr
                85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
        115                 120                 125

Ile Lys Leu Trp Asn Thr Leu Gly Val Cys Lys Tyr Thr Val Gln Asp
    130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
            180                 185                 190

Gly Tyr Leu Asn Thr Val Thr Val Ser Pro Asp Gly Ser Leu Cys Ala
        195                 200                 205

Ser Gly Gly Lys Asp Gly Gln Ala Met Leu Trp Asp Leu Asn Glu Gly
    210                 215                 220
```

```
Lys His Leu Tyr Thr Leu Asp Gly Gly Asp Ile Ile Asn Ala Leu Cys
225                 230                 235                 240

Phe Ser Pro Asn Arg Tyr Trp Leu Cys Ala Ala Thr Gly Pro Ser Ile
            245                 250                 255

Lys Ile Trp Asp Leu Glu Gly Lys Ile Ile Val Asp Glu Leu Lys Gln
            260                 265                 270

Glu Val Ile Ser Thr Ser Ser Lys Ala Glu Pro Pro Gln Cys Thr Ser
        275                 280                 285

Leu Ala Trp Ser Ala Asp Gly Gln Thr Leu Phe Ala Gly Tyr Thr Asp
290                 295                 300

Asn Leu Val Arg Val Trp Gln Val Thr Ile Gly Thr Arg
305                 310                 315
```

<210> SEQ ID NO 66
<211> LENGTH: 358
<212> TYPE: PRT
<213> ORGANISM: Homo Sapiens

<400> SEQUENCE: 66

```
Met Ser Ala Asp Ala Ala Gly Ala Pro Leu Pro Arg Leu Cys Cys
1               5                   10                  15

Leu Glu Lys Gly Pro Asn Gly Tyr Gly Phe His Leu His Gly Glu Lys
            20                  25                  30

Gly Lys Leu Gly Gln Tyr Ile Arg Leu Val Glu Pro Gly Ser Pro Ala
        35                  40                  45

Glu Lys Ala Gly Leu Leu Ala Gly Asp Arg Leu Val Glu Val Asn Gly
    50                  55                  60

Glu Asn Val Glu Lys Glu Thr His Gln Gln Val Val Ser Arg Ile Arg
65                  70                  75                  80

Ala Ala Leu Asn Ala Val Arg Leu Leu Val Val Asp Pro Glu Thr Asp
                85                  90                  95

Glu Gln Leu Gln Lys Leu Gly Val Gln Val Arg Glu Glu Leu Leu Arg
            100                 105                 110

Ala Gln Glu Ala Pro Gly Gln Ala Glu Pro Pro Ala Ala Ala Glu Val
        115                 120                 125

Gln Gly Ala Gly Asn Glu Asn Glu Pro Arg Glu Ala Asp Lys Ser His
    130                 135                 140

Pro Glu Gln Arg Glu Leu Arg Pro Arg Leu Cys Thr Met Lys Lys Gly
145                 150                 155                 160

Pro Ser Gly Tyr Gly Phe Asn Leu His Ser Asp Lys Ser Lys Pro Gly
                165                 170                 175

Gln Phe Ile Arg Ser Val Asp Pro Asp Ser Pro Ala Glu Ala Ser Gly
            180                 185                 190

Leu Arg Ala Gln Asp Arg Ile Val Glu Val Asn Gly Val Cys Met Glu
        195                 200                 205

Gly Lys Gln His Gly Asp Val Val Ser Ala Ile Arg Ala Gly Gly Asp
    210                 215                 220

Glu Thr Lys Leu Leu Val Val Asp Arg Glu Thr Asp Glu Phe Phe Lys
225                 230                 235                 240

Lys Cys Arg Val Ile Pro Ser Gln Glu His Leu Asn Gly Pro Leu Pro
                245                 250                 255

Val Pro Phe Thr Asn Gly Glu Ile Gln Lys Glu Asn Ser Arg Glu Ala
            260                 265                 270

Leu Ala Glu Ala Ala Leu Glu Ser Pro Arg Pro Ala Leu Val Arg Ser
        275                 280                 285
```

-continued

```
Ala Ser Ser Asp Thr Ser Glu Glu Leu Asn Ser Gln Asp Ser Pro Pro
    290             295                 300

Lys Gln Asp Ser Thr Ala Pro Ser Ser Thr Ser Ser Ser Asp Pro Ile
305             310                 315                 320

Leu Asp Phe Asn Ile Ser Leu Ala Met Ala Lys Glu Arg Ala His Gln
                325                 330                 335

Lys Arg Ser Ser Lys Arg Ala Pro Gln Met Asp Trp Ser Lys Lys Asn
            340                 345                 350

Glu Leu Phe Ser Asn Leu
            355
```